(12) United States Patent  (10) Patent No.: US 7,709,469 B2
Carroll et al.  (45) Date of Patent: May 4, 2010

(54) P2X₇ RECEPTOR ANTAGONISTS AND METHODS OF USE

(75) Inventors: William A. Carroll, Evanston, IL (US); Alan S. Florjancic, Kenosha, WI (US); Arturo Perez-Medrano, Grayslake, IL (US); Sridhar Peddi, Grayslake, IL (US)

(73) Assignee: Abbott Laboratories, Abbott Park, IL (US)

(*) Notice: Subject to any disclaimer, the term of this patent is extended or adjusted under 35 U.S.C. 154(b) by 737 days.

(21) Appl. No.: 11/593,377

(22) Filed: Nov. 6, 2006

(65) Prior Publication Data

US 2007/0105842 A1  May 10, 2007

Related U.S. Application Data

(60) Provisional application No. 60/734,220, filed on Nov. 7, 2005.

(51) Int. Cl.
*A61K 31/4439* (2006.01)
*C07D 403/14* (2006.01)
*C07D 249/08* (2006.01)

(52) U.S. Cl. ............. 514/218; 514/341; 514/383; 540/575; 546/272.4; 548/264.8; 548/265.8

(58) Field of Classification Search ............. None
See application file for complete search history.

(56) References Cited

U.S. PATENT DOCUMENTS 3,975,431 A   8/1976 White

FOREIGN PATENT DOCUMENTS

WO   2004/058731   7/2004

OTHER PUBLICATIONS

Dallacker et al, Chemiker-Zeitung (1986), 110(7-8), pp. 275-281.*
Plenkiewicz et al, Bulletin des Societes Chimiques Belges (1987), 96(9), pp. 675-709.*
Anderson, C., et al., "ATP-activated Glutamate Release through Non-Selective P2Z/P2X7 Like Channels in Cultured Mouse Astrocytes", Drug Dev. Res. vol. 50, p. 92, 2000.
Belletire, et al., "A Facile Synthesis of phenylacetic acids from aryl ketones", Synth. Commun., vol. 12, p. 763, 1982.
Bernabeu, et al., "A Unified Synthesis of Bifunctional 4-Substituted-1,2,3,4-tetrahydroisoquinoline Derivatives", Synth. Commun., vol. 34, p. 137, 2004.
Bianchi, et al., "Pharmacological characterization of recombinant human and rat P2X receptor subtypes", Eur. J. Pharmacol., vol. 376, pp. 127-138 (1999).
Chessell, et al., "Disruption of the P2X₇ purinoceptor gene abolishes chronic inflammatory and neuropathic pain", Pain, vol. 114, pp. 386-396, 2005.
Cohen, et al., "Synthesis and structure—activity relationships of new muscarinic antagonists", J. Pharm Sci., vol. 76, p. 848, 1987.
Collo, G., et al., "Tissue Distribution of the P2X₇ Receptor", Neuropharmacology, vol. 36, No. 9, pp. 1277-1283, 1997.

Dell' Antonio, et al., "Antinociceptive effect of a new P₂z/P2X7 antagonist, oxidized ATP, in arthritic rats", Neuroscience Lett., vol. 327, pp. 87-90, 2002.

(Continued)

*Primary Examiner*—Zinna N Davis
(74) *Attorney, Agent, or Firm*—Polsinelli Shughart PC

(57) ABSTRACT

The invention is directed to compounds that are P2X₇ antagonist and have the formula (I) or (II)

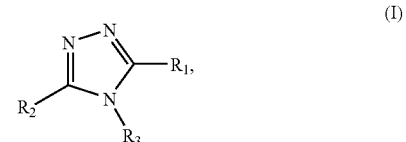

(I)

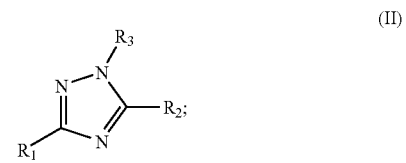

(II)

or a pharmaceutically acceptable salt, prodrug, salt of a prodrug or a combination thereof, wherein $R_1$, $R_2$, and $R_3$ are defined in the specification. The invention is also directed to a method of selectively inhibiting P2X₇ activity comprising administering to a patient in need of such treatment a therapeutically effective amount of a compound of formula (III), (IV) or (V)

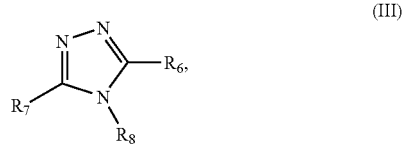

(III)

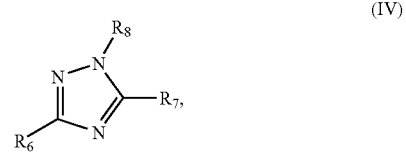

(IV)

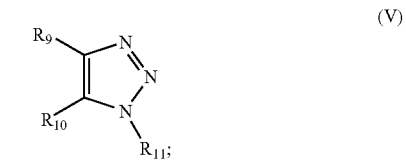

(V)

wherein $R_6$, $R_7$, $R_8$, $R_9$, $R_{10}$, and $R_{11}$ are defined in the specification.

48 Claims, No Drawings

OTHER PUBLICATIONS

Deuchars, et al., Neuronal $P2X_7$ Receptors are Targeted to Presynaptic Terminals in the Central and Peripheral Nervous Systems, J. Neuroscience, vol. 21, pp. 7143-7152, 2001.

Finkbeiner, H., "A Preparation of Aroyl and Acyl Formamidinium Salts", J. Org. Chem., vol. 30, p. 2861, 1965.

Fredga, A., "Dihydro-thionaphtheue-2- and -3-carboxylic Acids", Acta Chem. Scand., vol. 9, p. 719, 1955.

Griffiths, et al., "ATP Induces the Release of Il-1 from LPS-Primed Cells in Vivo", J. Immunology, vol. 154, pp. 2821-2828, 1995.

Jacobson, K.A., et al., "Adenosine and Adenine Nucleotides: From Molecular Biology to Integrative Physiology", L. Belardinelli and A. Pelleg (eds.), Kluwer Boston, pp. 149-166, 1995.

Jarvis, et al., "A-317491, a novel potent and selective non-nucleotide antagonist of $P2X_3$ and $P2X_{2/3}$ receptors, reduces chronic inflammatory and neuropathic pain in the rat", Proc. Natl. Acad., USA, vol. 99, pp. 17179-17184, 2002.

Lynch, et al., "Molecular and Functional Characterization of Human $P2X_2$ Receptors", Mol. Pharmacol. vol. 56, pp. 1171-1181, 1999.

Maiti, et al., "Lewis Acid-Promoted Favorskii-Type Ring Contraction of Some Cyclic α-Bromo Ketones and Their Acetals", Synthesis, vol. 9, p. 806, 1987.

Morita, et al., "Furopyridines. VI. Preparation and Reactions of 2- and 3- Substituted Furo[2,3-*b*]pyridines", *J.* Heterocycl. Chem., vol. 23, pp. 1465-1469, 1986.

Narcisse, et al., "The Cytokine IL-1β Transiently Enhances $P2X_7$, Receptor Expression and Function in Human Astrocytes", Glia, vol. 49, pp. 245-258, 2005.

Papp, et al., "Lack of ATP-evoked GABA and glutamate release in the hipposcampus of P2X7 receptor/ mice", Neuropharmacology and Neurotoxicology, vol. 15, pp. 2387-2391, 2004.

Parvathenani, et al., "$P2X_7$ Mediates Superoxide Production in Primary Microglia and Is up-regulated in a Transgenic Mouse Model of Alzheimer's Disease", J. Biol. Chemistry, vol. 278, pp. 13300-13317, 2003.

Perretti M., et al., "Evidence that endogenous interleukin-1 is involved in leukocyte migration in acute experimental inflammation in rats and mice", Agents Action, vol. 35 (1-2), pp. 71-78, 1992.

Sauter, et al., "Ein neuer Typ von analgetischen Antiphlogistica, 1. Mitt. Basisch substituierte 2,3-Dihydro-2-phenyl-benzo[b]thiophen-1,1-dioxide" Arch. Pharm., vol. 314, p. 567, 1981.

Scapecchi, et al., "Further structure-activity relationships in the series of tropanyl esters endowed with potent antinociceptive activity", Il Farmaco, vol. 53, p. 764, 1998.

Solle, et al., "Altered Cytokine Production in Mice Lacking $P2X_7$, Receptors", J. Biol. Chemistry, vol. 276, pp. 125-132, 2001.

Torok, K., et al., Measurement and drug induced modulation of interleukin-1 level during zymosan peritonitis in mice, Inflamm. Res. vol. 44(6) pp. 248-252, 1995.

Wang, X., et al., "$P2X_7$ receptor inhibition improves recovery after spinal cord injury", Nature Medicine, vol. 10, pp. 821-827, 2004.

* cited by examiner

P2X₇ RECEPTOR ANTAGONISTS AND METHODS OF USE

This application claims priority to the provisional application Ser. No. 60/734,220 filed on Nov. 7, 2005.

BACKGROUND OF THE INVENTION

This invention relates to aminotriazole analogues that are antagonists of P2X₇ receptors, and to the use of such compounds for treating conditions related to P2X₇ receptor activation.

P2X receptors are ionotropic receptors activated by ATP. The importance of P2X receptors in nociception is underscored by the variety of pain states in which this endogenous ligand can be released. Of the seven P2X receptors, the P2X₇ is distinguished by its ability to form a large pore upon prolonged or repeated agonist stimulation. It is partially activated by saturating concentrations of ATP, whereas it is fully activated by the synthetic ATP analog benzoylbenzoic ATP (BzATP) (Bianchi et al., *Eur. J. Pharmacol.* Vol. 376, pages 127-138, 1999). The P2X₇ receptor is expressed by presynaptic terminals in the central and peripheral nervous systems, antigen-presenting cells including macrophages, human epidermal Langerhans' cells, microglial cells and a number of tumor cell lines of varying origin (Jacobson K A, et al. "*Adenosine and Adenine Nucleotides: From Molecular Biology to Integrative Physiology*". L. Belardinelli and A. Pelleg (eds.), Kluwer, Boston, pages 149-166, 1995).

Recent studies demonstrated the participation of P2X₇ receptors in the modulation of electrical stimulation and ATP-evoked GABA and glutamate release from mouse hippocampal slices (Papp et al., *Neuropharmacolozy and Neurotoxicology* Vol. 15, pages 2387-2391, 2004)). In the central nervous system, the P2X₇ receptor is predominately expressed by microglia, the resident macrophages of the brain. On glial cells, the P2X₇ receptor has been shown to mediate release of glutamate (Anderson C. et al. *Drug Dev. Res.* Vol. 50. page 92, 2000). Upregulation of the P2X₇ receptor, most likely on activated microglia, was reported in association with ischemic damage and necrosis induced by occlusion of middle cerebral artery in rat brain (Collo G. et al. *Neuropharmacology*, Vol. 36, pages 1277-1283, 1997). Recent studies indicate a role of the P2X₇ receptor in the generation of superoxide in microglia, and upregulation of P2X₇ receptors around β-amyloid plaques in a transgenic mouse model for Alzheimer's disease (Parvathenani et al., *J. Biol. Chemistry*, Vol. 278, pages 13300-13317, 2003) and in multiple sclerosis lesions from autopsy brain sections (Narcisse et al., *Glia.* Vol. 49, pages 245-258 (2005).

Activation of the P2X₇ receptor on cells of the immune system (macrophages, mast cells and lymphocytes) leads to release of interleukin-1β (IL-1β), giant cell formation, degranulation, and L-selectin shedding. ATP has been shown to increase local release and processing of IL-1β following lipopolysaccharide S (LPS) intraperitoneal injections in rats through a P2X₇ receptor mediated mechanism (Griffiths et al., *J. Immunology* Vol. 154, pages 2821-2828 (1995); Solle et al., *J. Biol. Chemistry*. Vol. 276, pages 125-132, (2001)).

Oxidized ATP (oATP), a nonselective and irreversible P2X₇ antagonist, was recently reported to possess peripherally mediated antinociceptive properties in inflamed rats (Dell'Antonio et al. *Neuroscience Lett.*, Vol. 327, pages 87-90, 2002). Activation of P2X₇ receptors localized on presynaptic terminals in the central and peripheral nervous systems (Deuchars et al *J. Neuroscience*, Vol. 21, pages 7143-7152, 2001) induced release of the excitatory amino acid neurotransmitter glutamate.

Studies from mice lacking the P2X₇ receptor resulted in absence of inflammatory and neuropathic hypersensitivity to mechanical and thermal stimuli, indicating a link between a P2X₇ purinoceptor gene and inflammatory and neuropathic pain (Chessell et al., *Pain*, Vol 114, pages 386-396 (2005)).

Antagonists to the P2X₇ receptor significantly improved functional recovery and decreased cell death in spinal cord injury (SCI) animal models. Rats with SCI were administered P2X₇ receptor irreversible antagonists oATP and PPADS with a resulting decrease of histological injury and improved recovery of motor function after the lesions (Wang et al., *Nature Medicine* Vol. 10, pages B21-B27, 2004).

Taken together, these findings indicate that compounds acting at the P2X₇ receptor may have utility in the treatment of pain, including neuropathic pain, inflammatory processes, and degenerative conditions associated with disease states such as rheumatoid arthritis, osteoarthritis, psoriasis, allergic dermatitis, asthma, chronic obstructive pulmonary disease, airways hyper-responsiveness, septic shock, glomerulonephritis, irritable bowel disease, Crohn's disease, ulcerative colitis, atherosclerosis, growth and metastases of malignant cells, myoblastic leukemia, diabetes, Alzheimer's disease, multiple sclerosis, meningitis, osteoporosis, bum injury, ischemic heart disease, stroke and varicose veins.

In view of the above facts, there is a need for selective P2X₇ antagonist that can be efficiently used in preventing, treating, or ameliorating states as neuropathic pain, chronic inflammatory pain, inflammation and neurodegenerative conditions associated with several progressive CNS disorders, including, but not limited to, Alzheimer's disease, Parkinson's disease, depression, amyotrophic lateral sclerosis, Huntington's disease, dementia with Lewy bodies, multiple sclerosis as well as diminished CNS function resulting from traumatic brain injury.

SUMMARY OF THE INVENTION

The invention is directed to aminotriazole analog compounds as well as compositions comprising such compounds, and method of using the same to selectively inhibit P2X₇ receptor activity. Compounds of the invention are P2X₇ antagonists and have the formula (I) or (II)

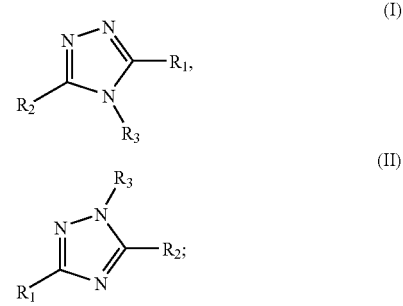

or a pharmaceutically acceptable salt, prodrug, salt of a prodrug or a combination thereof, wherein $R_1$ is hydrogen, alkyl, haloalkyl or —CN;

$R_2$ is —N(H)—$(CR_uR_v)$—$R_{2a}$, —N(H)—$R_{2b}$ or $R_{2b}$; and $R_3$ is

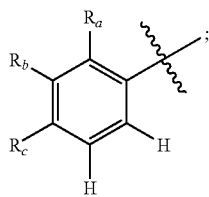

or
R$_2$ is

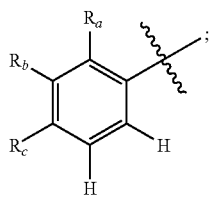

and R$_3$ is R$_{2b}$;
wherein
R$_{2a}$ is a group of formula (a) or (b);

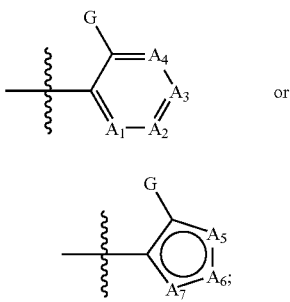

R$_{2b}$ is a group of formula (c), (d) or (e)

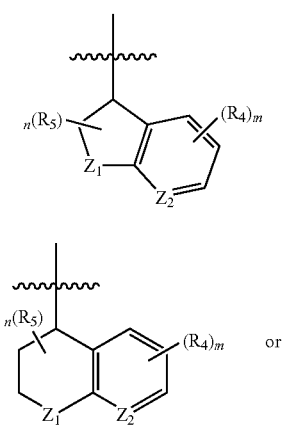

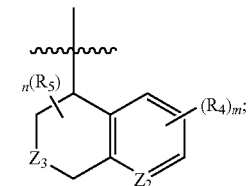

Z$_1$ at each occurrence is independently C, C(H), C(H)$_2$, O, S, S(O), S(O)$_2$, N(H), N(alkyl) or N(acyl);

Z$_2$ at each occurrence is independently C, C(H), or N;

Z$_3$ at each occurrence is independently O, S, S(O), S(O)$_2$, N(H), N(alkyl) or N(acyl);

R$_4$ at each occurrence is independently halo, alkyl, —CN, —OR$_A$, —SR$_A$, —N(R$_A$)(R$_B$) or haloalkyl;

R$_5$ at each occurrence is independently alkyl, halo or haloalkyl;

m at each occurrence is independently 0, 1, 2 or 3;

n at each occurrence is independently 0, 1, 2 or 3;

R$_a$ and R$_b$ at each occurrence are each independently halo, —CN, haloalkyl, haloalkoxy or alkyl;

R$_c$ at each occurrence is independently hydrogen, halo, haloalkyl, alkoxy, haloalkoxy or alkyl;

each of R$_u$ and R$_v$ at each occurrence is independently hydrogen, alkyl or haloalkyl;

A$_1$, A$_2$, A$_3$ and A$_4$ are —C(R$_w$); or one or two of A$_1$, A$_2$, A$_3$ and A$_4$ are N, and the others are —C(R$_w$); or one of A$_1$, A$_2$, A$_3$ and A$_4$ is N$^+$—O— and the others are —C(R$_w$); wherein R$_w$ at each occurrence is independently hydrogen, halo, alkyl, alkenyl, —OR$_A$, —SR$_A$, —N(R$_A$)(R$_B$) or haloalkyl;

A$_5$ is N, A$_6$ is O or S and A$_7$ is C(H) or C(alkyl), or

A$_5$ is N, A$_6$ is C(H) or C(alkyl), and A$_7$ is O or S, or one of A$_5$, A$_6$ and A$_7$ is S and the others are independently C(H) or C(alkyl);

G is -W$_2$ or -L$_2$-W$_2$; or

G is hydrogen, alkyl, —Oalkyl, —NH$_2$, —N(H)(alkyl), —N(alkyl)$_2$, —S(O)alkyl, —S(O)$_2$alkyl, —S(O)$_2$NH$_2$, —S(O)$_2$N(H)(alkyl), —S(O)$_2$N(alkyl)$_2$, —C(O)NH$_2$, —C(O)N(H)(alkyl), —C(O)N(alkyl)$_2$, -W$_2$ or -L$_2$-W$_2$, when one of A$_1$, A$_2$, A$_3$ and A$_4$ is N;

L$_2$ is N(H), N(alkyl), O, S, S(O), S(O)$_2$, S(O)$_2$N(H), SO$_2$N(alkyl), N(H)S(O)$_2$, N(alkyl)S(O)$_2$, CON(H), CON(alkyl), N(H)CO, N(alkyl)CO); and W$_2$ at each occurrence is independently aryl, heteroaryl or heterocycle; and each W$_2$ is independently unsubstituted or substituted with 1, 2 or 3 substituents selected from the group consisting of =O, halo, —CN, —NO$_2$, alkyl, alkenyl, —OR$_A$, —SR$_A$, —S(O)$_2$R$_A$, —S(O)$_2$N(R$_A$)(R$_B$), —N(R$_A$)(R$_B$), —C(O)R$_A$, —C(O)N(R$_A$)(R$_B$), —C(O)OR$_A$, haloalkyl, -alkyl-OR$_A$, -alkyl-SR$_A$, -alkyl-S(O)$_2$R$_A$, -alkyl-S(O)$_2$N(R$_A$)(R$_B$), -alkyl-N(R$_A$)(R$_B$), -alkyl-C(O)R$_A$, -alkyl-C(O)N(R$_A$)(R$_B$), and -alkyl-C(O)OR$_A$;

R$_A$ at each occurrence is independently hydrogen, alkyl, alkenyl or haloalkyl; and R$_B$ at each occurrence is independently hydrogen, alkyl, or haloalkyl.

Another aspect of the invention relates to a method of selectively inhibiting P2X$_7$ activity comprising administering to a patient in need of such treatment a therapeutically effective amount of a compound of formula (III), (IV) or (V)

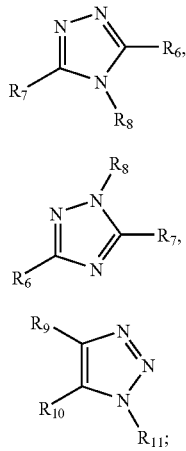
(III)
(IV)
(V)

or a pharmaceutically acceptable salt, prodrug, salt of a prodrug, or a combination thereof, wherein
$R_6$ is hydrogen, alkyl, haloalkyl or —CN;
$R_7$ is

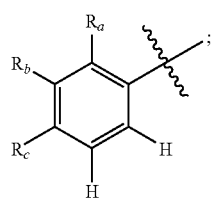

and $R_8$ is -W, —C($R_xR_y$)-$W_1$, —C($R_xR_y$)-$W_1$-$W_2$, or —C($R_xR_y$)-$W_1$-$L_2$-$W_2$, or
$R_8$ is

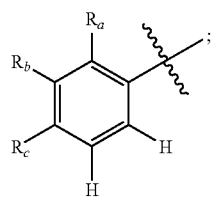

and $R_7$ is -W, —N(H)-W, -$L_1$-$W_1$, -$L_1$-$W_1$-$W_2$, or -$L_1$-$W_1$-$L_2$-$W_2$;
$R_{10}$ is

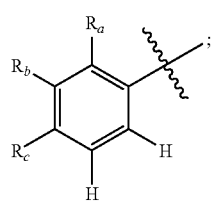

$R_{11}$ is —C($R_xR_y$)-$W_1$; and $R_9$ is hydrogen, alkyl, haloalkyl or —CN; or $R_{11}$ is

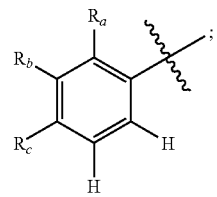

$R_{10}$ is —C($R_xR_y$)-$W_1$; and $R_9$ is hydrogen, alkyl, haloalkyl or —CN; or
$R_9$ is

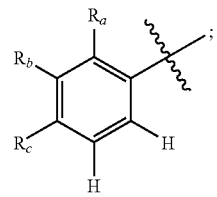

$R_{10}$ is —C($R_xR_y$)-$W_1$; and $R_{11}$ is hydrogen;
wherein
$R_a$ and $R_b$ at each occurrence are each independently halo, —CN, haloalkyl, haloalkoxy or alkyl;
$R_c$ at each occurrence is independently hydrogen, halo, haloalkyl, alkoxy, haloalkoxy or alkyl;
$L_1$ at each occurrence is independently —C($R_xR_y$), or —N(H)—C($R_uR_v$)$_p$—; p is 1. or 2;
each of $R_u$, $R_v$, $R_x$ and $R_y$ at each occurrence is independently hydrogen, alkyl or haloalkyl;
W is

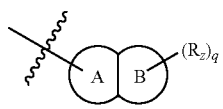

wherein
A is a five or six membered monocyclic ring selected from the group consisting of cycloalkyl and heterocycle and is optionally substituted with 1, 2, or 3 substituents selected from the group consisting of alkyl, halo and haloalkyl;
B is phenyl or monocyclic heteroaryl, optionally substituted with 1, 2 or 3 substituents selected from the group consisting of halo, alkyl, —CN, —O$R_A$, —S$R_A$, —N($R_A$)($R_B$) and haloalkyl;
q is 0 or 1;
$R_Z$ is $W_2$ or -$L_2$-$W_2$;
$L_2$ at each occurrence is independently O, N(H), or N(alkyl), S, S(O), S(O)$_2$, S(O)$_2$N(H), SO$_2$N(alkyl), N(H)S(O)$_2$, N(alkyl)S(O)$_2$, CON(H), CON(alkyl), N(H)CO, N(alkyl)CO);
$W_1$ at each occurrence is independently phenyl or monocyclic heteroaryl, wherein each $W_1$ is optionally fused with a monocyclic, five or six-membered ring selected from the group consisting of phenyl, heteroaryl, heterocycle, cycloalkyl and cycloalkenyl;

$W_2$, at each occurrence is independently aryl, heteroaryl, cycloalkyl, cycloalkenyl, or heterocycle;

each of $W_1$ and $W_2$, at each occurrence, is independently unsubstituted or substituted with 1, 2 or 3 substituents selected from the group consisting of alkyl, alkenyl, CN, $NO_2$, halo, =O, $-OR_A$, $-SR_A$, $-S(O)R_A$, $-S(O)_2R_A$, $-S(O)_2N(R_A)(R_B)$, $-N(R_A)(R_B)$, $-C(O)R_A$, $-C(O)OR_A$, $-C(O)N(R_A)(R_B)$, haloalkyl, -alkyl-$OR_A$, -alkyl-$SR_A$, -alkyl-$S(O)R_A$, -alkyl-$S(O)_2R_A$, -alkyl-$S(O)_2N(R_A)(R_B)$, -alkyl-$N(R_A)(R_B)$, -alkyl-$C(O)R_A$, -alkyl-$C(O)OR_A$, and -alkyl-$C(O)N(R_A)(R_B)$;

$R_A$ at each occurrence is independently hydrogen, alkyl, alkenyl or haloalkyl; and $R_B$ at each occurrence is independently hydrogen, alkyl, or haloalkyl.

DETAILED DESCRIPTION OF THE INVENTION

All references contained herein are fully incorporated by reference.

a) Definition of Terms

The term "acyl" as used herein, means $-C(O)CH_3$.

The term "alkenyl" as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" as used herein, means an alkyl group, as defined herein, appended to the parent molecular moiety through an oxygen atom. Representative examples of alkoxy include, but are not limited to, methoxy, ethoxy, propoxy, isopropoxy, butoxy, isobutoxy, tert-butoxy, pentyloxy, and hexyloxy.

The term "alkyl" as used herein, means a straight or branched chain hydrocarbon containing from 1 to 10 carbon atoms. Representative examples of alkyl include, but are not limited to, methyl, ethyl, n-propyl, isopropyl, n-butyl, sec-butyl, isobutyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "aryl" as used herein, means phenyl or a bicyclic aryl. The bicyclic aryl is naphthalenyl, or a phenyl fused to a monocyclic cycloalkyl, or a phenyl fused to a monocyclic cycloalkenyl. The phenyl and the bicyclic aryl groups of the present invention are unsubstituted or substituted. The bicyclic aryl is attached to the parent molecular moiety through any carbon atom contained within the bicyclic aryl. Representative examples of the aryl groups include, but are not limited to, dihydroindenyl, 2,3-dihydro-1H-inden-1-yl, naphthalenyl, dihydronaphthalenyl, and 1,2,3,4-tetrahydronaphthalen-1-yl.

The term "cycloalkyl" or "cycloalkane" as used herein, means a monocyclic or bicyclic cycloalkyl. The monocyclic cycloalkyl has three to eight carbon atoms, zero heteroatom and zero double bond. The monocyclic cycloalkyl can be attached to the parent molecular moiety through any substitutable atom contained within the monocyclic cycloalkyl. Examples of monocyclic cycloalkyls include, but are not limited to, cyclopropyl, cyclobutyl, cyclopentyl, cyclohexyl, cycloheptyl, and cyclooctyl. The bicyclic cycloalkyl is a monocyclic cycloalkyl fused to a monocyclic cycloalkyl. The bicyclic cycloalkyl can be attached to the parent molecular moiety through any substitutable atom contained within the bicyclic cycloalkyl. The monocyclic and bicyclic cycloalkyl groups of the present invention can be unsubstituted or substituted.

The term "cycloalkenyl" or "cycloalkene" as used herein, means a monocyclic or a bicyclic hydrocarbon ring system. The monocyclic cycloalkenyl has four-, five-, six-, seven- or eight carbon atoms and zero heteroatom. The four-membered ring systems have one double bond, the five-or six-membered ring systems have one or two double bonds, and the seven- or eight-membered ring systems have one, two or three double bonds. The monocyclic cycloalkenyl can be attached to the parent molecular moiety through any substitutable atom contained within the monocyclic cycloalkenyl. Representative examples of monocyclic cycloalkenyl groups include, but are not limited to, cyclobutenyl, cyclopentenyl, cyclohexenyl, cycloheptenyl and cyclooctenyl. The bicyclic cycloalkenyl is a monocyclic cycloalkenyl fused to a monocyclic cycloalkyl group, or a monocyclic cycloalkenyl fused to a monocyclic cycloalkenyl group. The bicyclic cycloalkenyl can be attached to the parent molecular moiety through any substitutable atom contained within the bicyclic cycloalkenyl. Representative examples of the bicyclic cycloalkenyl groups include, but are not limited to, 4,5,6,7-tetrahydro-3aH-indene, octahydronaphthalenyl and 1,6-dihydro-pentalene. The monocyclic and bicyclic cycloalkenyl groups of the present invention can be unsubstituted or substituted.

The term "halo" or "halogen" as used herein, means —Cl, —Br, —I or —F.

The term "haloalkoxy" as used herein, means an alkoxy group, as defined herein, in which one, two, three or four hydrogen atoms are replaced by halogen. Representative examples of haloalkoxy include, but are not limited to, chloromethoxy, 2-fluoroethoxy, trifluoromethoxy, 2-chloro-3-fluoropentyloxy, and pentafluoroethoxy.

The term "haloalkyl" as used herein, means an alkyl group, as defined herein, in which one, two, three, four, five or six hydrogen atoms are replaced by halogen. Representative examples of haloalkyl include, but are not limited to, chloromethyl, 2-fluoroethyl, trifluoromethyl, difluoromethyl, pentafluoroethyl, and 2-chloro-3-fluoropentyl.

The term "heterocycle" or "heterocyclic" as used herein, means a monocyclic heterocycle or a bicyclic heterocycle. The monocyclic heterocycle is a three-, four-, five-, six- or seven-membered ring containing at least one heteroatom independently selected from the group consisting of O, N, and S. The three- or four membered ring contains zero or one double bond, and one heteroatom selected from the group consisting of O, N and S. The five-membered ring contains zero or one double bond and one, two or three heteroatoms selected from the group consisting of O, N and S. The six-membered ring contains zero, one or two double bonds and one, two or three heteroatoms selected from the group consisting of O, N and S. The seven-membered ring contains zero, one, two, or three double bonds and one, two or three heteroatoms selected from the group consisting of O, N and S. The monocyclic heterocycle can be unsubstituted or substituted and is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, [1,4]diazepan-1-yl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydropyranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, a monocyclic heterocycle fused to a monocyclic heterocycle, or a monocyclic heterocycle fused to a monocyclic heteroaryl. The bicyclic heterocycle is connected to the parent molecular moiety through any carbon atom or any nitrogen atom contained within the bicyclic heterocycle and can be unsubstituted or substituted. Representative examples of bicyclic heterocycle include, but are not limited to, benzodioxinyl, benzopyranyl, thiochromanyl, 2,3-dihydroindolyl, indolizinyl, pyranopyridinyl, 1,2,3,4-tetrahydroisoquinolinyl, 1,2,3,4-tetrahydroquinolinyl, thiopyranopyridinyl, 2-oxo-1,3-benzoxazolyl, 3-oxobenzoxazinyl, 3-azabicyclo[3.2.0]heptyl, 3,6-diazabicyclo[3.2.0]heptyl, octahydrocyclopenta[c]pyrrolyl, hexahydro-1H-furo[3,4-c]pyrrolyl, octahydropyrrolo[3,4-c]pyrrolyl, 2,3-dihydrobenzofuran-7-yl, 2,3-dihydrobenzofuran-3-yl, and 3,4-dihydro-2H-chromen-4-yl. The monocyclic or bicyclic heterocycles as defined herein may have two of the non-adjacent carbon atoms connected by a heteroatom selected from nitrogen, oxygen or sulfur, or an alkylene bridge of between one and three additional carbon atoms. Representative examples of monocyclic or bicyclic heterocycles that contain such connection between two non-adjacent carbon atoms include, but are not limited to, 2-azabicyclo[2.2.2]octyl, 2-oxa-5-azabicyclo[2.2.2]octyl, 2,5-diazabicyclo[2.2.2]octyl, 2-azabicyclo[2.2.1]heptyl, 2-oxa-5-azabicyclo[2.2.1]heptyl, 2,5-diazabicyclo[2.2.1]heptyl, 2-azabicyclo[2.1.1]hexyl, 5-azabicyclo[2.1.1]hexyl, 3-azabicyclo[3.1.1]heptyl, 6-oxa-3-azabicyclo[3.1.1]heptyl, 8-azabicyclo[3.2.1]octyl, 3-oxa-8-azabicyclo[3.2.1]octyl, 1,4-diazabicyclo[3.2.2]nonyl, 1,4-diazatricyclo[4.3.1.1$^{3,8}$]undecyl, 3,10-diazabicyclo[4.3.1]decyl, or 8-oxa-3-azabicyclo[3.2.1]octyl, octahydro-1H-4,7-methanoisoindolyl, and octahydro-1H-4,7-epoxyisoindolyl. The nitrogen heteroatom may or may not be quaternized, and may or may not be oxidized to the N-oxide. In addition, the nitrogen containing heterocyclic rings may or may not be N-protected.

The term "heteroaryl" as used herein, means a monocyclic heteroaryl or a bicyclic heteroaryl. The monocyclic heteroaryl is a five- or six-membered ring. The five-membered ring consists of two double bonds, and one sulfur, nitrogen or oxygen atom. Alternatively, the five-membered ring has two double bonds, and one, two, three or four nitrogen atoms and optionally one additional heteroatom selected from oxygen or sulfur. The six-membered ring consists of three double bonds and one, two, three or four nitrogen atoms. The bicyclic heteroaryl consists of a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl. The monocyclic and the bicyclic heteroaryl are connected to the parent molecular moiety through any substitutable atom contained within the monocyclic or the bicyclic heteroaryl. The monocyclic and bicyclic heteroaryl groups of the present invention can be substituted or unsubstituted. In addition, the nitrogen heteroatom may or may not be quaternized, and may or may not be oxidized to the N-oxide. Also, the nitrogen containing rings may or may not be N-protected. Representative examples of monocyclic heteroaryl include, but are not limited to, furanyl, imidazolyl, isoxazolyl, isothiazolyl, oxadiazolyl, oxazolyl, pyridinyl, pyridine-N-oxide, pyridazinyl, pyrimidinyl, pyrazinyl, pyra-zolyl, pyrrolyl, tetrazolyl, thiadiazolyl, thiazolyl, thienyl, triazolyl, and triazinyl. Representative examples of bicyclic heteroaryl groups include, but not limited to, benzothienyl, benzoxazolyl, benzimidazolyl, benzoxadiazolyl, 6,7-dihydro-1,3-benzothiazolyl, imidazo[1,2-a]pyridinyl, indazolyl, 1H-indazol-3-yl, indolyl, isoindolyl, isoquinolinyl, naphthyridinyl, pyridoimidazolyl, quinolinyl, quinolin-8-yl, and 5,6,7,8-tetrahydroquinolin-5-yl.

The term "heteroatom" as used herein, refers to nitrogen, oxygen or sulfur atom.

b) Compounds, Methods and Compositions of the Invention

Compounds of the invention can have the formula (I) or (II) as described above. More particularly, compounds of formula (I) can include, but are not limited to, compounds wherein $R_1$ is hydrogen, alkyl, haloalkyl or —CN; $R_3$ is substituted phenyl; and $R_2$ is —N(H)—$(CR_uR_v)$-$R_{2a}$, wherein $R_{2a}$ is selected from (a) or (b)

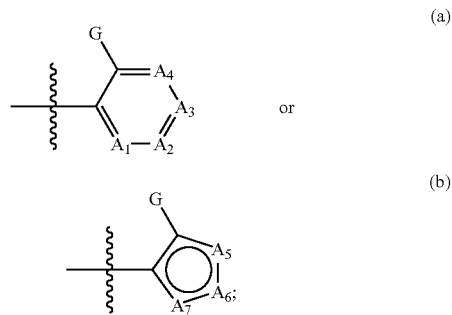

Preferred compounds are those in which $R_{2a}$ is a six-membered ring such as phenyl or pyridine and G is aryl or heteroaryl. Other preferred compounds are those in which $R_{2a}$ is phenyl or pyridine and G is -$L_2$-$W_2$. Preferred compounds are those in which $L_2$ is O and $W_2$ is aryl or heteroaryl. Other compounds of the present invention include those in which $R_{2a}$ is a five membered ring as defined above.

The present invention also comprises compounds of formula (I) in which $R_1$ is hydrogen, alkyl, haloalkyl or —CN; $R_3$ is substituted phenyl; and $R_2$ is —N(H)—$R_{2b}$, wherein $R_{2b}$ is selected from groups (c), (d) and (e)

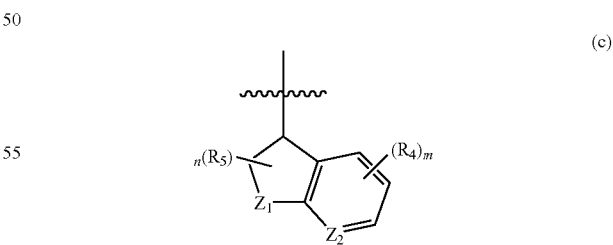

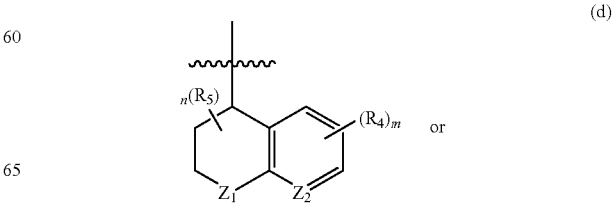

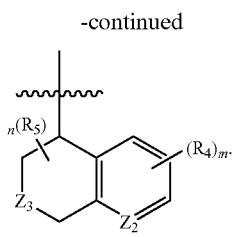
(e)

Other compounds of the present invention include those of formula (I) in which $R_1$ is hydrogen, alkyl, haloalkyl or —CN; $R_3$ is substituted phenyl; and $R_2$ is $R_{2b}$ wherein $R_{2b}$ is selected from groups (c), (d) and (e) depicted above.

The present invention also comprises compounds of formula (I) in which $R_1$ is hydrogen, alkyl, haloalkyl or —CN; $R_3$ is $R_{2b}$ selected from groups (c), (d) and (e) as depicted above; and $R_2$ is substituted phenyl. Preferred compounds are those in which $R_{2b}$ has formula (c) or (d).

The present invention also comprises compounds of formula (II) that can include, but are not limited to, compounds wherein $R_1$ is hydrogen, alkyl, haloalkyl or —CN; $R_3$ is substituted phenyl and $R_2$ is —N(H)—$(CR_uR_v)$—$R_{2a}$. Preferred compounds are those in which $R_{2a}$ is phenyl or pyridine, independently substituted with G, and G is an alkoxy group or hydrogen. Other preferred compounds include those in which G is -$W_2$ or -$L_2$-$W_2$; wherein -$L_2$ is preferably oxygen and $W_2$ is selected from aryl, heteroaryl or heterocycle; being independently unsubstituted or substituted. Other compounds of the present invention include those in which $R_{2a}$ is a carbocyclic or heterocyclic five-membered ring.

Other compounds of the present invention are those of formula (II) that can include, but are not limited to, compounds wherein $R_1$ is hydrogen, alkyl, haloalkyl or —CN; $R_3$ is substituted phenyl and $R_2$ is —N(H)—$R_{2b}$. Wherein —$R_{2b}$ is selected from the groups (c), (d) and (e) described above. Also included are compounds of formula (II) in which $R_1$ is hydrogen, alkyl, haloalkyl or —CN; $R_3$ is substituted phenyl and $R_2$ is —$R_{2b}$; wherein —$R_{2b}$ is selected from the groups (c), (d) and (e) described above. Other compounds included in the present invention are those having formula (II) wherein $R_1$ is hydrogen, alkyl, haloalkyl or —CN; $R_2$ is substituted phenyl and $R_3$ is $R_{2b}$; wherein —$R_{2b}$ is selected from the groups (c), (d) and (e) described above.

The invention also provides pharmaceutical compositions comprising a therapeutically effective amount of a compound of formula (I) or (II) in combination with a pharmaceutically acceptable carrier. The compositions comprise compounds of the invention formulated together with one or more non-toxic pharmaceutically acceptable carriers. The pharmaceutical compositions can be formulated for oral administration in solid or liquid form, for parenteral injection or for rectal administration.

The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of one skilled in the art of formulations.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration, including intravenous, intramuscular, intraperitoneal, intrasternal, subcutaneous, intraarticular injection and infusion.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate.

The term "pharmaceutically acceptable prodrug" or "prodrug," as used herein, represents those prodrugs of the compounds of the invention which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the invention can be rapidly transformed in vivo to a parent compound of formula (I), for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987).

The invention contemplates pharmaceutically active compounds either chemically synthesized or formed by in vivo biotransformation to compounds of formula (I).

Compounds and compositions of the invention are useful for modulating the activation of $P2X_7$ receptors. The compounds of the invention, including but not limited to those specified in the examples, possess an affinity for $P2X_7$ receptors, and block $P2X_7$ receptor activity. As $P2X_7$ receptor antagonists, the compounds of the invention can be useful for the treatment and prevention of a number of $P2X_7$ receptors -mediated diseases or conditions including but not limited to neuropathic pain, chronic inflammatory pain, inflammation and neurodegenerative conditions associated with several progressive CNS disorders, including, but not limited to, Alzheimer's disease, Parkinson's disease, depression, amyotrophic lateral sclerosis, Huntington's disease, dementia with Lewy bodies, multiple sclerosis as well as diminished CNS function resulting from traumatic brain injury.

The present invention also includes a method of use for inhibiting $P2X_7$ activity comprising administering to a patient in need of such treatment a therapeutically effective amount of a compound of formula (III), (IV) or (V) or a pharmaceutically acceptable salt, prodrug, salt of a prodrug, or a combination thereof. More particularly, methods of use administering compounds of formula (III) can include, but are not limited to methods using compounds wherein $R_6$ is hydrogen, alkyl, haloalkyl or —CN; $R_7$ is substituted phenyl; and $R_8$ is -W; wherein W is

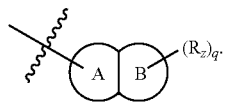

In a preferred embodiment A is a five or six membered monocyclic ring selected from the group consisting of cycloalkyl and heterocycle and is optionally substituted with 1, 2, or 3 substituents selected from the group consisting of alkyl, halo and haloalkyl; and B is phenyl or monocyclic heteroaryl, optionally substituted with 1, 2 or 3 substituents selected from the group consisting of halo, alkyl, —CN, —$OR_A$, —$SR_A$, —$N(R_A)(R_B)$ and haloalkyl; q is 0 or 1; and $R_z$ is $W_2$ or -$L_2$-$W_2$. Preferred methods are those using compounds in which A is a five or six membered monocyclic ring that is cycloalkyl which is optionally substituted with 1, 2, or 3 substituents selected from the group consisting of alkyl, halo and haloalkyl, and B is phenyl optionally substituted with 1, 2 or 3 substituents selected from the group consisting of halo, alkyl, —CN, —$OR_A$, —$SR_A$, —$N(R_A)(R_B)$ and haloalkyl. Another preferred method uses compounds in which A is a five or six membered monocyclic ring that is cycloalkyl which is optionally substituted with 1, 2, or 3 substituents selected from the group consisting of alkyl, halo and haloalkyl, and B is a pyridine group. Other methods included in the present invention are those using compounds of formula (III) in which $R_6$ is hydrogen, alkyl, haloalkyl or —CN; $R_7$ is substituted phenyl; and $R_8$ is —$C(R_xR_y)$-$W_1$. Preferred ones are those using compounds in which $W_1$ is phenyl, or a monocyclic heteroaryl. Other preferred methods use compounds wherein $W_1$ is optionally fused with a monocyclic, five or six-membered ring selected from the group consisting of phenyl, heteroaryl, heterocycle, cycloalkyl and cycloalkenyl.

Other methods comprised in the present invention include those using compounds of formula (III) wherein $R_6$ is hydrogen, alkyl, haloalkyl or —CN; $R_7$ is substituted phenyl and $R_8$ is selected from the group of —$C(R_xR_y)$-$W_1$-$W_2$ and —$C(R_xR_y)$-$W_1$-$L_2$-$W_2$.

Other methods included in the present invention include those using compounds of formula (III) in which $R_6$ is hydrogen, alkyl, haloalkyl or —CN; $R_8$ is substituted phenyl and $R_7$ is -W, wherein W is selected from any of the groups described above. Other methods that are part of the present invention include those using compounds of formula (III) wherein $R_6$ is hydrogen, alkyl, haloalkyl or —CN; $R_8$ is substituted phenyl and $R_7$ is selected from the group consisting of —N(H)-W, -$L_1$-$W_1$, -$L_1$-$W_1$-$W_2$, or -$L_1$-$W_1$-$L_2$-$W_2$. Preferred methods are those using compounds of formula (III) wherein $R_6$ is hydrogen, alkyl, haloalkyl or —CN; $R_8$ is substituted phenyl and $R_7$ is -$L_1$-$W_1$, wherein -$W_1$ is preferably phenyl or heteroaryl.

The present invention also includes methods of use as described above using compounds of formula (IV) wherein $R_6$ is hydrogen, alkyl, haloalkyl or —CN; $R_7$ is substituted phenyl; and $R_8$ is selected from the group consisting of -W, —$C(R_xR_y)$-$W_1$, —$C(R_xR_y)$-$W_1$-$W_2$, or —$C(R_xR_y)$-$W_1$-$L_2$-$W_2$. Preferred compounds to be used in these methods of use are those in which $R_8$ is -W, most preferably W is a five-membered ring fused to a phenyl group. Also preferred compounds include those in which $R_8$ is —$C(R_xR_y)$-$W_1$, and $W_1$ is phenyl.

Other methods of use contemplated in the present invention are those using compounds of formula (IV) in which $R_6$ is hydrogen, alkyl, haloalkyl or —CN; $R_8$ is substituted phenyl, and $R_7$ is -W. Preferred compounds are those in which W is a five-membered ring fused to a phenyl group. Also included are methods using compounds of formula (IV) in which $R_6$ is hydrogen, alkyl, haloalkyl or —CN; $R_8$ is substituted phenyl, and $R_7$ is -$L_1$-$W_1$. Preferred compounds used in this method of use are those in which $W_1$ is a phenyl, heteroaryl or heterocycle. Other methods of use contemplated in the present invention are those using compounds of formula (IV) in which $R_6$ is hydrogen, alkyl, haloalkyl or —CN; $R_8$ is substituted phenyl, and $R_7$ is -$L_1$-$W_1$-$W_2$. Preferred compounds in this group are those in which WI is heteroaryl and -$W_2$ is heterocycle. Other methods of use contemplated in the present invention are those using compounds of formula (IV) in which $R_6$ is hydrogen, alkyl, haloalkyl or —CN; $R_8$ is phenyl, and $R_7$ is -$L_1$-$W_1$-$L_2$-$W_2$. Preferred compounds to be used include those in which -$W_1$ is phenyl or heteroaryl, $L_2$ is oxygen and -$W_2$ is pyridine. Also included are methods using compounds of formula (IV) in which $R_6$ is hydrogen, alkyl, haloalkyl or —CN; $R_8$ is substituted phenyl, and $R_7$ is -$W_2$.

The present invention also includes methods of use as described above using compounds of formula (V), wherein $R_9$ is hydrogen, alkyl, haloalkyl or —CN; $R_{10}$ is phenyl; and $R_{11}$ is —$C(R_xR_y)$-$W_1$, preferably wherein Rx and Ry are hydrogen and $W_1$ is phenyl. The present invention also contemplates methods of use with compounds of formula (V) in which $R_9$ is hydrogen, alkyl, haloalkyl or —CN;

$R_{11}$ is substituted phenyl; and $R_{10}$ is —$C(R_xR_y)$-$W_1$ wherein $R_x$, $R_y$ and $W_1$. Also included are methods using compounds of formula (IV) in which $R_9$ is substituted phenyl; $R_{10}$ is —$C(R_xR_y)$-$W_1$; and $R_{11}$ is hydrogen, wherein $R_x$, preferably wherein Rx and Ry are hydrogen and $W_1$ is phenyl.

c) Preparation of the Compounds of the Invention

The compounds and processes of the present invention will be better understood in connection with the following synthetic schemes, which illustrate the methods by which the compounds of the invention may be prepared. Starting materials can be obtained from commercial sources or prepared by well-established literature methods known to those of ordinary skill in the art.

Scheme 1

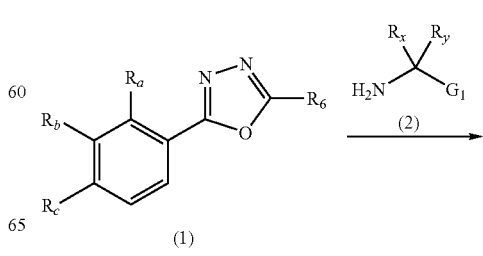

-continued

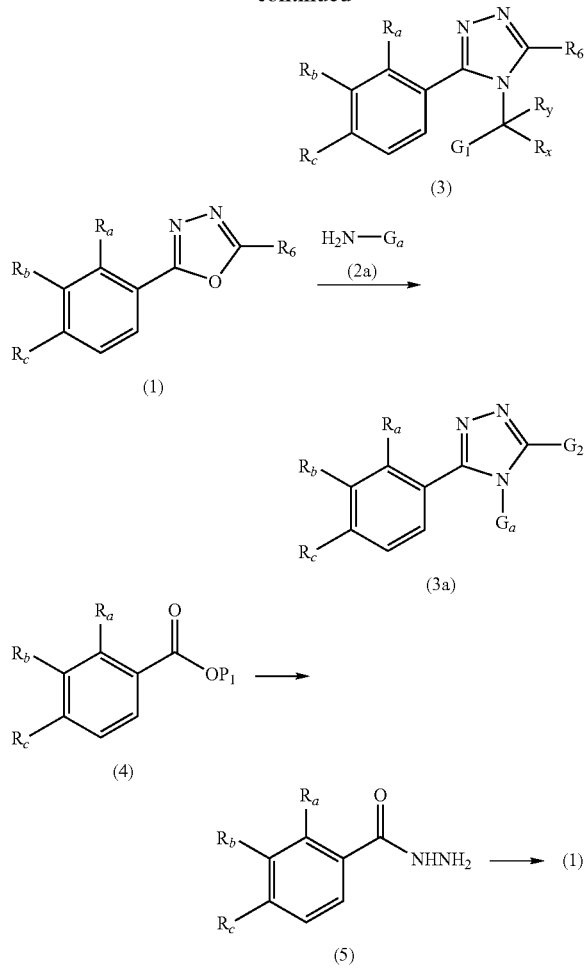

Triazoles of formula (3) wherein $G_1$ is $W_1$, $W_1$-$W_2$ or $W_1$-$L_2$-$W_2$ and $W_1$, $W_2$, $L_2$, $R_x$, $R_y$, $R_a$, $R_b$, $R_c$ and $R_6$ are as defined in formula (III), can be prepared by reacting amines of formula (2) with suitably substituted oxadiazoles of formula (1) at a temperature from about 100° C. to about 150° C. The reaction can be conducted optionally in a solvent such as, but not limited to, toluene, xylene, acetonitrile or ethanol.

Compounds of formula (3a) wherein $G_2$ is $R_1$ or $R_6$, $G_a$ is $R_{2b}$ or W and $R_{2b}$, W, $R_a$, $R_b$, $R_c$, $R_1$ and $R_6$ are as defined in formula (I) or (III) can be prepared from compounds of formula (1) and amines of formula (2a) using similar conditions for the conversion of compounds of formula (1) to (3).

Amines of formula (2a) are either commercially available or can be prepared using known methodologies. Literature references that outline synthesis of amines of formula (2a) include, but are not limited to, Kaluza et al *Chem. Ber.* 1955, 88, 597; Bennett et al *J. Chem. Soc.* 1931; 1692, Sagorewskii et al *J. Gen. Chem. USSR* 1964; 34, 2294, Pratap et al *Indian J. Chem. Sect. B* 1981; 20; 1063, WO2005/42533, p 121; Braun et al *Chem. Ber.* 1929, 62, 2420; Tikk et al *Acta Chim. Hung.* 1986, 121, 255; and Bernabeu et al *Synth. Commun.* 2004, 34, 137.

Oxadiazoles of formula (1) can be prepared in two steps from benzoic acid esters (either commercially available or made by known methodologies from corresponding benzoic acids) of formula (4) wherein $P_1$ is alkyl or benzyl. Reaction of the benzoic acid esters of formula (4) with hydrazine in a solvent such as but not limited to ethanol, at a temperature of about room temperature to about the reflux temperature of the solvent employed provides acyl hydrazides of formula (5). Reaction of acyl hydrazides of formula (5) with an orthoester such as triethylorthoformate affords oxadiazoles of formula (1). The conversion is effected in the presence of catalytic amount of p-toluenesulfonic acid in a solvent such as, but not limited to, toluene at the reflux temperature of the solvent used.

Scheme 1A

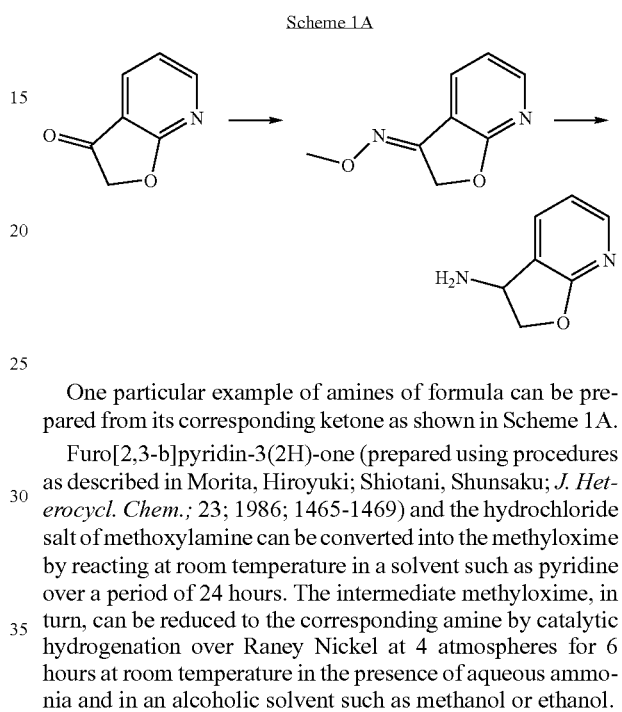

One particular example of amines of formula can be prepared from its corresponding ketone as shown in Scheme 1A.

Furo[2,3-b]pyridin-3(2H)-one (prepared using procedures as described in Morita, Hiroyuki; Shiotani, Shunsaku; *J. Heterocycl. Chem.;* 23; 1986; 1465-1469) and the hydrochloride salt of methoxylamine can be converted into the methyloxime by reacting at room temperature in a solvent such as pyridine over a period of 24 hours. The intermediate methyloxime, in turn, can be reduced to the corresponding amine by catalytic hydrogenation over Raney Nickel at 4 atmospheres for 6 hours at room temperature in the presence of aqueous ammonia and in an alcoholic solvent such as methanol or ethanol.

Scheme 1B

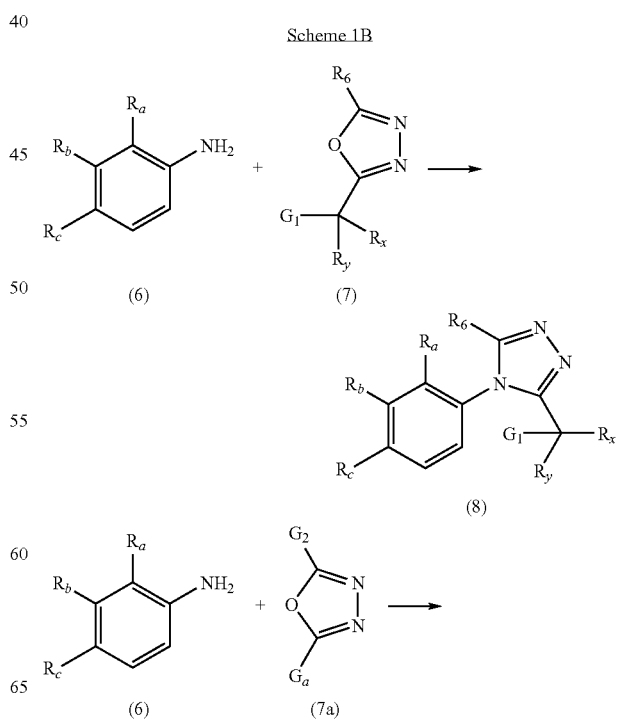

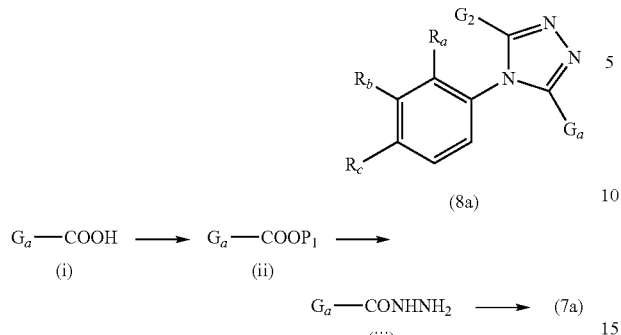

Similarly, triazoles of formula (8) wherein $G_1$ is $W_1$, $W_1$-$W_2$ or $W_1$-$L_2$-$W_2$ and $W_1$, $W_2$, $L_2$, $R_x$, $R_y$, $R_a$, $R_b$, $R_c$ and $R_6$ are as defined in formula (III), and compounds of formula (8a) wherein $G_2$ is $R_1$ or $R_6$, $G_a$ is $R_{2b}$ or W and $R_{2b}$, W, $R_a$, $R_b$, $R_c$, $R_1$ and $R_6$ are as defined in formula (I) or (III), can be obtained under similar reaction conditions as mentioned in Scheme 1 from amines of formula (6) and oxadiazoles of formula (7) or (7a) respectively.

Oxidazoles of formula (7a) can be prepared from carboxylic esters of formula (ii) (prepared from esterification of acids of formula (i) using similar reaction conditions for the synthesis of compounds of formula (1) from esters of formula (4) as shown in Scheme 1.

Acids of formula (i) can be purchased or prepared using various known methodologies. Literature references describing the synthesis of acids of formula (i) include, but are not limited to, Weidel *Monatsh. Chem.* 1882, 3, 66; Weidel *Monatsh. Chem.* 1881, 2, 29; Cohen et al *J. Pharm Sci.* 1987, 76, 848; Maiti et al *Synthesis* 1987, 9, 806; Belletaire et al *Synth. Commun.* 1982, 12, 763; Cohen et al *J. Pharm Sci.* 1987, 76, 848; Belletaire et al *Synth. Commun.* 1982, 12, 763; Fredga *Acta Chem. Scand.* 1955, 9, 719; Wolf *Helv. Chim. Acta* 1972, 55, 2919; Scapecchi et al *Farmaco* 1998, 53, 764; Bernabeu *Synth. Commun.* 2004, 34, 137; and U.S. Pat. No. 3,975,431.

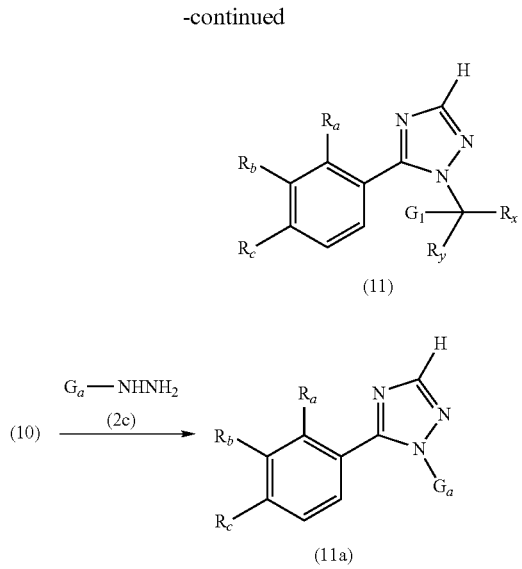

Triazoles of formula (11) wherein $G_1$ is $W_1$, $W_1$-$W_2$ or $W_1$-$L_2$-$W_2$ and $W_1$, $W_2$, $L_2$, $R_x$, $R_y$, $R_a$, $R_b$, and $R_c$ are as defined in formula (IV), can be prepared as outlined in Scheme 2. Benzamides of formula (9), purchased or prepared by known methodologies, and dimethylformamide dimethylacetal when heated neat at reflux provide acylamidines of formula (10). Compounds of formula (10) and hydrazines of formula (2b), in the presence of additives such as acetic acid and sodium acetate, can be heated in a solvent such as, but not limited to, dioxane to afford triazoles of formula (11).

Similarly, compounds of formula (11a) wherein $G_a$ is $R_{2b}$ or W, and W, $R_{2b}$, $R_a$, $R_b$, and $R_c$ are as defined in formula (II) or (IV) can be prepared from compounds of formula (10) and hydrazines of formula (2c). Hydrazines of formula (2c) can be synthesized using procedures described in literature references (for example, Sauter et al *Arch. Pharm.* 1981, 314, 567).

Scheme 2

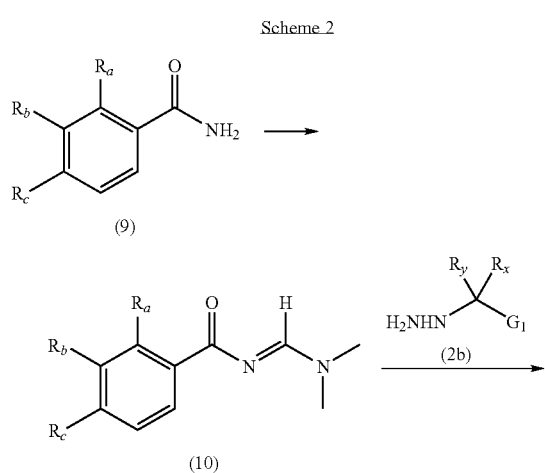

Scheme 3

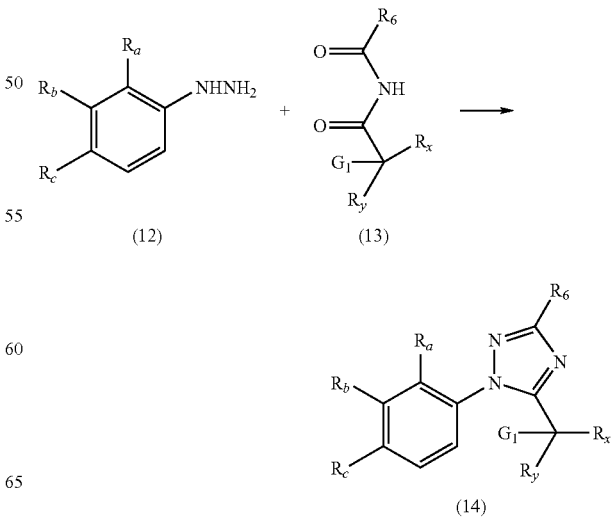

-continued

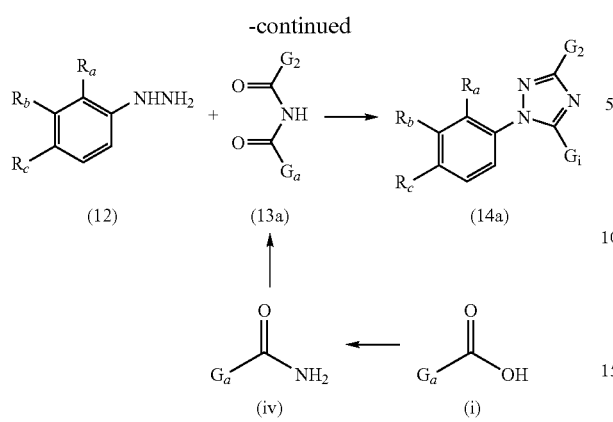

Triazoles of formula (14) wherein $G_1$ is $W_1$, $W_1$-$W_2$ or $W_1$-$L_2$-$W_2$ and $W_1$, $W_2$, $L_2$, $R_x$, $R_y$, $R_a$, $R_b$, $R_c$ and $R_6$ are as defined in formula (IV), or compounds of formula (14a) wherein $G_a$ is $R_{2b}$ or W, $G_2$ is $R_1$ or $R_6$ and W, $R_{2b}$, $R_a$, $R_b$, $R_c$, $R_1$, and $R_b$ are as defined in formula (II) or (IV), can be prepared using the chemistry outlined in Scheme 3. Substituted hydrazines of formula (12) can be reacted with compounds of formula (13) or (13a) respectively, in refluxing glacial acetic acid to provide the desired triazole product.

Compounds of formula (13) or (13a) can be prepared from the corresponding carboxylic acid by (a) reacting with isobutyl chloroformate in the presence of a base such as, but not limited to, diisopropylethylamine; (b) reacting the product of step (a) with ammonium hydroxide to provide amides such as those of formula (iv); and (c) acylation of amides from step (b) with acid chlorides of formula $G_2C(O)Cl$, in the presence of a base such as, but not limited to, sodium hydride provides compounds of formula (13) and (13a) respectively.

Alternatively, amides obtained from step (b) can be formylated by reacting with N,N,-dimethylformamide dimethylacetal at elevated temperature (for example, at about 100° C. to about 130° C.), followed by stirring in an acid such as acetic acid at about 0° C. to about room temperature, to provide compounds of formula (13) and (13a) respectively wherein $R_6$ and $G_2$ are hydrogen.

Scheme 4

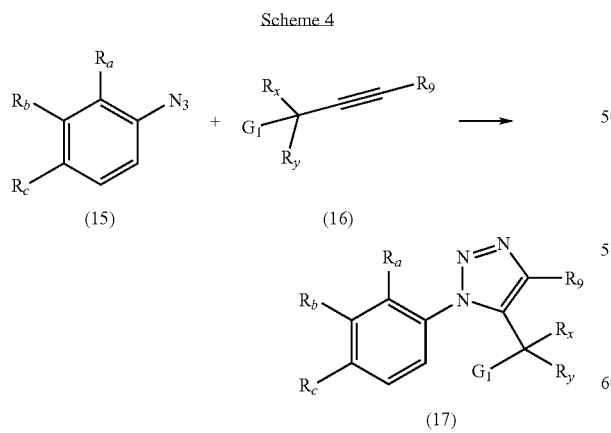

Triazoles of formula (17) wherein $G_1$ is $W_1$, $W_1$-$W_2$ or $W_1$-$L_2$-$W_2$ and $W_1$, $W_2$, $L_2$, $R_x$, $R_y$, $R_a$, $R_b$, $R_c$ and $R_9$ are as defined in formula (V) can be prepared from the reaction of azides of formula (15) with acetylenes of formula (16), in the presence of a solvent such as, but not limited to, toluene. The transformation is generally performed at the reflux temperature of the solvent employed.

Scheme 5

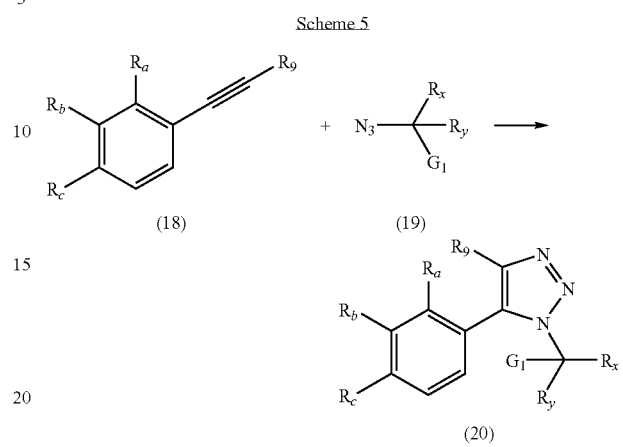

Triazoles of formula (20) wherein $G_1$ is $W_1$, $W_1$-$W_2$ or $W_1$-$L_2$-$W_2$ and $W_1$, $W_2$, $L_2$, $R_x$, $R_y$, $R_a$, $R_b$, $R_c$ and $R_9$ are as defined in formula (V) can be prepared from azides of formula (18) and acetylenes of formula (19). The conversion is generally conducted by heating the mixtures in a solvent such as, but not limited to, ethanol at reflux to provide a mixture of triazole regioisomers, from which the triazoles of formula (20) can be isolated by chromatography.

Scheme 6

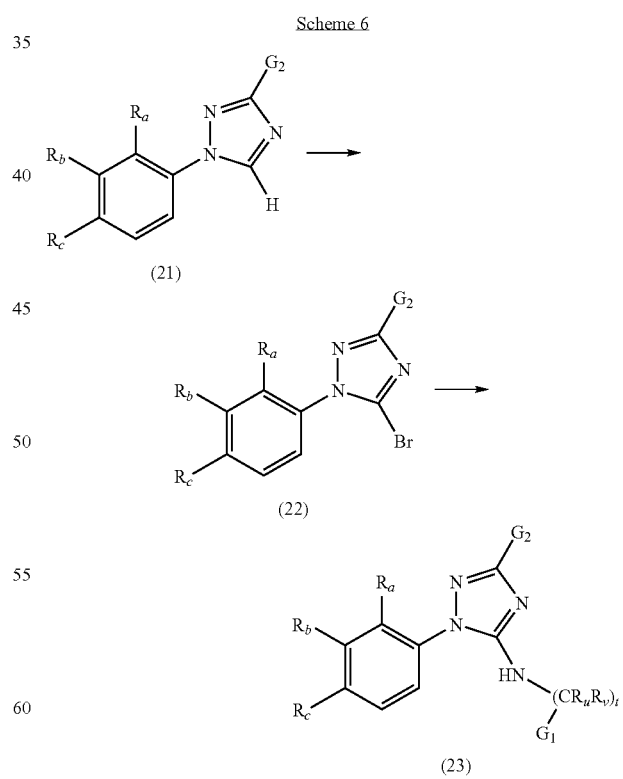

Triazoles of formula (23) wherein $G_1$ is $R_{2a}$, $W_1$, $W_1$-$W_2$ or $W_1$-$L_2$-$W_2$ when t is 1 or 2, or $G_1$ is $R_{2b}$ when t is 0, and $G_2$ is $R_1$ or $R_6$, wherein $R_{2a}$, $R_{2b}$, $W_1$, $W_2$, $L_2$, $R_a$, $R_b$, $R_c$, $R_1$, $R_6$, $R_u$ and $R_v$ are as defined in formula (II) or (IV), can be prepared using the chemistry outlined in Scheme 6. Triazoles of formula (21) can be brominated using N-bromosuccinimide in the presence of a catalytic amount of benzoyl peroxide in a refluxing solvent such as carbon tetrachloride. The resultant bromotriazoles of formula (22) can be reacted with amines of formula $G_1$-$(CR_uR_v)_t$—$NH_2$, either neat at 100-150° C. or in solvents such as toluene, xylene, acetonitrile or ethanol at reflux.

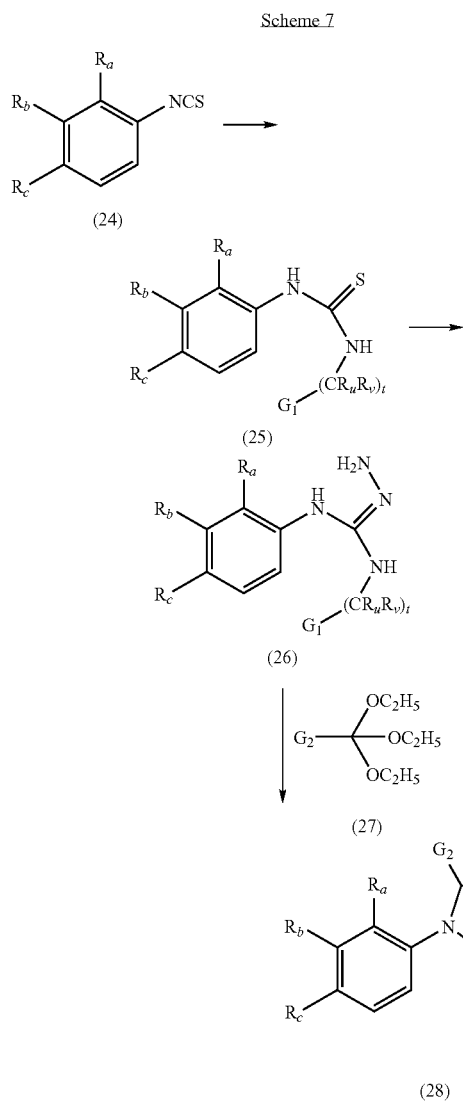

Triazoles of formula (28) wherein $G_1$ is $R_{2a}$, $W_1$, $W_1$-$W_2$ or $W_1$-$L_2$-$W_2$ when t is 1 or 2, or $G_1$ is $R_{2b}$ when t is 0, and $G_2$ is $R_1$ or $R_6$, wherein $W_1$, $W_2$, $L_2$, $R_{2a}$, $R_{2b}$, $R_a$, $R_b$, $R_c$, $R_1$, $R_6$, $R_u$ and $R_v$ are as defined in formula (I) or (III), can be prepared using the chemistry outlined in Scheme 7. Isothiocyanates of formula (24) and amines of formula $G_1$-$(CR_uR_v)_t$—$NH_2$ can be reacted in a solvent such as, but not limited to, tetrahydrofuran, with or without heating to provide thioureas of formula (25). The thioureas of formula (25) can be converted to compounds of formula (26) by reacting with hydrazine in a solvent such as, but not limited to, tetrahydrofuran in the presence of a base such as triethylamine and a mercury salt such as mercuric chloride. The reaction can be accomplished either at room temperature or at elevated temperature. Triazoles of formula (28) can be synthesized from compounds of formula (26) by reacting with orthoesters of formula (27) (for example, triethylorthoformate and the like) in the presence of an acid catalyst such as, but not limited to, formic acid. The reaction can be effected with heating to reflux in a solvent such as, but not limited to, tetrahydrofuran.

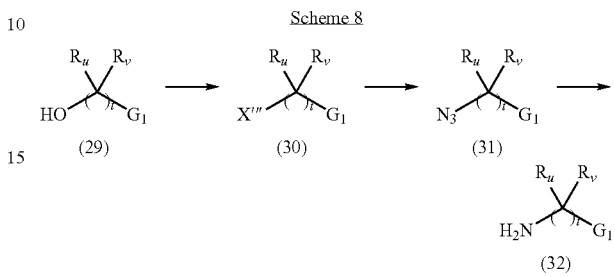

Azides of formula (31) and amines of formula (32) wherein $G_1$ is $R_{2a}$, $W_1$, $W_1$-$W_2$ or $W_1$-$L_2$-$W_2$, when t is 1 or 2, or $G_1$ is $R_{2b}$ when t is 0, and wherein $W_1$, $W_2$, $L_2$, $R_u$, $R_v$, $R_{2a}$ and $R_{2b}$ are as defined in formula (I)-(V), can be prepared by a variety of methods known to one skilled in the art. One example of such preparations is outlined in Scheme 8. Alcohols of formula (29) can be reacted with neat thionyl chloride, with or without a solvent at about room temperature to provide chlorides of formula (30) wherein X''' is Cl. Examples of solvents used are, but not limited to, dichloromethane and chloroform. Alternatively, compounds of formula (31) wherein X''' is methyl sulfonate (mesylate) can be prepared from alcohols of formula (29) with methane sulfonyl chloride, in the presence of a base such as, but not limited to, triethylamine.

Displacement of chlorides or mesylates of formula (30) with sodium azide in a solvent such as, but not limited to, N,N-dimethylformamide or acetone, provides azides of formula (30), which can be reduced to amines of formula (32) in the presence of a reducing agent such as, but not limited to, palladium/carbon or $PtO_2$/carbon. The reaction can be performed in a solvent such as, but not limited to, ethanol, methanol or ethyl acetate at about room temperature.

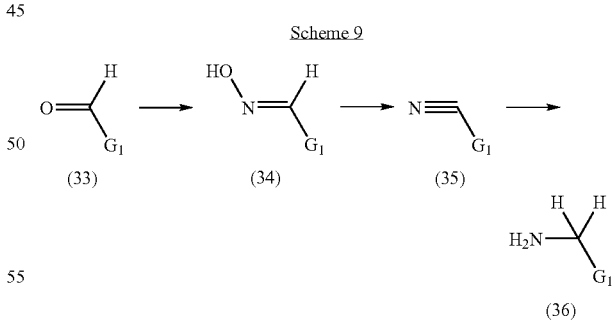

Amines of formula (36) wherein $G_1$ is $R_{2a}$, $W_1$, $W_1$-$W_2$ or $W_1$-$L_2$-$W_2$, and $R_{2a}$, $W_1$, $W_2$, and $L_2$ are as defined in formula (I)-(V), can be prepared from the corresponding aldehydes of formula (33) as depicted in Scheme 9. Reaction of the aldehydes of formula (33) with hydroxylamine hydrochloride in an alcoholic solvent such as, but not limited to, ethanol, provides oximes of formula (34). Oximes of formula (34) can be converted to nitriles of formula (35) in the presence of acetic anhydride and a base such as, but not limited to, potassium hydroxide or sodium hydroxide. Reduction of the nitrites of formula (35) with Raney/nickel and ammonia provides amines of formula (36). The reduction can be performed in an alcoholic solvent such as, but not limited to, methanol.

Certain nitrites of formula (35) can be purchased (for example 2-amino nicotinonitrile) or prepared using procedures described in literature reference such as, but not limited to, Almed et al, *Indian Chem. Soc.,* 1996, 73, 141.

Nitriles of formula (35) can be prepared from the reaction of the corresponding bromides with zinc cyanide in the presence of a palladium catalyst, such as but not limited to, bis(triphenylphospine)palladium (II) chloride and in a solvent such as N,N-dimethylformamide.

Scheme 10

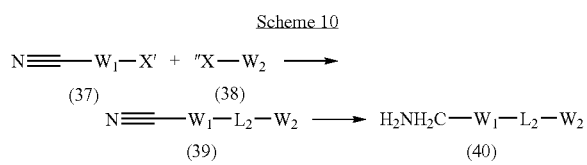

Compounds of formula (39) wherein $L_2$ is O, N(H) or N(alkyl) and $W_1$ and $W_2$ are as defined in formula (I)-(V) can be prepared by reaction of nitrites of formula (37) wherein X' is OH, $NH_2$ or N(H)(alkyl) with halides of formula (38) wherein X" is fluoro or chloro, in the presence of a base such as, but not limited to, sodium hydride or potassium carbonate. The reaction can be conducted in a solvent such as tetrahydrofuruan, dimethylformamide or dioxane at a temperature from about room temperature to about 150° C.

Conversely, compounds of formula (39) wherein $L_2$ is O, N(H) or N(alkyl) and $W_1$, and $W_2$ are as defined in formula (I)-(V) can also be prepared by reaction of nitrites of formula (37) wherein X' is fluoro and compounds of formula (38) wherein X" is —$NH_2$, —N(H)(alkyl), or OH under the abovementioned conditions.

Amines of formula (40) can be prepared from nitrites of formula (39) using the transformation conditions for the conversion of compounds of formula (35) to (36) as outlined in Scheme 9.

Scheme 11

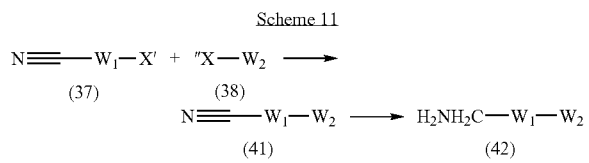

Nitriles of formula (41) wherein $W_1$ and $W_2$ are as defined in formula (I)-(V), can be prepared by reaction of nitrites of formula (37) wherein X' is Cl, Br, I or triflate with boronic acid or ester of formula (38) wherein X" is —$B(OR_{101})_2$ and $R_{101}$ is hydrogen or alkyl, in the presence of a palladium catalyst, such as but not limited to, bis(triphenylphospine)palladium (II) chloride and a base such as triethylamine or sodium carbonate. The reaction can be effected by heating from 50-90° C. in solvents such as isopropanol, ethanol, dimethoxyethane, water or dioxane. Alternatively, this transformation can be accomplished by reacting nitrites of formula (37) wherein X' is Cl, Br, I or triflate with tin reagents of formula (38) wherein X" is —$Sn(alkyl)_3$, with a palladium catalyst such as, but not limited to, tetrakis(triphenylphospine)palladium (0), and cesium fluoride and heating in a solvent such as dioxane. These transformations can also be effected by heating in a microwave reactor.

The transformation can also be accomplished by reacting compounds of formula (38) wherein X" is Cl, Br, I or triflate with compounds of formula (37) wherein X' is —$Sn(alkyl)_3$ or —$B(OR_{101})_2$ and $R_{101}$ is hydrogen or alkyl using the abovementioned reaction conditions.

Amines of formula (42) can be obtained from nitrites of formula (41) using the transformation conditions for the conversion of compounds of formula (35) to (36) as outlined in Scheme 9.

Scheme 12

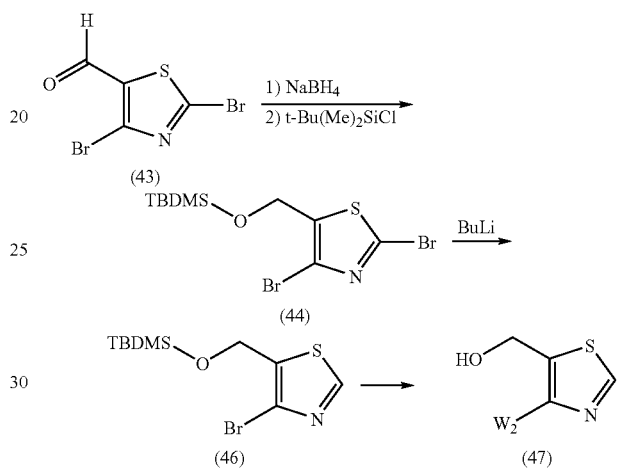

Alcohols of formula (29) can be prepared by various methodologies known to one skilled in the art. One such method is shown in Scheme 12.

The aldehyde of formula (43) can be reduced with sodium borohydride then protected as the t-butyldimethylsilyl ether, followed by mono-debromination with n-butyl lithium. The mono-bromothiazole of formula (46) can then be reacted with compounds of formula (38) wherein X" is —$Sn(alkyl)_3$ or —$B(OR_{101})_2$ and $R_{101}$ is hydrogen or alkyl using the reaction conditions outlined in Scheme 11, followed by removal of the t-butyldimethyl silyl group using reaction conditions known to one skilled in the art, to provide compounds of formula (47).

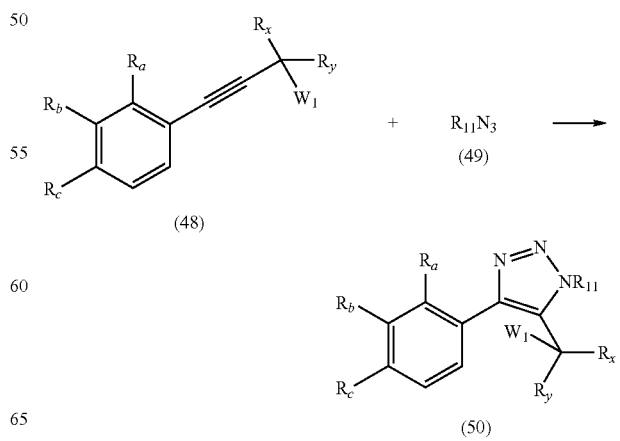

Triazoles of formula (50) wherein $R_a$, $R_b$, $R_c$, $R_{11}$, $R_x$, $R_y$ and $W_1$ are as defined in formula (V) can be prepared from substituted acetylenes of formula (48) and azide reagents of formula (49) (for example, trimethylsilylazide, methylazide, ethylazide and the like). The reaction is generally conducted with or without a solvent such as, but not limited to, dioxane, toluene or xylene, at a temperature from about 100° C. to about 150° C.

Scheme 14

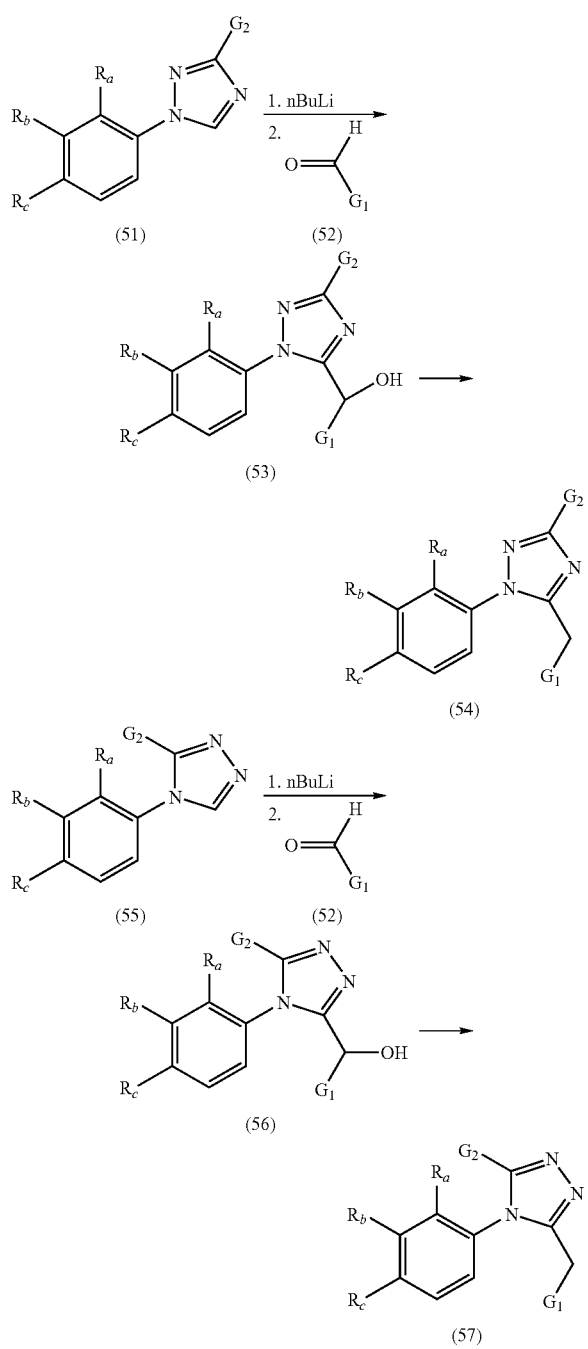

Triazoles of formula (54) wherein $G_2$ is $R_1$ or $R_6$ and $G_1$ is $W_1$, $W_1$-$W_2$ or $W_1$-$L_2$-$W_2$, and $R_1$, $R_6$, $W_1$, $W_2$, $L_2$, $R_a$, $R_b$ and $R_c$ are as defined in formula (II) or (IV) can be prepared using the chemistry shown in Scheme 14. Triazoles of formula (51) can be lithiated with alkyllithium reagents like n-butyl lithium, sec-butyl lithium or tert-butyl lithium in solvents such as tetrahydrofuran or diethylether at temperatures from −100° C. to about room temperature, followed by addition of aldehydes of formula (52) to provide alcohols of formula (53). The alcohol can then be converted to an intermediate thiocarbonate using phenyl chlorothionoformate and a catalyst such as 4-(dimethylamino)pyridine, in a solvent such as acetonitrile followed by radical deoxygenation with a tin reagent such as tributyltinhydride with AIBN in a solvent such as toluene to provide triazoles of formula (54).

Similarly, triazoles of formula (57) wherein $G_2$ is $R_1$ or $R_6$ and $G_1$ is $W_1$, $W_1$-$W_2$ or $W_1$-$L_2$-$W_2$, and $R_1$, $R_6$, $W_1$, $W_2$, $L_2$, $R_a$, $R_b$ and $R_c$ are as defined in formula (I) or (III) can be prepared from triazoles of formula (55).

D) REFERENCE EXAMPLES

The following Examples are intended as an illustration of and not a limitation upon the scope of the invention as defined in the appended claims.

Example 1

4-benzyl-3-(2,3-dichlorophenyl)-4H-1,2,4-triazole

Example 1A 5-(2,3-dichlorophenyl)-1H-tetrazole

A 2.0 M solution of Al(CH$_3$)$_3$ in toluene (35 mL) was treated with 2,3-dichlorobenzonitrile (8.00 g, 37.2 mmol), azidotrimethylsilane (5.14 g, 44.6 mmol) slowly, and heated at 80° C. for 16 hours behind a blast shield. The mixture was cooled to 0° C. and treated with 2N HCl (100 mL) dropwise over 1 hour. The mixture was allowed to warm to ambient temperature and extracted twice with ethyl acetate (100 mL). The combined organic phases were dried over Na$_2$SO$_4$, filtered through a ½" pad of silica gel, and the filtrate was evaporated under reduced pressure. The residue was purified by recrystallization from ethyl acetate/hexanes to provide the title compound. MS (DCI/NH$_3$) m/z 215 (M)$^+$; $^1$H NMR (DMSO-d$_6$) δ 7.59 (t, 1H, J=8.0 Hz), 7.79 (dd, 1H, J=7.8, 1.7 Hz), 7.92 (dd, 1H, J=8.1, 1.7 Hz).

Example 1B ethyl 5-(2,3-dichlorophenyl)-1,3,4-oxadiazole-2-carboxylate

Example 1A (6.45 g, 30.0 mmol) and ethyl chlorooxoacetate (3.4 mL, 30.4 mmol) in toluene (150 mL) were heated at reflux for 2 hours, cooled, the solvent was evaporated, and the crude material was recrystallized from ethanol to provide the title compound. MS (DCI/NH$_3$) m/z 287 (M+H)$^+$; $^1$H NMR (CDCl$_3$) δ 1.49 (t, 3H), 4.57 (q, 2H), 7.40 (t, 1H), 7.72 (dd, 1H), 7.96 (dd, 1H).

Example 1C 2-(2,3-dichlorophenyl)-1,3,4-oxadiazole

Example 1B (5.75 g, 20.0 mmol) and potassium hydroxide (1.2 g, 20.7 mmol) were combined in ethanol (200 mL) and heated at reflux for 2 hours. The mixture was allowed to cool to room temperature, acidified with 1N hydrochloric acid (50 mL), concentrated under reduced pressure, and the residue was partitioned between methylene chloride and water. The organic phase was dried with sodium sulfate, filtered, and the filtrate was concentrated under reduced pressure. The residue was purified by chromatography over silica gel, eluting with hexanes/ethyl acetate (2:1). MS (DCI/NH$_3$) m/z 215 (M+H)$^+$; $^1$H NMR (CDCl$_3$) δ 7.37 (t, 1H), 7.69 (dd, 1H), 7.90 (dd, 1H), 8.58 (s, 1H).

Example 1D 4-benzyl-3-(2,3-dichlorophenyl)-4H-1,2,4-triazole

Example 1C (216 mg, 1.01 mmol) and benzylamine (0.13 mL, 1.2 mmol) were heated in xylenes (0.25 mL) at 140° C. in a sealed tube for 72 hours. The mixture was allowed to cool to room temperature and was concentrated under reduced pressure. The residue was purified by preparative HPLC on a Waters Symmetry C8 column (40mm X 100 mm, 7 um particle size) using a gradient of 10% to 100% acetonitrile:0.1% aqueous trifluoroacetic acid over 12 minutes (15 minute run time) at a flow rate of 70 mL/minute to provide the title compound. MS (DCI/NH$_3$) m/z 304 (M+H)$^+$; $^1$H NMR (CDCl$_3$) δ 5.00 (s, 2H), 7.01 (m, 2H), 7.24-7.34 (m, 5H), 7.63 (m, 1H), 8.22 (s, 1H). Anal calcd for C$_{15}$H$_{11}$Cl$_2$N$_3$: C, 59.23; H, 3.65; N, 13.81. Found: C, 58.93; H, 3.41; N, 13.64.

Example 2

3-(2,3-dichlorophenyl)-4-[3-fluoro-5-(trifluoromethyl)benzyl]-4H-1,2,4-triazole

The title compound was prepared using the procedure as described in Example 1D substituting 3-fluoro-5-(trifluoromethyl)benzylamine for benzylamine. The residue was purified by preparative HPLC on a Waters Symmetry C8 column (25 mm×100 mm, 7 um particle size) using a gradient of 10% to 100% acetonitrile:0. 1% aqueous trifluoroacetic acid over 8 minutes (10 minute run time) at a flow rate of 40 mL/minute. MS (ESI) m/z 390 (M+H)$^+$; $^1$H NMR (DMSO-d$_6$) δ 5.26 (s, 2H), 7.09 (s, 1H), 7.18 (d, 1H), 7.41 (dd, 1H), 7.46 (t, 1H), 7.59 (d, 1H), 7.82 (dd, 1H), 8.88 (s, 1H).

Example 3

3-(2,3-dichlorophenyl)-4-[4-(trifluoromethoxy)benzyl]-4H-1,2,4-triazole

The title compound was prepared using the procedure as described in Example 1D substituting 4-(trifluoromethoxy)benzylamine for benzylamine. The residue was purified by preparative HPLC on a Waters Symmetry C8 column (25 mm×100 mm, 7 um particle size) using a gradient of 10% to 100% acetonitrile:0.1% aqueous trifluoroacetic acid over 8 minutes (10 minute run time) at a flow rate of 40 mL/minute. MS (ESI) m/z 388 (M+H)$^+$; $^1$H NMR (DMSO-d$_6$) δ 5.17 (s, 2H), 7.06 (d, 2H), 7.23 (d, 2H), 7.38 (d, 1H), 7.44 (t, 1H), 7.82 (d, 1H), 8.84 (s, 1H).

Example 4

3-(2,3-dichlorophenyl)-4-[3-(trifluoromethyl)benzyl]-4H-1,2,4-triazole

The title compound was prepared using the procedure as described in Example 1D substituting 3-(trifluoromethyl)benzylamine for benzylamine. The residue was purified by preparative HPLC on a Waters Symmetry C8 column (25 mm×100 mm, 7 μm particle size) using a gradient of 10% to 100% acetonitrile:0.1% aqueous trifluoroacetic acid over 8 minutes (10 minute run time) at a flow rate of 40 mL/minute. MS (ESI) m/z 372 (M+H)$^+$; $^1$H NMR (DMSO-d$_6$) δ 5.25 (s, 2H), 7.21 (s, 1H), 7.28 (d, 1H), 7.37 (dd, 1H), 7.44 (t, 1H), 7.49 (t, 1H), 7.61 (d, 1H), 7.81 (dd, 1H), 8.78 (s, 1H).

Example 5

3-(2,3-dichlorophenyl)-4-[4-(trifluoromethyl)benzyl]-4H-1,2,4-triazole

The title compound was prepared using the procedure as described in Example 1D substituting 4-(trifluoromethyl)benzylamine for benzylamine. The residue was purified by preparative HPLC on a Waters Symmetry C8 column (25 mm×100 mm, 7 μm particle size) using a gradient of 10% to 100% acetonitrile:0.1% aqueous trifluoroacetic acid over 8 minutes (10 minute run time) at a flow rate of 40 mL/minute. MS (ESI) m/z 372 (M+H)$^+$; $^1$H NMR (DMSO-d$_6$) δ 5.25 (s, 2H), 7.16 (d, 2H), 7.39 (dd, 1H), 7.44 (t, 1H), 7.61 (d, 2H), 7.82 (dd, 1H), 8.86 (s, 1H).

Example 6

3-(2,3-dichlorophenyl)-4-[3-(trifluoromethoxy)benzyl]-4H-1,2,4-triazole

The title compound was prepared using the procedure as described in Example 1D substituting 3-(trifluoromethoxy)benzylamine for benzylamine. The residue was purified by preparative HPLC on a Waters Symmetry C8 column (25 mm×100 mm, 7 μm particle size) using a gradient of 10% to 100% acetonitrile:0.1% aqueous trifluoroacetic acid over 8 minutes (10 minute run time) at a flow rate of 40 mL/minute. MS (ESI) m/z 388 (M+H)$^+$; $^1$H NMR (DMSO-d$_6$) δ 5.20 (s, 2H), 6.93 (s, 1H), 6.97 (d, 1H), 7.25 (d, 1H), 7.38 (m, 2H), 7.44 (t, 1H), 7.82 (dd, 1H), 8.87 (s, 1H).

Example 7

4-(4-tert-butylbenzyl)-3-(2,3-dichlorophenyl)-4H-1,2,4-triazole

The title compound was prepared using the procedure as described in Example 1D substituting 4-(tert-butyl)benzylamine for benzylamine. The residue was purified by preparative HPLC on a Waters Symmetry C8 column (25 mm×100 mm, 7 μm particle size) using a gradient of 10% to 100% acetonitrile:0.1% aqueous trifluoroacetic acid over 8 minutes (10 minute run time) at a flow rate of 40 mL/minute. MS (ESI) m/z 360 (M+H)$^+$; $^1$H NMR (DMSO-d$_6$) δ 1.22 (s, 9H), 5.07 (s, 2H), 6.86 (d, 2H), 7.24 (d, 2H), 7.39 (dd, 1H), 7.46 (t, 1H), 7.82 (dd, 1H), 8.81 (s, 1H).

Example 8

3-(2,3-dichlorophenyl)-4-(2,3-dimethylbenzyl)-4H-1,2,4-triazole

The title compound was prepared using the procedure as described in Example 1D substituting 2,3-dimethylbenzylamine for benzylamine. The residue was purified by preparative HPLC on a Waters Symmetry C8 column (25 mm×100 mm, 7 μm particle size) using a gradient of 10% to 100% acetonitrile:0.1% aqueous trifluoroacetic acid over 8 minutes (10 minute run time) at a flow rate of 40 mL/minute. MS (ESI) m/z 332 (M+H)+; 1H NMR (DMSO-d6) δ 1.92 (s, 3H), 2.16 (s, 3H), 5.15 (s, 2H), 6.54 (d, 1H), 6.90 (t, 1H), 7.05 (d, 1H), 7.37 (dd, 1H), 7.42 (t, 1H), 7.79 (dd, 1H), 8.66 (s, 1H).

Example 9

3-(2,3-dichlorophenyl)-4-(2,5-dimethylbenzyl)-4H-1,2,4-triazole

The title compound was prepared using the procedure as described in Example 1D substituting 2,5-dimethylbenzylamine for benzylamine. The residue was purified by preparative HPLC on a Waters Symmetry C8 column (25 mm×100 mm, 7 μm particle size) using a gradient of 10% to 100% acetonitrile:0.1% aqueous trifluoroacetic acid over 8 minutes (10 minute run time) at a flow rate of 40 mL/minute. MS (ESI) m/z 332 (M+H)+; 1H NMR (DMSO-d6) δ 1.98 (s, 3H), 2.09 (s, 3H), 5.11 (s, 2H), 6.41 (s, 1H), 6.95 (m, 2H), 7.35 (d, 1H), 7.41 (t, 1H), 7.79 (dd, 1H), 8.73 (s, 1H).

Example 10

3-(2,3-dichlorophenyl)-4-(3,4-dimethylbenzyl)-4H-1,2,4-triazole

The title compound was prepared using the procedure as described in Example 1D substituting 3,4-dimethylbenzylamine for benzylamine. The residue was purified by preparative HPLC on a Waters Symmetry C8 column (25 mm×100 mm, 7 μm particle size) using a gradient of 10% to 100% acetonitrile:0.1% aqueous trifluoroacetic acid over 8 minutes (10 minute run time) at a flow rate of 40 mL/minute. MS (ESI) m/z 332 (M+H)+; 1H NMR (DMSO-d6) δ 2.09 (s, 3H), 2.14 (s, 3H), 5.02 (s, 2H), 6.67 (m, 2H), 6.99 (d, 1H), 7.38 (d, 1H), 7.47 (t, 1H), 7.84 (d, 1H), 8.80 (s, 1H).

Example 11

3-(2,3-dichlorophenyl)-4-(3,5-dimethylbenzyl)-4H-1,2,4-triazole

The title compound was prepared using the procedure as described in Example 1D substituting 3,5-dimethylbenzylamine for benzylamine. The residue was purified by preparative HPLC on a Waters Symmetry C8 column (25 mm×100 mm, 7 μm particle size) using a gradient of 10% to 100% acetonitrile:0.1% aqueous trifluoroacetic acid over 8 minutes (10 minute run time) at a flow rate of 40 mL/minute. MS (ESI) m/z 332 (M+H)+; 1H NMR (DMSO-d6) δ 2.14 (s, 3H), 2.50 (s, 3H), 5.02 (s, 2H), 6.49 (s, 2H), 6.86 (s, 1H), 7.38 (d, 1H), 7.47 (t, 1H), 7.84 (d, 1H), 8.80 (s, 1H).

Example 12

3-(2,3-dichlorophenyl)-4-(2,3-dimethoxybenzal)-4H-1,2,4-triazole

The title compound was prepared using the procedure as described in Example 1D substituting 2,3-dimethoxybenzylamine for benzylamine. The residue was purified by preparative HPLC on a Waters Symmetry C8 column (25 mm×100 mm, 7 μm particle size) using a gradient of 10% to 100% acetonitrile:0.1% aqueous trifluoroacetic acid over 8 minutes (10 minute run time) at a flow rate of 40 mL/minute. MS (ESI) m/z 364 (M+H)+; 1H NMR (DMSO-d6) δ 3.47 (s, 3H), 3.75 (s, 3H), 5.05 (s, 2H), 6.35 (d, 1H), 6.90 (t, 1H), 6.98 (dd, 1H), 7.38 (dd, 1H), 7.46 (t, 1H), 7.83 (dd, 1H), 8.68 (s, 1H).

Example 13

3-(2,3-dichlorophenyl)-4-(2,5-dimethoxybenzyl)-4H-1,2,4-triazole

The title compound was prepared using the procedure as described in Example 1D substituting 2,5-dimethoxybenzylamine for benzylamine. The residue was purified by preparative HPLC on a Waters Symmetry C8 column (25 mm×100 mm, 7 μm particle size) using a gradient of 10% to 100% acetonitrile:0.1% aqueous trifluoroacetic acid over 8 minutes (10 minute run time) at a flow rate of 40 mL/minute. MS (ESI) m/z 364 (M+H)+; 1H NMR (DMSO-d6) δ 3.54 (s, 3H), 3.60 (s, 3H), 5.00 (s, 2H), 6.43 (d, 1H), 6.82 (m, 2H), 7.38 (dd, 1H), 7.48 (t, 1H), 7.84 (dd, 1H), 8.72 (s, 1H).

Example 14

4-(2,3-dichlorobenzyl)-3-(2,3-dichlorophenyl)-4H-1,2,4-triazole

The title compound was prepared using the procedure as described in Example 1D substituting 2,3-dichlorobenzylamine for benzylamine. The residue was purified by preparative HPLC on a Waters Symmetry C8 column (25 mm ×100 mm, 7 μm particle size) using a gradient of 10% to 100% acetonitrile:0.1% aqueous trifluoroacetic acid over 8 minutes (10 minute run time) at a flow rate of 40 mL/minute. MS (ESI) m/z 374 (M+H)+; 1H NMR (DMSO-d6) δ 5.29 (s, 2H), 6.88 (dd, 1H), 7.22 (t, 1H), 7.41 (dd, 1H), 7.44 (t, 1H), 7.56 (dd, 1H), 7.81 (dd, 1H), 8.81 (s, 1H).

Example 15

4-(2,3-dichlorobenzyl)-3-(2,4-dichlorophenyl)-4H-1,2,4-triazole

The title compound was prepared using the procedure as described in Example 1D substituting 2,4-dichlorobenzylamine for benzylamine. The residue was purified by preparative HPLC on a Waters Symmetry C8 column (25 mm ×100 mm, 7 μm particle size) using a gradient of 10% to 100% acetonitrile:0.1% aqueous trifluoroacetic acid over 8 minutes (10 minute run time) at a flow rate of 40 mL/minute. MS (ESI) m/z 374 (M+H)+; 1H NMR (DMSO-d6) δ 5.23 (s, 2H), 6.96 (d, 1H), 7.30 (dd, 1H), 7.40 (dd, 1H), 7.45 (t, 1H), 7.55 (d, 1H), 7.82 (dd, 1H), 8.79 (s, 1H).

Example 16

4-(2,3-dichlorobenzyl)-3-(2,5-dichlorophenyl)-4H-1,2,4-triazole

The title compound was prepared using the procedure as described in Example 1D substituting 2,5-dichlorobenzylamine for benzylamine. The residue was purified by preparative HPLC on a Waters Symmetry C8 column (25 mm×100 mm, 7 μm particle size) using a gradient of 10% to 100% acetonitrile:0.1% aqueous trifluoroacetic acid over 8 minutes (10 minute run time) at a flow rate of 40 mL/minute. MS (ESI) m/z 374 (M+H)+; 1H NMR (DMSO-d6) δ 5.24 (s, 2H), 6.93 (d, 1H), 7.37-7.42 (m, 3H), 7.46 (t, 1H), 7.82 (dd, 1H), 8.83 (s, 1H).

Example 17

4-(2,3-dichlorobenzyl)-3-(3,4-dichlorophenyl)-4H-1,2,4-triazole

The title compound was prepared using the procedure as described in Example 1D substituting 3,4-dichlorobenzylamine for benzylamine. The residue was purified by preparative HPLC on a Waters Symmetry C8 column (25 mm×100 mm, 7 μm particle size) using a gradient of 10% to 100% acetonitrile:0.1% aqueous trifluoroacetic acid over 8 minutes (10 minute run time) at a flow rate of 40 mL/minute. MS (ESI) m/z 374 (M+H)$^+$; $^1$H NMR (DMSO-d$_6$) δ 5.14 (s, 2H), 6.95 (dd, 1H), 7.18 (d, 1H), 7.40 (dd, 1H), 7.47 (t, 1H), 7.51 (d, 1H), 7.84 (dd, 1H), 8.84 (s, 1H).

Example 18

4-(2,3-dichlorobenzyl)-3-(3,5-dichlorophenyl)-4H-1,2,4-triazole

The title compound was prepared using the procedure as described in Example 1D substituting 3,5-dichlorobenzylamine for benzylamine. The residue was purified by preparative HPLC on a Waters Symmetry C8 column (25 mm×100 mm, 7 μm particle size) using a gradient of 10% to 100% acetonitrile:0.1% aqueous trifluoroacetic acid over 8 minutes (10 minute run time) at a flow rate of 40 mL/minute. MS (ESI) m/z 374 (M+H)$^+$; $^1$H NMR (DMSO-d$_6$) δ 5.15 (s, 2H), 6.97 (d, 2H), 7.42 (dd, 1H), 7.49 (t, 1H), 7.50 (s, 1H), 7.85 (dd, 1H), 8.85 (s, 1H).

Example 19

3-(2,3-dichlorophenyl)-4-(2-methoxybenzyl)-4H-1,2,4-triazole

The title compound was prepared using the procedure described in Example 1D substituting 2-methoxybenzylamine for benzylamine. The residue was purified by preparative HPLC on a Waters Symmetry C8 column (25 mm ×100 mm, 7 μm particle size) using a gradient of 10% to 100% acetonitrile:0.1% aqueous trifluoroacetic acid over 8 minutes (10 minute run time) at a flow rate of 40 mL/minute. MS (DCI/NH$_3$) m/z 334 (M+H)$^+$; $^1$H NMR (CDCl$_3$) δ 3.75 (s, 3H), 4.99 (s, 2H), 6.81 (m, 3H), 7.30 (m, 3H) (dd, 1H), 8.27 (s, 1H).

Example 20

3-(2,3-dichlorophenyl)-4-(2-methylbenzyl)-4H-1,2,4-triazole

The title compound was prepared using the procedure as described in Example 1D substituting 2-methylbenzylamine for benzylamine. The residue was purified by preparative HPLC on a Waters Symmetry C8 column (25 mm×100 mm, 7 μm particle size) using a gradient of 10% to 100% acetonitrile:0.1% aqueous trifluoroacetic acid over 8 minutes (10 minute run time) at a flow rate of 40 mL/minute. MS (DCI/NH$_3$) m/z 318 (M+H)$^+$; $^1$H NMR (CDCl$_3$) δ 2.10 (s, 3H), 4.99 (s, 2H), 6.94 (d, 1H), 7.15 (m, 2H), 7.23-7.32 (m, 3H), 7.64 (dd, 1H), 8.06 (s, 1H).

Example 21

[4-(2,3-Dichloro-phenyl)-4H-[1,2,4]triazol-3-yl]-[2-(5-fluoro-pyridin-3-yloxy)-pyridin-3-ylmethyl]-amine

Example 21A 2-(5-Fluoro-pyridin-3-yloxy)-nicotinonitrile

The title compound was prepared using the procedure as described in Example 109A substituting 5-fluoro-pyridin-3-ol for pyridin-3-ol. MS (ESI+) m/z 216 (M+H)$^+$.

Example 21B

{2-[(5-fluoropyridin-3-yl)oxy]pyridin-3-yl}methylamine

The title compound was prepared using the procedure as described in Example 109B substituting Example 21A for Example 109A. MS (ESI$^+$) m/z 220 (M+H)$^+$.

Example 21C

[4-(2,3-Dichloro-phenyl)-4H-[1,2,4]triazol-3-yl]-[2-(5-fluoro-pyridin-3-yloxy)-pyridin-ylmethyl]-amine The title compound was prepared using the procedure as described in Example 100 substituting Example 21B for 2-methylbenzylamine. MS (ESI$^+$) m/z 431 (M+H)$^+$; $^1$H NMR (400 MHz, DMSO-d$_6$) δ ppm 4.51 (d, J=5.76 Hz, 2H) 6.71 (dd, J=5.76 Hz, 1H) 7.18 (dd, J=7.46, 4.75 Hz, 1H) 7.55 (t, J=7.97 Hz, 1H) 7.61-7.66 (m, 1H) 7.74 (dt, J=9.83, 2.37 Hz, 1H) 7.82 (dd, J=7.46, 1.70 Hz, 1H) 7.86 (dd, J=8.14, 1.70 Hz, 1H) 8.03 (dd, J=4.92, 1.86 Hz, 1H) 8.19 (s, 1H) 8.38 (dd, J=1.70, 1.02 Hz, 1H) 8.48 (d, J=2.37 Hz, 1H)

Example 22

3-(2,3-dichlorophenyl)-4-(1-phenylethyl)-4H-1,2,4-triazole

The title compound was prepared using the procedure as described in Example 1D substituting 1-phenylethylamine for benzylamine. MS (DCI/NH$_3$) m/z 318 (M+H)$^+$; $^1$H NMR (CDCl$_3$) δ 1.86 (d, 3H), 5.15 (q, 1H), 6.98 (m, 2H), 7.10 (d, 1H), 7.23 (t, 1H), 7.27-7.32 (m, 3H), 7.61 (dd, 1H), 8.40 (s, 1H).

Example 23

3-(2,3-dichlorophenyl)-4-(1-methyl-1-phenylethyl)-4H-1,2,4-triazole

The title compound was prepared using the procedure as described in Example 1D substituting 1-methyl-1-phenylethylamine for benzylamine. MS (DCI/NH$_3$) m/z 332 (M+H)$^+$; $^1$H NMR (CDCl$_3$) δ 1.65-1.98 (br s, 6H), 6.29 (dd, 1H), 6.88 (t, 1H), 7.00 (m, 2H), 7.18 (dd, 1H), 7.23-7.30 (m, 3H), 7.44 (dd, 1H), 8.50 (s, 1H).

Example 24

1-benzyl-5-(2,3-dichlorophenyl)-1H-1,2,4-triazole

Example 24A 2,3-dichloro-N-[(dimethylamino)methylene]benzamide 2,3-Dichlorobenzamide (4.96 g, 26.1 mmol) and dimethylformamide dimethylacetal (10 mL) were heated at reflux for 1.5 hours, allowed to cool to room temperature, concentrated under reduced pressure, and the residue was partitioned between diethyl ether and water. The organic phase was washed with water (2×), saturated sodium chloride, dried with sodium sulfate, filtered, and the filtrate was concentrated under reduced pressure. The residue was purified by flash chromatography eluting with ethyl acetate to provide the title compound. MS (DCI/NH$_3$) m/z 245 (M+H)$^+$.

Example 24B 1-benzyl-5-(2,3-dichlorophenyl)-1H-1,2,4-triazole

Example 24A (269 mg, 1.10 mmol), sodium acetate monohydrate (360 mg, 3.6 mmol), 70% acetic acid (3 mL), and benzylhydrazine dihydrochloride (235 mg, 1.2 mmol) were combined in 1,4 dioxane (3 mL) and heated at reflux for 2 hours. The mixture was allowed to cool to room temperature, concentrated under reduced pressure, and the residue was partitioned between methylene chloride and water. The organic phase was washed with water, dried with sodium sulfate, filtered, and the filtrate was concentrated under reduced pressure. The residue was purified by flash chromatography eluting with ethyl acetate:hexanes (1:1) to provide the title compound. MS (DCI/NH$_3$) m/z 304 (M+H)$^+$; $^1$H NMR (CDCl$_3$) δ 5.20 (s, 2H), 7.00-7.07 (m, 2H), 7.18 (dd, 1H), 7.23-7.30 (m, 4H), 7.62 (dd, 1H), 8.05 (s, 1H); Anal calcd for C$_{15}$H$_{11}$Cl$_2$N$_3$: C, 59.23; H, 3.65; N, 13.81. Found: C, 59.47; H, 3.87; N, 13.70.

Example 25

1-benzyl-5-(2,3-dichlorophenyl)-1H-1,2,3-triazole

Example 25A

[(2,3-dichlorophenyl)ethynyl](trimethyl)silane 1,2-Dichloro-3-iodobenzene (4.95 g, 18.1 mmol), trimethylsilylacetylene (2 g, 20 mmol), bis(triphenylphosphine)palladium(II)chloride (245 mg, 0.35 mmol), and copper(I)iodide (45 mg, 0.24 mmol) were combined in triethylamine (120 mL) and heated at reflux for 45 minutes. The mixture was allowed to cool to room temperature and was then partitioned between diethyl ether and saturated sodium chloride. The organic phase was dried with sodium sulfate, filtered through celite, and the filtrate was concentrated under reduced pressure. The residue was taken directly on to the next step.

Example 25B 1,2-dichloro-3-ethynylbenzene

Example 25A (4.0 g, 16.5 mmol) and potassium carbonate (2.28 g, 16.5 mmol) were combined in methanol (125 mL), stirred for 30 minutes, and the mixture was partitioned between diethyl ether and water. The organic phase was dried with sodium sulfate, filtered, and the filtrate was concentrated under reduced pressure. The residue was purified by flash chromatography eluting with pentane:diethyl ether (9:1) to provide the title compound. $^1$H NMR (CDCl$_3$) δ 3.41 (s, 1H), 7.06 (t, 1H), 7.44 (d, 2H).

Example 25C 1-benzyl-5-(2,3-dichlorophenyl)-1H-1,2,3-triazole

Example 25B (200 mg, 1.17 mmol) and benzylazide (130 mg, 0.98 mmol) were combined in ethanol (1 mL) and heated at 80° C. in a sealed tube for 16 hours. The mixture was treated with additional benzylazide (100 mg) and heated an additional 4 hours. The mixture was allowed to cool to room temperature, and concentrated under reduced pressure. The crude residue was composed of a mixture of regioisomers that were purified by flash chromatography eluting with hexanes: ethyl acetate (3:1) to provide the title compound. MS (DCI/NH$_3$) m/z 304 (M+H)$^+$; $^1$H NMR (CDCl$_3$) δ 5.43 (s, 2H), 6.90 (dd, 1H), 6.94 (m, 2H), 7.13-7.24 (m, 4H), 7.55 (dd, 1H), 7.71 (s, 1H).

Example 26

5-benzyl-1-(2,3-dichlorophenyl)-1H-1,2,3-triazole

1-Azido-2,3-dichlorobenzene (200 mg, 1.06 mmol) (Cambie *J. Organomet. Chem.* 1996, 507, 1) and 3-phenyl-1-propyne (150 μL, 1.1 equiv) were combined in toluene (0.2 mL) and heated at 100° C. for 18 hours, allowed to cool to room temperature, and then concentrated under reduced pressure to give a mixture of regioisomers. The residue was purified by flash chromatography eluting with hexanes:ethyl acetate (3:1) to provide the title compound. MS (DCI/NH$_3$) m/z 304 (M+H)$^+$; $^1$H NMR (CDCl$_3$) δ 3.87 (br s, 2H), 6.98 (m, 2H), 7.13 (dd, 1H), 7.22 (m, 3H), 7.29 (t, 1H), 7.56 (s, 1H), 7.64 (dd, 1H).

Example 27

4-benzyl-5-(2,3-dichlorophenyl)-1H-1,2,3-triazole

Example 27A 1,2-dichloro-3-(3-phenylprop-1-ynyl)benzene 1,2-Dichloro-3-iodobenzene (4.39 g, 16.1 mmol), benzylacetylene (1.96 g, 16.9 mmol), copper(I) iodide (26 mg, 0.14 mmol) and bistriphenylphosphinepalladium(II)chloride (113 mg, 0.16 mmol) were combined in triethylamine (100 mL) and heated at reflux for 2 hours. The reaction was allowed to cool to room temperature and then was partitioned between saturated sodium chloride and diethylether. The organic phase was dried with sodium sulfate, filtered, and the filtrate was concentrated under reduced pressure. The residue was purified on silica gel (eluting with hexane) to provide the title compound. MS (DCI/NH$_3$) m/z 278 (M+NH$_4$)$^+$; $^1$H NMR (CDCl$_3$) δ 3.90 (s, 2H), 7.13 (t, 1H), 7.2-7.5 (m, 7H).

Example 27B 4-benzyl-5-(2,3-dichlorophenyl)-1H-1,2,3-triazole

Example 27A (294 mg, 1.13 mmol) and azidotrimethylsilane (0.16 mL, 1.2 mol) were combined and heated at 120° C. overnight, treated with additional azidotrimethylsilane (0.25 mL, 1.89 mmol) and heated for 3 days. The reaction was allowed to cool to room temperature and was concentrated under reduced pressure. The residue was purified by flash chromatography (hexane:ethyl acetate, 3:1) to provide the title compound. MS (DCI/NH$_3$) m/z 304 (M+H)$^+$; $^1$H NMR (CDCl$_3$) δ 4.03 (s, 2H), 7.02-7.30 (m, 7H), 7.52 (dd, 1H).

Example 28

3-[2-chloro-3-(trifluoromethyl)phenyl]-4-(2-methyl-benzyl)-4H-1,2,4-triazole

Example 28A

2-[2-chloro-3-(trifluoromethyl)phenyl]-1,3,4-oxadiazole

2-Chloro-3-trifluoromethylbenzoic acid (10 g, 44.5 mmol) in sulfuric acid (1 mL) was heated at reflux in ethanol (50 mL) for 24 hours, allowed to cool to room temperature, and concentrated under reduced pressure. The residue was diluted with diethyl ether, washed with saturated sodium bicarbonate (3×), dried (sodium sulfate), filtered, and the filtrate was concentrated under reduced pressure to provide 9.65 g of the crude ester. The obtained ester was heated with hydrazine hydrate (9.4 mL 194 mmol) in ethanol (50 mL) for 3 hours, allowed to cool to room temperature, and concentrated under reduced pressure to provide the crude acylhydrazide. The obtained acylhydrazide was combined with triethylorthoformate (20 mL 120 mmol) and para-toluenesulfonic acid monohydrate (530 mg 2.8 mmol) in toluene and heated at reflux for 2 hours, allowed to cool to room temperature, and concentrated under reduced pressure. The residue was purified by flash chromatography (hexane:ethyl acetate, 3:2) to provide the title compound. MS (DCI/NH$_3$) m/z 249 (M+H)$^+$; $^1$H NMR (CDCl$_3$) δ 7.56 (t, 1H), 7.93 (dd, 1H), 8.15 (dd, 1H), 8.61 (s, 1H).

Example 28B

3-[2-chloro-3-(trifluoromethyl)phenyl]-4-(2-methyl-benzyl)-4H-1,2,4-triazole

Example 28A (190 mg 0.76 mmol) and 2-methylbenzylamine (0.105 mL 0.85 mmol) were combined in toluene (0.125 mL), heated at 100° C. for 42 hours, allowed to cool to room temperature, and concentrated under reduced pressure. The residue was purified by flash chromatography (3% methanol/ethyl acetate) to provide the title compound. MS (DCI/NH$_3$) m/z 352 (M+H)$^+$; $^1$H NMR (CDCl$_3$) δ 5.01 (s, 2H), 6.91 (d, 1H), 7.07-7.27 (m, 3H), 7.45 (t, 1H), 7.53 (dd, 1H), 7.87 (dd, 1H), 8.13 (s, 1H).

Example 29

5-(2,3-dichlorophenyl)-1-(2,3-dihydro-1-benzofuran-7-ylmethyl)-1H-1,2,3-triazole

Example 29A 2,3-dihydro-1-benzofuran-7-ylmethanol 2,3-Dihydrobenzofuran carboxylic acid (5.047 g, 30.77 mmol) in tetrahydrofuran at −10° C. was treated dropwise with a solution of 1.0 M borane-tetrahydrofuran (20 mL 20 mmol). The temperature was allowed to warm to room temperature overnight, and was then treated with additional 1.0 M borane-tetrahydrofuran (10 mL 10 mmol), and stirred at room temperature for 2 hours. The mixture was cooled to 5° C., slowly treated with methanol (20 mL), and concentrated under reduced pressure. The residue was dissolved in ethyl acetate, washed with saturated sodium bicarbonate (2×), saturated sodium chloride, dried (sodium sulfate), filtered, and the filtrate was concentrated under reduced pressure. The residue was purified by flash chromatography (hexanes:ethyl acetate, 3:2) to provide the title compound. MS (DCI/NH$_3$) M/Z 168 (M+NH$_4$)$^+$; $^1$H NMR (CDCl$_3$) δ 3.21 (t, 2H), 4.60 (t, 2H), 4.68 (s, 2H), 6.83 (t, 1H), 7.08 (dd, 1H), 7.14 (dd, 1H).

Example 29B 7-(bromomethyl)-2,3-dihydro-1-benzofuran

Example 29A (4.06 g, 27.1 mmol) and carbon tetrabromide (10.9 g, 32.8 mmol) were combined in methylene chloride (100 mL) at 0° C. and treated with triphenylphosphine (8.53 g, 32.6 mmol) portionwise. The mixture was allowed to warm to room temperature, was stirred overnight, concentrated under reduced pressure, and the residue was purified by flash chromatography (2% ethyl acetate/hexanes) to provide the title compound. $^1$H NMR (CDCl$_3$) δ 3.22 (t, 2H), 4.50 (s, 2H), 4.65 (t, 2H), 6.81 (t, 1H), 7.12 (m, 2H).

Example 29C 7-(azidomethyl)-2,3-dihydro-1-benzofuran

Example 29B (4.40 g, 20.7 mmol) in N,N-dimethylformamide (60 mL) at room temperature was treated in one portion with sodium azide (5.37 g, 82.6 mmol), stirred for 3 hours, poured into water and extracted with diethylether (2×100 mL). The organics were dried (sodium sulfate), filtered, and the filtrate was concentrated under reduced pressure. The residue was purified by flash chromatography (5% ethyl acetate/hexane) to provide the title compound. $^1$H NMR (CDCl$_3$) δ 3.23 (t, 2H), 4.31 (s, 2H), 4.60 (t, 2H), 6.85 (t, 1H), 7.06 (d, 1H), 7.19 (dd, 1H).

Example 29D 5-(2,3-dichlorophenyl)-1-(2,3-dihydro-1-benzofuran-7-ylmethyl)-1H-1,2,3-triazole Example 29C (710 mg, 4.06 mmol) and 1,2-dichloro-3-ethynylbenzene (370 mg, 2.18 mmol) were combined in toluene and heated at 100° C. overnight in a sealed tube. The reaction mixture was allowed to cool to room temperature and was concentrated under reduced pressure. The residue composed of a mixture of regioisomers was purified by flash chromatography with gradient elution (3:1 to 1:1 hexane:ethyl acetate) to provide the title compound as the minor more polar regioisomer. MS (DCI/NH$_3$) m/z 346 (M+H)$^+$; $^1$H NMR (CDCl$_3$) δ 3.08 (t, 2H), 4.34 (t, 2H), 5.41 (s, 2H), 6.69 (t, 1H), 6.78 (d, 1H), 6.97 (dd, 1H), 7.03 (dd, 1H), 7.18 (t, 1H), 7.54 (dd, 1H), 7.70 (s, 1H); Anal. calcd for C$_{17}$H$_{13}$Cl$_2$N$_3$O: C, 58.98; H, 3.78; N, 12.14. Found: C, 58.92; H, 3.61; N, 12.16.

Example 30

3-(2,3-dichlorophenyl)-4-[2-(trifluoromethyl)benzyl]-4H-1,2,4-triazole

The title compound was prepared using the procedure as described in Example 1D substituting 2-(trifluoromethyl)

benzylamine for benzylamine. MS (DCI/NH$_3$) m/z 372. (M+H)$^+$; $^1$H NMR (CDCl$_3$) δ 5.23 (s, 2H), 7.03 (d, 1H), 7.31 (m, 2H), 7.50 (m, 2H), 7.67 (m, 2H), 8.25 (s, 1H).

Example 31

3-(2,3-dichlorophenyl)-4-[2-(difluoromethoxy)benzyl]-4H-1,2,4-triazole

The title compound was prepared using the procedure as described in Example 1D substituting 2-(difluoromethoxy) benzylamine for benzylamine. MS (DCI/NH$_3$) m/z 370 (M+H)$^+$; $^1$H NMR (CDCl$_3$) δ 5.09 (s, 2H), 6.47 (t, 1H, J=72.9 Hz), 6.93 (dd, 1H), 7.07-7.14 (m, 2H), 7.26-7.39 (m, 3H), 7.66 (dd, 1H), 8.41 (s, 1H).

Example 32

3-(2,3-dichlorophenyl)-4-[2-(trifluoromethoxy)benzyl]-4H-1,2,4-triazole

The title compound was prepared using the procedure as described in Example 1D substituting 2-(trifluoromethoxy) benzylamine for benzylamine. MS (DCI/NH$_3$) m/z 388 (M+H)$^+$; $^1$H NMR (CDCl$_3$) δ 5.12 (s, 2H), 6.96 (dd, 1H), 7.18-7.43 (m, 5H), 7.66 (dd, 1H), 8.36 (s, 1H).

Example 33

3-(2,3-dichlorophenyl)-4-(2,3-difluorobenzyl)-4H-1,2,4-triazole

The title compound was prepared using the procedure as described in Example 1D substituting 2,3-difluorobenzylamine for benzylamine. MS (DCI/NH$_3$) m/z 340 (M+H)$^+$; $^1$H NMR (CDCl$_3$) δ 5.12 (s, 2H), 6.68 (t, 1H), 6.99-7.07 (m, 1H), 7.13-7.22 (m, 1H), 7.29-7.38 (m, 2H), 7.69 (dd, 1H), 8.43 (s, 1H).

Example 34

3-(2,3-dichlorophenyl)-4-[2-(methylthio)benzyl]-4H-1,2,4-triazole

The title compound was prepared as a trifluoroacetic acid salt using the procedure as described in Example 1D substituting 2-(methylthio)benzylamine for benzylamine. MS (DCI/NH$_3$) m/z 349 (M+H)$^+$; $^1$H NMR (CDCl$_3$) δ 2.41 (s, 3H), 5.11 (s, 2H), 6.92 (dd, 1H), 7.09 (td, 1H), 7.23-7.37 (m, 4H), 7.66 (dd, 1H), 8.34 (s, 1H).

Example 35

3-(2,3-dichlorophenyl)-4-(2-ethoxybenzyl)-4H-1,2,4-triazole

The title compound was prepared as its trifluoroacetic acid salt using the procedure as described in Example 1D substituting 2-ethoxybenzylamine for benzylamine. MS (DCI/NH$_3$) m/z 348 (M+H)$^+$; $^1$H NMR (CDCl$_3$) δ 1.38 (t, 3H), 4.01 (q, 2H), 5.03 (s, 2H), 5.50 (br s, 1H), 6.72-6.85 (m, 3H), 7.24-7.34 (m, 3H), 7.68 (dd, 1H), 8.51 (s, 1H).

Example 36

4-(3-chloro-2-fluorobenzyl)-3-(2,3-dichlorophenyl)-4H-1,2,4-triazole

The title compound was prepared as its trifluoroacetic acid salt using the procedure as described in Example 1D substituting 3-chloro-2-fluorobenzylamine for benzylamine. MS (DCI/NH$_3$) m/z 356 (M+H)$^+$; $^1$H NMR (CDCl$_3$) δ 5.12 (s, 2H), 6.81 (t, 1H), 7.02 (t, 1H), 7.32-7.40 (m, 3H), 7.68 (dd, 1H), 8.50 (s, 1H).

Example 37

3-(2,3-dichlorophenyl)-4-[2-fluoro-3-(trifluoromethyl)benzyl]-4H-1,2,4-triazole

The title compound was prepared as its trifluoroacetic acid salt using the procedure as described in Example 1D substituting 2-fluoro-3-(trifluoromethyl)benzylamine for benzylamine. MS (DCI/NH$_3$) m/z 390 (M+H)$^+$; $^1$H NMR (CDCl$_3$) δ 5.17 (s, 2H), 5.47 (br s, 1H), 7.10-7.36 (m, 4H), 7.61 (m, 1H), 7.68 (dd, 1H), 8.51 (s, 1H).

Example 38

3-(2,3-dichlorophenyl)-4-(1-naphthylmethyl)-4H-1,2,4-triazole

The title compound was prepared as its trifluoroacetic acid salt using the procedure as described in Example 1D substituting 1-naphthylmethylamine for benzylamine. MS (DCI/NH$_3$) m/z 354 (M+H)$^+$; $^1$H NMR (CDCl$_3$) δ 3.70 (br s, 1H), 5.47 (s, 2H), 7.20 (dd, 1H), 7.29-7.62 (m, 6H), 7.64 (dd, 1H), 7.88 (m, 1H), 8.17 (s, 1H).

Example 39

3-(2,3-dichlorophenyl)-4-(thien-3-ylmethyl)-4H-1,2,4-triazole

The title compound was prepared as its trifluoroacetic acid salt using the procedure as described in Example 1D substituting thien-3-ylmethylamine for benzylamine. MS (DCI/NH$_3$) m/z 310 (M+H)$^+$; $^1$H NMR (CDCl$_3$) δ 5.07 (s, 2H), 6.81 (dd, 1H), 7.05 (d, 1H), 7.31-7.34 (m, 3H), 7.66 (dd, 1H), 8.46 (s, 1H).

Example 40

3-(2,3-dichlorophenyl)-4-(3-furylmethyl)-4H-1,2,4-triazole

The title compound was prepared as its trifluoroacetic acid salt using the procedure as described in Example 1D substituting 3-furylmethylamine for benzylamine. MS (DCI/NH$_3$) m/z 294 (M+H)$^+$; $^1$H NMR (CDCl$_3$) δ 4.95 (s, 2H), 6.22 (m, 1H), 7.35 (s, 1H), 7.39-7.43 (m, 3H), 7.69 (dd, 1H), 8.46 (s, 1H).

Example 41

3-(2,3-dichlorophenyl)-4-(2,5-difluorobenzyl)-4H-1,2,4-triazole

The title compound was prepared as its trifluoroacetic acid salt using the procedure as described in Example 1D substituting 2,5-difluorobenzylamine for benzylamine. MS (DCI/NH$_3$) m/z 340 (M+H)$^+$; $^1$H NMR (CDCl$_3$) δ 5.07 (s, 2H), 6.58 (m, 1H), 7.03 (m, 2H), 7.30-7.38 (m, 2H), 7.66 (dd, 1H), 8.46 (s, 1H).

Example 42

3-(2,3-dichlorophenyl)-4-[5-fluoro-2-(trifluoromethyl)benzyl]-4H-1,2,4-triazole

The title compound was prepared as its trifluoroacetic acid salt using the procedure as described in Example 1D substituting 5-fluoro-2-(trifluoromethyl)benzylamine for benzylamine. MS (DCI/NH$_3$) m/z 390 (M+H)$^+$; $^1$H NMR (CDCl$_3$) δ 5.25 (s, 2H), 6.69 (dd, 1H), 7.15 (m, 1H), 7.61-7.72 (m, 2H), 8.33 (s, 1H).

Example 43

4-(5-chloro-2-methylbenzyl)-3-(2,3-dichlorophenyl)-4H-1,2,4-triazole

The title compound was prepared as its trifluoroacetic acid salt using the procedure as described in Example 1D substituting 5-chloro-2-methylbenzylamine for benzylamine. MS (DCI/NH$_3$) m/z 352 (M+H)$^+$; $^1$H NMR (CDCl$_3$) δ 2.08 (s, 3H), 5.00 (s, 2H), 6.87 (d, 1H), 7.09 (d, 1H), 7.21 (dd, 1H), 7.28-7.34 (m, 2H), 7.66 (dd, 1H), 8.26 (s, 1H).

Example 44

3-(2,3-dichlorophenyl)-4-[2-fluoro-5-(trifluoromethyl)benzyl]-4H-1,2,4-triazole

The title compound was prepared as its trifluoroacetic acid salt using the procedure as described in Example 1D substituting 2-fluoro-5-(trifluoromethyl)benzylamine for benzylamine. MS (DCI/NH$_3$) m/z 390 (M+H)$^+$; $^1$H NMR (CDCl$_3$) δ 5.16 (s, 2H), 7.05 (dd, 1H), 7.15-7.25 (m, 2H), 7.31 (t, 1H), 7.61 (m, 1H), 7.68 (dd, 1H), 8.48 (s, 1H).

Example 45

4-[2-chloro-5-(trifluoromethyl)benzyl]-3-(2,3-dichlorophenyl)-4H-1,2,4-triazole

The title compound was prepared as its trifluoroacetic acid salt using the procedure as described in Example 1D substituting 2-chloro-5-(trifluoromethyl)benzylamine for benzylamine. MS (DCI/NH$_3$) m/z 406 (M+H)$^+$; $^1$H NMR (CDCl$_3$) δ 5.25 (s, 2H), 7.08 (s, 1H), 7.23-7.33 (m, 2H), 7.52 (m, 2H), 7.66 (dd, 1H), 8.51 (s, 1H).

Example 46

3-(2,3-dichlorophenyl)-4-(5-fluoro-2-methylbenzyl)-4H-1,2,4-triazole

The title compound was prepared as its trifluoroacetic acid salt using the procedure as described in Example 1D substituting 5-fluoro-2-methylbenzylamine for benzylamine. MS (DCI/NH$_3$) m/z 336 (M+H)$^+$; $^1$H NMR (CDCl$_3$) δ 2.08 (s, 3H), 5.02 (s, 2H), 6.66 (dd, 1H), 6.97 (m, 1H), 7.15 (dd, 1H), 7.34 (m, 2H), 7.68 (t, 1H), 8.33 (s, 1H).

Example 47

4-(5-chloro-2-fluorobenzyl)-3-(2,3-dichlorophenyl)-4H-1,2,4-triazole

The title compound was prepared as its trifluoroacetic acid salt using the procedure as described in Example 1D substituting 5-chloro-2-fluorobenzylamine for benzylamine. MS (DCI/NH$_3$) m/z 356 (M+H)$^+$; $^1$H NMR (CDCl$_3$) δ 5.04 (s, 2H), 6.79 (dd, 1H), 7.00 (t, 1H), 7.28 (m, 2H), 7.35 (t, 1H), 7.69 (dd, 1H), 8.40 (s, 1H).

Example 48

4-(6-chloro-2-fluoro-3-methylbenzyl)-3-(2,3-dichlorophenyl)-4H-1,2,4-triazole

The title compound was prepared as its trifluoroacetic acid salt using the procedure as described in Example 1D substituting 6-chloro-2-fluoro-3-methylbenzylamine for benzylamine. MS (DCI/NH$_3$) m/z 370 (M+H)$^+$; $^1$H NMR (CDCl$_3$) δ 2.20 (d, 3H), 5.18 (d, 2H), 7.07-7.18 (m, 2H), 7.35 (m, 2H), 7.66 (dd, 1H), 8.33 (s, 1H).

Example 49

3-(2,3-dichlorophenyl)-4-(2,3,6-trifluorobenzyl)-4H-1,2,4-triazole

The title compound was prepared as its trifluoroacetic acid salt using the procedure as described in Example 1D substituting 2,3,6-trifluorobenzylamine for benzylamine. MS (DCI/NH$_3$) m/z 358 (M+H)$^+$; $^1$H NMR (CDCl$_3$) δ 5.14 (s, 2H), 6.84 (m, 1H), 7.17 (m, 1H), 7.31-7.38 (m, 2H), 7.69 (dd, 1H), 8.41 (s, 1H).

Example 50

4-(2-chloro-3,6-difluorobenzyl)-3-(2,3-dichlorophenyl)-4H-1,2,4-triazole

The title compound was prepared as its trifluoroacetic acid salt using the procedure as described in Example 1D substituting 2-chloro-3,6-difluorobenzylamine for benzylamine. MS (DCI/NH$_3$) m/z 374 (M+H)$^+$; $^1$H NMR (CDCl$_3$) δ 5.21 (d, 2H, J=1 Hz), 6.99 (dt, 1H), 7.19 (m, 1H), 7.35 (m, 2H), 7.67 (m, 1H), 8.32 (s, 1H).

Example 51

3-(2,3-dichlorophenyl)-4-(3-methoxybenzyl)-4H-1,2,4-triazole

The title compound was prepared as its trifluoroacetic acid salt using the procedure as described in Example 1D substituting 3-methoxybenzylamine for benzylamine. MS (DCI/NH$_3$) m/z 334 (M+H)$^+$; $^1$H NMR (CDCl$_3$) δ 3.74 (s, 3H), 4.98 (d, 2H), 6.53 (t, 1H), 6.60 (d, 1H), 6.84 (dd, 1H), 7.19-7.31 (m, 3H), 7.61-7.66 (m, 1H), 8.32 (s, 1H).

Example 52

4-(2-chloro-6-fluoro-3-methylbenzyl)-3-(2,3-dichlorophenyl)-4H-1,2,4-triazole

The title compound was prepared as its trifluoroacetic acid salt using the procedure as described in Example 1D substituting 2-chloro-6-fluoro-3-methylbenzylamine for benzylamine. MS (DCI/NH$_3$) m/z 370 (M+H)$^+$; $^1$H NMR (CDCl$_3$) δ 2.31 (s, 3H), 5.19 (d, 2H), 6.90 (t, 1H), 7.23 (dd, 1H), 7.35 (m, 2H), 7.66 (dd, 1H), 8.26 (s, 1H).

Example 53

3-(2,3-dichlorophenyl)-4-(1-phenylprople)-4H-1,2,4-triazole

The title compound was prepared as its trifluoroacetic acid salt using the procedure as described in Example 1D substituting 1-phenylpropylamine for benzylamine. MS (DCI/NH$_3$) m/z 332 (M+H)$^+$; $^1$H NMR (CDCl$_3$) δ 0.95 (t, 3H), 2.20-2.35 (m, 2H), 4.82 (t, 1H), 6.85-7.0 (m, 3H), 7.2-7.35 (m, 4H), 7.65 (dd, 1H), 8.77 (s, 1H).

Example 54

3-(2,3-dichlorophenyl)-4-(2,3-dihydro-1H-inden-1-yl)-4H-1,2,4-triazole

The title compound was prepared as its trifluoroacetic acid salt using the procedure as described in Example 1D substituting 2,3-dihydro-1H-inden-1-ylamine for benzylamine. MS (DCI/NH$_3$) m/z 330 (M+H)$^+$; $^1$H NMR (CDCl$_3$) δ 2.05-2.2 (m, 1H), 2.57-2.7 (m, 1H), 2.9-3.0 (m, 1H), 3.08-3.2 (m, 1H), 5.45 (t, 1H), 7.1 (d, 1H), 7.25-7.35 (m, 3H), 7.42 (t, 1H), 7.49 (dd, 1H), 7.71 (dd, 1H), 8.11 (s, 1H).

Example 55

3-(2,3-dichlorophenyl)-4-(2,3-dihydro-1-benzofuran-7-ylmethyl)-4H-1,2,4-triazole

Example 55A 2,3-dihydro-1-benzofuran-7-ylmethylamine

Example 29C (2.2 g, 12.6 mmol) in tetrahydrofuran (10 mL) was treated with lithium aluminum hydride (0.71 g, 18.7 mmol) in tetrahydrofuran (20 mL) at 0° C. dropwise. The mixture was stirred at 0° C. for 90 minutes then carefully treated in succession with water (0.7 mL), 15% sodium hydroxide (0.7 mL) and then water (2.1 mL). After stirring overnight, the mixture was filtered through celite, the filter cake was washed with tetrahydrofuran (70 mL), and the filtrate concentrated under reduced pressure. The crude was dissolved in diethylether, washed with water, and extracted with 1N hydrochloric acid (2×20 mL). The acidic extracts were combined, basified with potassium carbonate, and extracted with methylene chloride (4×). The organic extracts were combined, dried (potassium carbonate), filtered, and the filtrate was concentrated under reduced pressure to provide the title compound. MS (DCI/NH$_3$) m/Z 150 (M+H)$^+$;$^1$H NMR (CDCl$_3$) δ 3.21 (t, 2H), 3.82 (s, 2H), 4.59 (t, 2H), 6.81 (t, I1H), 7.03 (d, 1H), 7.10 (dd, 1H).

Example 55B 3-(2,3-dichlorophenyl)-4-(2,3-dihydro-1-benzofuran-7-ylmethyl)-4H-1,2,4-triazole The title compound was prepared using the procedure as described in Example 1D substituting Example 55A for benzylamine. The product was purified by flash chromatography (5% methanolethyl acetate) to provide the title compound. MS (DCI/NH$_3$) m/z 346 (M+H)$^+$; $^1$H NMR (CDCl$_3$) δ 3.18 (t, 2H), 4.52 (t, 2H), 4.93 (s, 2H), 6.59 (d, 1H), 6.71 (t, 1H), 7.13 (d, 1H), 7.24-7.34 (m, 2H), 7.63 (dd, 1H), 8.34 (s, 1H).

Example 56

3-(2,3-dichlorophenyl)-4-[2,3-dihydro-1-benzofuran-3-yl]-4H-1,2,4-triazole

The title compound was prepared using the procedure as described in Example 1D substituting 2,3-dihydro-1-benzofuran-3-ylamine (prepared using the procedure as described in Kaluza *Chem. Ber.* 1955; 88, 597) for benzylamine. MS (DCI/NH$_3$) m/z 332 (M+H)$^+$; $^1$H NMR (CDCl$_3$) δ 4.5 (br d, 1H), 4.68 (m, 1H), 5.58 (dd, 1H), 6.98 (m, 2H), 7.17 (d, 1H), 7.32-7.48 (m, 3H), 7.71 (dd, 1H), 7.96 (s, 1H).

Example 57

3-(2,3-dichlorophenyl)-4-[(1R)-2,3-dihydro-1H-inden-1-yl]-4H-1,2,4-triazole

The title compound was prepared as its trifluoroacetic acid salt using the procedure as described in Example 1D substituting (1R)-2,3-dihydro-1H-inden-1-ylamine for benzylamine. MS (APCI) m/z 330 (M+H)$^+$; $^1$H NMR (CDCl$_3$) δ 2.05-2.2 (m, 1H), 2.57-2.7 (m, 1H), 2.9-3.0 (m, 1H), 3.08-3.2 (m, 1H), 5.45 (t, 1H), 7.1 (d, 1H), 7.2-7.35 (m, 3H), 7.42 (t, 1H), 7.49 (dd, 1H), 7.71 (dd, 1H), 8.11 (s, 1H).

Example 58

3-(2,3-dichlorophenyl)-4-[(1S)-2,3-dihydro-1H-inden-1-yl]-4H-1,2,4-triazole

The title compound was prepared as its trifluoroacetic acid salt using the procedure as described in Example 1D substituting (1S)-2,3-dihydro-1H-inden-1-ylamine for benzylamine. MS (APCI) m/z 330 (M+H)$^+$; $^1$H NMR (CDCl$_3$) δ 2.05-2.2 (m, 1H), 2.57-2.7 (m, 1H), 2.9-3.0 (m, 1H), 3.08-3.2 (m, 1H), 5.43 (t, 1H), 7.1 (d, 1H), 7.2-7.35 (m, 3H), 7.42 (t, 1H), 7.49 (d, 1H), 7.70 (dd, 1H), 8.05 (s, 1H).

Example 59

3-(2,3-dichlorophenyl)-4-(1,2,3,4-tetrahydronaphthalen-1-yl)-4H-1,2,4-triazole

The title compound was prepared as its trifluoroacetic acid salt using the procedure as described in Example 1D substituting 1,2,3,4-tetrahydronaphthalen-1-ylamine for benzylamine. MS (APCI) m/z 344 (M+H)$^+$; $^1$H NMR (CDCl$_3$) δ 1.7-1.95 (br m, 3H), 2.5 (br s, 1H), 2.8 (dt, 1H), 2.95 (dt, 1H), 5.19 (t, 1H), 6.99 (br s, 1H), 7.18 (m, 1H), 7.28 (m, 1H), 7.40 (t, 1H), 7.47 (dd, 1H), 7.69 (dd, 1H), 8.00 (s, 1H).

Example 60

3-(2,3-dichlorophenyl)-4-(3-methyl-2,3-dihydro-1H-inden-1-yl)-4H-1,2,4-triazole

The title compound was prepared as its trifluoroacetic acid salt using the procedure as described in Example 1D substituting 3-methylindan-1-amine for benzylamine. MS (APCI) m/z 344 (M+H)$^+$; $^1$H NMR (CDCl$_3$) δ 1.41 (d, 3H), 1.72 (m, 1H), 2.89 (m, 1H), 3.17 (m, 1H), 5.39 (t, 1H), 7.03 (m, 1H), 7.26-7.32 (m, 2H), 7.38-7.43 (m, 2H), 7.73 (d, 1H), 8.43 (s, 1H).

Example 61

3-(2,3-dichlorophenyl)-4-(4,4-dimethyl-1,2,3,4-tetrahydronaphthalen-1-yl)-4H-1,2,4-triazole The title compound was prepared as its trifluoroacetic acid salt using the procedure as described in Example 1D substituting 4,4-dimethyl-1,2,3,4-tetrahydronaphthalen-1-ylamine hydrochloride (prepared as described in Woods *J. Org. Chem.* 1954, 19; 1290) for benzylamine and also using diisopropylethylamine as a base. MS (APCI) m/z 372 (M+H)$^+$; $^1$H NMR (CDCl$_3$) δ 1.27 (s, 3H), 1.38 (s, 3H), 1.67 (m, 2H), 1.9 (br m, 1H), 2.14 (br m, 1H), 5.15 (t, 1H), 6.95 (br m, 1H), 7.17 (td, 1H), 7.34 (t, 1H), 7.39 (m, 2H), 7.44 (td, 1H), 7.69 (dd, 1H), 7.94 (s, 1H).

Example 63

3-(2,3-dichlorophenyl)-4-(3,4-dihydro-2H-chromen-4-yl)-4H-1,2,4-triazole

The title compound was prepared using the procedure as described in Example 1D substituting 3,4-dihydro-2H-chromen-4-ylamine hydrochloride (prepared according to the procedure described in Fernandez *Chem. Commun.* 1997, 2.) for benzylamine and also using diisopropylethylamine. MS (DCI/NH$_3$) m/z 346 (M+H)$^+$; $^1$H NMR (CDCl$_3$) δ 2.08 (m, 1H), 2.28 (m, 1H), 4.18 (m, 2H), 5.21 (t, 1H), 6.93 (m, 3H), 7.28 (m, 1H), 7.41 (t, 1H), 7.47 (dd, 1H), 7.70 (dd, 1H), 8.01 (s, 1H).

Example 64

3-[2-chloro-3-(trifluoromethyl)phenyl]-4-[(1R)-2,3-dihydro-1H-inden-1-yl]-4H-1,2,4-triazole The title compound was prepared using the procedure as described in Example 28B substituting (1R)-2,3-dihydro-1H-inden-1-ylamine for 2-methylbenzylamine. MS (DCI/NH$_3$) m/z 364 (M+H)$^+$; $^1$H NMR (CDCl$_3$) δ 2.14 (m, 1H), 2.62 (m, 1H), 2.94 (m, 1H), 3.1 (m, 1H), 5.41 (t, 1H), 7.11 (d, 1H), 7.2-7.3 (m, 3H), 7.57 (t, 1H), 7.73 (dd, 1H), 7.93 (dd, 1H), 8.01 (s, 1H).

Example 65

3-[2-chloro-3-(trifluoromethyl)phenyl]-4-[2-(methylthio)benzyl]-4H-1,2,4-triazole The title compound was prepared using the procedure as described in Example 28B substituting 2-(methylthio)benzylamine for 2-methylbenzylamine. MS (DCI/NH$_3$) m/z 384 (M+H)$^+$; $^1$H NMR (CDCl$_3$) δ 2.40 (s, 3H), 5.14 (s, 2H), 6.92 (dd, 1H), 7.07 (td, 1H), 7.23 (dd, 1H), 7.33 (td, 1H), 7.48 (t, 1H), 7.58 (dd, 1H), 7.91 (dd, 1H), 8.46 (s, 1H).

Example 66

4-(3-chloro-2-methylbenzyl)-3-(2,3-dichlorophenyl)-4H-1,2,4-triazole

The title compound was prepared as its trifluoroacetic acid salt using the procedure as described in Example 1D substituting 3-chloro-2-methylbenzylamine for benzylamine. MS (DCI/NH$_3$) m/z 352 (M+H)$^+$; $^1$H NMR (CDCl$_3$) δ 2.15 (s, 3H), 5.03 (s, 2H), 6.85 (d, 1H), 7.09 (t, 1H), 7.31 (m, 2H), 7.36 (d, 1H), 7.64 (m, 1H), 8.08 (s, 1H).

Example 67

3-(2,3-dichlorophenyl)-4-2{-[(trifluoromethyl)thio]benzyl}-4H-1,2,4-triazole The title compound was prepared as its trifluoroacetic acid salt using the procedure as described in Example 1D substituting 2-[(trifluoromethyl)thio]benzylamine for benzylamine. MS (DCI/NH$_3$) m/z 404 (M+H)$^+$; $^1$H NMR (CDCl$_3$) δ 5.33 (s, 2H), 7.05 (dd, 1H), 7.29 (m, 2H), 7.38-7.51 (m, 2H), 7.65 (dd, 1H), 7.70 (d, 1H), 8.28 (s, 1H).

Example 68

3-(2,3-dichlorophenyl)-4-(4-fluoro-2,3-dihydro-1H-inden-1-yl)-4H-1,2,4-triazole The title compound was prepared as its trifluoroacetic acid salt using the procedure as described in Example 1D substituting 4-fluoro-2,3-dihydro-1H-inden-1-ylamine hydrochloride for benzylamine and also using diisopropylethylamine. MS (DCI/NH$_3$) m/z 348 (M+H)$^+$; $^1$H NMR (CDCl$_3$) δ 2.18 (m, 1H), 2.68 (m, 1H), 2.95 (m, 1H), 3.18 (m, 1H), 5.45 (t, 1H), 6.9 (d, 1H), 7.05 (t, 1H), 7.26 (m, 1H), 7.41 (t, 1H), 7.47 (dd, 1H), 7.70 (dd, 1H), 8.05 (s, 1H).

Example 69

3-(2,3-dichlorophenyl)-4-[5-(trifluoromethyl)-2,3-dihydro-1H-inden-1-yl]-4H-1,2,4-triazole The title compound was prepared as its trifluoroacetic acid salt using the procedure as described in Example 1D substituting 5-(trifluoromethyl)-2,3-dihydro-1H-inden-1-ylamine hydrochloride for benzylamine and also using diisopropylethylamine. MS (DCI/NH$_3$) m/z 398 (M+H)$^+$; $^1$H NMR (CDCl$_3$) δ 2.1 (m, 1H), 2.7 (m, 1H), 3.0 (m, 1H), 3.1 (m, 1H), 5.46 (t, 1H), 7.22 (br d, 1H), 7.41 (t, 1H), 7.48 (dd, 1H), 7.53 (d, 1H), 7.60 (s, 1H), 7.70 (dd, 1H), 8.05 (s, 1H).

Example 70

3-{[3-(2,3-dichlorophenyl)-4H-1,2,4-triazol-4-yl]methyl}pyridine

The title compound was prepared as its trifluoroacetic acid salt using the procedure as described in Example 1D substituting pyridin-3-ylmethylamine for benzylamine. MS (DCI/NH$_3$) m/z 305 (M+H)$^+$; $^1$H NMR (CDCl$_3$) δ 5.27 (s, 2H), 7.31 (dd, 1H), 7.37 (t, 1H), 7.60 (dd, 1H), 7.72 (m, 2H), 8.54 (s, 1H), 8.66 (s, 1H), 8.68 (s, 1H), 9.60 (br s, 2H).

Example 71

3-(2,3-dichlorophenyl)-4-(2-ethylbenzyl)-4H-1,2,4-triazole

Example 71A

2-ethylbenzylamine

Lithium aluminum hydride (7.4 g 196 mmol) in tetrahydrofuran (130 mL) was slowly treated with 2-ethylbenzonitrile (4.99 g 38 mmol) in tetrahydrofuran (40 mL) at 0° C. under nitrogen. The mixture was stirred for 30 minutes at 0° C., 2 hours at room temperature, recooled to 0° C., and then slowly treated in succession with water (7.4 mL), 15% sodium hydroxide (7.4 mL) and water (22 mL). Additional tetrahydrofuran (50 mL) was added to facilitate stirring. The reaction mixture was filtered through celite, the filter cake was washed with tetrahydrofuran (150 mL), the filtrate was concentrated under reduced pressure, and the residue was partitioned between methylene chloride/saturated sodium chloride. The organic phase was dried (potassium carbonate), filtered, and the filtrate was concentrated under reduced pressure to provide the title compound. $^1$H NMR (CDCl$_3$) δ 1.24 (t, 3H), 2.69 (q, 2H), 3.89 (s, 2H), 7.20 (m, 3H), 7.32 (m, 1H).

Example 71B 3-(2,3-dichlorophenyl)-4-(2-ethylbenzyl)-4H-1,2,4-triazole

The title compound was prepared as a trifluoroacetic acid salt using the procedure as described in Example 1D substituting Example 71A for benzylamine. MS (DCI/NH$_3$) m/z 332 (M+H)$^+$; $^1$H NMR (CDCl$_3$) δ 1.05 (t, 3H), 2.42 (q, 2H), 5.02 (s, 2H), 6.96 (dd, 1H), 7.19 (td, 1H), 7.22 (d, 1H), 7.29-7.34 (m, 3H), 7.65 (m, 1H), 8.10 (s, 1H).

Example 72

5-[2-chloro-3-(trifluoromethyl)phenyl]-1-[2,3-dihydro-1H-inden-1-yl]-1H-1,2,4-triazole Example 72A 2-chloro-N-[(dimethylamino)methylene]-3-(trifluoromethyl)benzamide Step A 2-Chloro-3-trifluoromethylbenzoic acid (4.52 g, 20.13 mmol) and thionylchloride (10 mL, 137 mmol) were heated to reflux in toluene (40 mL) for 3 hours. The mixture was allowed to cool to room temperature and concentrated under reduced pressure. The residue was treated with dry toluene and concentrated under reduced pressure (3×).

Step B

A solution of 0.5 M ammonia in 1,4-dioxane (140 mL) at 5° C. was slowly treated with the obtained residue from step A in diethyl ether (30 mL) and then allowed to warm to room temperature overnight. The mixture was concentrated under reduced pressure and the residue was partitioned between methylene chloride and water. The organic phase was washed with saturated sodium chloride, dried (sodium sulfate), filtered, and the filtrate was concentrated under reduced pressure.

Step C

The crude amide from step B (~20 mmol) and dimethylformamide dimethylacetal (10 mL) were combined and heated at reflux for 1.5 hours, allowed to cool to room temperature, concentrated under reduced pressure, and partitioned between water and diethyl ether. The organic phase was washed with water (2×), saturated sodium chloride, dried (sodium sulfate), filtered, and the filtrate was concentrated under reduced pressure. The residue was purified by flash chromatography eluting with ethyl acetate to provide the title compound. MS (DCI/NH$_3$) m/z 279 (M+H)$^+$; $^1$H NMR (CDCl$_3$) δ 3.18 (s, 3H), 3.23 (s, 3H), 7.38 (t, 1H), 7.71 (dd, 1H), 7.88 (dd, 1H), 8.63 (s, 1H).

Example 72B

5-[2-chloro-3-(trifluoromethyl)phenyl]-1-[2,3-dihydro-1H-inden-1-yl]-1H-1,2,4-triazole Example 72A (117 mg, 0.42 mmol) and indan-1-yl-hydrazine oxalate (Huebner *J. Org. Chem.* 1962, 27; 4465) (110 mg, 0.46 mmol) were combined in ethanol (5 mL) and heated at reflux for 1 hour, allowed to cool to room temperature, and partitioned between diethyl ether and saturated aqueous sodium bicarbonate. The organic phase was dried (sodium sulfate), filtered, and the filtrate was concentrated under reduced pressure. The residue was purified by flash chromatography eluting with hexanes:ethyl acetate (3:2) to provide the title compound. MS (DCI/NH$_3$) m/z 364 (M+H)$^+$; $^1$H NMR (CDCl$_3$) δ 2.6 (m, 2H), 2.92 (m, 1H), 3.24 (m, 1H), 5.60 (t, 1H), 6.93 (m, 1H), 7.17 (m, 1H), 7.28 (m, 2H), 7.55 (t, 1H), 7.67 (d, 1H), 7.91 (dd, 1H), 8.04 (s, 1H); Anal. calcd for C$_{18}$H$_{13}$ClF$_3$N$_3$; C, 59.43; H, 3.60; N, 11.55. Found: C, 59.12; H, 3.38; N, 11.34.

Example 73

3-[2-chloro-3-(trifluoromethyl)phenyl]-4-(2-ethylbenzyl)-4H-1,2,4-triazole

The title compound was prepared using the procedure as described in Example 28B substituting 2-ethylbenzylamine for 2-methylbenzylamine. MS (DCI/NH$_3$) m/z 366 (M+H)$^+$; $^1$H NMR (CDCl$_3$) δ 1.03 (t, 3H), 2.41 (q, 2H), 5.04 (s, 2H), 6.90 (dd, 1H), 7.13 (td, 1H), 7.18 (d, 1H), 7.28 (td, 1H), 7.44 (td, 1H), 7.53 (dd, 1H), 7.86 (dd, 1H), 8.12 (s, 1H).

Example 74

5-benzyl-1-(2,3-dichlorophenyl)-1H-1,2,4-triazole

N-Formylphenylacetamide (Finkbeiner *J. Org. Chem.* 1965, 30; 2861) (200 mg, 1.22 mmol) and 2,3-dichlorophenylhydrazine hydrochloride (314 mg, 1.47 mmol) were combined in glacial acetic acid (8 mL) and refluxed under a nitrogen atmosphere for 1 hour and then concentrated under reduced pressure at 60° C. The residue was purified by flash chromatography eluting with hexanes/ethyl acetate (6/1) to provide the title compound. MS (ESI$^+$) m/z 305 (M+1H)$^+$; $^1$H NMR (300 MHz, DMSO-d$_6$) δ ppm 4.02 (s, 2H) 6.97-7.02 (m, 2H) 7.16-7.25 (m, 3H) 7.52-7.58 (m, 2H) 7.88 (dd, J=6.8, 3.1 Hz, 1H) 8.16 9s, 1 H).

Example 75

3-{[1-(2,3-dichlorophenyl)-1H-1,2,4-triazol-5-yl]methyl}pyridine

Example 75A

[2-(2,3-dichlorophenyl)-2H-[1,2,4]-triazol-3-yl]-pyridin-3-yl-methanol

To a solution of Example 83A (1.00 g, 4.67 mmol) in tetrahydrofuran (35 mL) was slowly added n-butyl lithium (2.24 mL, 5.61 mmol) at −78° C. The reaction mixture was stirred for 1.5 hours at −78° C. and then nicotinaldehyde (612 mg, 5.61 mmol) in tetrahydrofuran (6 mL) was added dropwise. The reaction mixture was stirred for 12 hours at room temperature and then quenched with water (5 mL). The reaction mixture was extracted with EtOAc, dried with MgSO$_4$, filtered and concentrated to provide 1.3 g of the title compound. MS (ESI/NH$_3$) m/z 221 (M)$^+$

Example 75B

Thionocarbonic acid O,O-bis-{[2-(2,3-dichlorophenyl)-2H-[1,2,4]-triazol-3-yl]-pyridin-3-yl-methyl}ester To a solution of product of Example 75A (800 mg, 2.49 mmol) and 4-N,N-dimethylaminopyridine (1.08 g, 8.72 mmol) in CH$_3$CN (30 mL) was added phenyl chlorothionocarbonate (645 mg, 3.74 mmol) under N$_2$. The reaction mixture was stirred for 5 hours at room temperature and then concentrated under reduced pressure. The residue was purified by flash column chromatography on SiO$_2$ (1% methanol/dichloromethane) to give the title compound. $^1$H NMR (300 MHz, DMSO-d$_6$) δ ppm 6.51 (s, 1H) 7.45 (dd, J=8.0, 4.9 Hz, 1H) 7.58-7.69 (m, 1H) 7.70-7.77 (m, 1H) 7.97 (dd, J=8.0, 1.5 Hz, 1H) 8.06 (d, J=7.5 Hz, 1H) 8.33 (s, 1H) 8.57 (dd, J=4.7, 1.7 Hz, 1H) 8.72 (d, J=2.4 Hz, 1H).

Example 75C

3-{[1-(2,3-dichlorophenyl)-1H-1,2,4-triazol-5-yl]methyl}pyridine

A mixture of product from Example 75B (330 mg, 0.48 mmol), n-butyltin hydride (0.3 mL, 1.08 mmol) and 2,2'-azobisobutylnitrile (24 mg, 0.15 mmol) in toluene (15 mL) was degassed under an oxygen free N$_2$ atmosphere for 20 minutes. The reaction mixture was stirred 100° C. for 5 hours. The solvent was removed under vacuum and the residue purified by flash chromatography on SiO$_2$ (gradient elution, 1% to 2.5% methanol/dichloromethane) to provide the title compound. MS (ESI$^+$) m/z 305 (M)$^+$; $^1$H NMR (300 MHz, DMSO-d$_6$) δ ppm 4.05-4.08 (m, 2H) 7.25-7.30 (m, 1H) 7.48-7.54 (m, 1H) 7.57 (t, J=8.1 Hz, 1H) 7.65 (dd, J=9.0, 1.7 Hz, 1H) 7.90 (dd, J=8.1, 1.7 Hz, 1H) 8.17 (s, 1H) 8.26 (d, J=2.0 Hz, 1H) 8.41 (dd, J=4.7, 1.7 Hz, 1H).

Example 76

1-(2,3-dichlorophenyl)-5-(2-methylbenzyl)-1H-1,2,4-triazole

Example 76A

N-formyl-2-(o-methylphenyl)acetamide

A mixture of 2-o-tolylacetamide (Lee, Dong-Ung; Mayer, Klaus K.; Wiegrebe, Wolfgang; Lauber, Rolf; Schlunegger, Urs P.; *Arch. Pharm.* 1988, 321; 265-272) (320 mg, 2.15 mmol) and N,N,-dimethylformamide dimethylacetal (1.1 mL, 8.59 mmol) was stirred under N$_2$ for 55 min at 120° C. The excess of N,N,-dimethylformamide dimethylacetal was eliminated under reduced pressure. The residue was dissolved in 3 mL of 70% aqueous acetic acid and stirred at 0° C. for 30 min. The precipitate was filtered, washed with water and dried to afford the title compound as a white solid. MS (DCI/NH$_3$) m/z 195 (M+NH$_4$)$^+$.

Example 76B 1-(2,3-dichlorophenyl)-5-(2-methylbenzyl)-1H-1,2,4-triazole

The title compound was prepared using the procedure as described in Example 74 substituting Example 76A for N-formylphenylacetamide. MS (ESI$^+$) m/z 318 (M); $^1$H NMR (300 MHz, DMSO-d$_6$) δ 2.09 (s, 3H), 4.01 (s, 2H), 6.77 (d, J=7.5 Hz, 1H), 6.92-7.00 (m, 1H), 7.06-7.10 (m, 2H), 7.49-7.60 (m, 2H), 7.83-7.88 (m, 1H), 8.13 (s, 1H); Anal. calcd for C$_{16}$H$_{13}$Cl$_2$N$_3$: C, 60.39; H, 4.12; N, 13.21. Found: C, 60.07; H, 4.04; N, 13.01.

Example 77

1-(2,3-dichlorophenyl)-5-(thien-3-ylmethyl)-1H-1,2,4-triazole

Example 77A

N-formyl-2-(thien-3-yl)acetamide

The title compound was prepared using the procedure as described in Example 76A substituting 2-thiophen-3-yl-acetamide (Schenck; Steinmetz; *Justus Liebigs Ann. Chem.* 1963, 668; 19, 26) for 2-o-tolylacetamide. MS (DCI/NH$_3$) m/Z 187 (M+NH$_4$)$^+$.

Example 77B 1-(2,3-dichlorophenyl)-5-(thien-3-ylmethyl)-1H-1,2,4-triazole

The title compound was prepared using the procedure as described in Example 74 substituting Example 77A for N-formylphenylacetamide. MS (ESI$^+$) m/z 311 (M+H)$^+$; $^1$H NMR (300 MHz, DMSO-d$_6$) δ 4.02 (s, 2H), 6.81-6.85 (m, 1H), 7.02-7.06 (m, 1H), 7.39-7.43 (m, 1H), 7.53-7.59 (m, 2H), 7.86-7.91 (m, 1H), 8.17 (s, 1H); Anal. calcd for C$_{13}$H$_9$Cl$_2$N$_3$S: C, 50.33; H, 2.92; N, 13.55. Found: C, 50.51; H, 2.69; N, 13.55.

Example 78

5-{[3-(2,3-dichlorophenyl)-4H-1,2,4-triazol-4-yl]methyl}isoquinoline

The title compound was prepared using the procedure as described in Example 1D substituting isoquinolin-5-ylmethylamine (prepared using the procedure as in EP 13411) for benzylamine. MS (ESI$^+$) m/z 356 (M+H)$^+$; $^1$H NMR (300 MHz, DMSO-d$_6$) δ 5.66 (s, 2H), 7.17 (d, J=7.1 Hz, 1H), 7.31-7.40 (m, 2H), 7.49 (t, J=7.5 Hz, 1H), 7.65-7.76 (m, 2H), 8.04 (d, J=8.1 Hz, 1H), 8.46 (d, J=6.1 Hz, 1H), 8.91 (s, 1H) 9.29 (s, 1H); Anal. calcd for C$_{18}$H$_{12}$Cl$_2$N$_4$0.1CF$_3$CO$_2$H: C, 59.49; H, 3.34; N, 15.33. Found: C, 59.62; H, 3.24; N, 15.21.

Example 79

8-{[3-(2,3-dichlorophenyl)-4H-1,2,4-triazol-4-yl]methyl}quinoline

The title compound was prepared using the procedure as described in Example 1D substituting quinolin-8-ylmethylamine for benzylamine. MS (ESI$^+$) m/z 356 (M+H)$^+$; $^1$H NMR (300 MHz, DMSO-d$_6$) δ 5.71 (s, 2H), 7.28 (d, J=6.1 Hz, 1H), 7.34-7.41 (m, 2H), 7.45-7.57 (m, 2H), 7.72-7.77 (m, 1H), 7.92 (dd, J=8.1, 1.4 Hz, 1H), 8.35 (dd, J=8.5, 1.7 Hz, 1H), 8.77-8.80 (m, 1H), 8.84 (s, 1H); Anal. calcd for

49

$C_{18}H_{12}Cl_2N_5$ 0.05$CF_3CO_2H$: C, 60.17; H, 3.37; N, 15.55. Found: C, 59.91; H, 3.59; N, 15.34.

Example 80

5-benzyl-1-phenyl-1H-1,2,4-triazole

Phenylhydrazine hydrochloride (0.09 g, 0.6 mmol) in 5 mL glacial acetic acid was treated with triethylamine (0.06 g, 0.6 mmol), warmed to 70° C., treated with N-formylphenylacetamide (0.1 g, 0.6 mmol), and heated at 90° C. for 1 hour. The mixture was then allowed to cool to room temperature and was concentrated under reduced pressure. The residue was dissolved in ethyl acetate and the organics were washed with saturated $NaHCO_3$, 1M NaOH, water, and brine. The organics were then dried ($MgSO_4$), and filtered, and the filtrate was concentrated under reduced pressure. The residue was purified by flash chromatography (40% hexanes/ethyl acetate) to provide the title compound. MS (ESI) m/e: 236 $(M+H)^+$; $^1$H NMR (DMSO-$d_6$) δ 4.2 (s, 2H), 7.05-7.1 (d, 2H), 7.17-7.3 (m, 3H), 7.45-7.6 (m, 5H), 8.1 (s, 1H); Anal. calcd. for C, 76.57; H, 5.57; N, 17.86. Found C, 76.32; H: 5.81; N, 17.63.

Example 81

1-[2-chloro-3-(trifluoromethyl)phenyl]-5-(2-methyl-benzyl)-1H-1,2,4-triazole

Example 81A

1-[2-chloro-3-(trifluoromethyl)phenyl]-5-(2-methyl-benzyl)-1H-1,2,4-triazole

The title compound was prepared using the procedure as described in Example 80 substituting 2-chloro-3-trifluoromethylphenylhydrazine hydrochloride for phenylhydrazine hydrochloride and substituting Example 76A for N-formylphenylacetamide. The residue was purified by flash chromatography (20% ethyl acetate/hexanes) to provide the title compound. MS (ESI) m/e: 352 (M+H); $^1$H NMR (DMSO-$d_6$) δ 2.05 (s, 3H), 4.05 (s, 2H), 6.7-6.75 (d, 1H), 6.85-6.96 (m, 1H), 7.04-7.1 (d, 2H), 7.7-7.75 (t, 1H), 7.89-7.97 (d, 1H), 8.05-8.1 (d, 1H), 8.18 (s, 1H); Anal. calcd. for C: 58.05, H: 3.73, N: 11.95. Found C, 58.10; H, 3.86; N, 11.68. The title compound (0.12 g, 0.34 mmol) in ethyl acetate (3 mL) was treated with 1 M HCl/diethyl ether (5 mL). After stirring for 1 hour, the mixture was diluted with diethyl ether, filtered, and the filter cake was dried under high vacuum to provide the title compound as a hydrochloride salt. MS (ESI) m/e: 352 $(M+H)^+$; $^1$H NMR (DMSO-$d_6$) δ 2.05 (s, 3H), 4.05 (s, 2H), 6.7-6.75 (d, 1H), 6.85-6.96 (m, 1H), 7.04-7.1 (d, 2H), 7.7-7.75 (t, 1H), 7.89-7.97 (d, 1H), 8.05-8.1 (d, 1H), 8.18 (s, 1H); Anal. calcd. for C, 52.60; H, 3.63; N, 10.82. Found C, 52.54; H, 3.42; N, 10.79.

Example 82

1-[2-chloro-3-(trifluoromethyl)phenyl]-5-(2,3-dihydro-1H-inden-1-yl)-1H-1,2,4-triazole The title compound was prepared using the procedure as described in Example 80 substituting 2-chloro-3-trifluoromethylphenylhydrazine hydrochloride for phenylhydrazine hydrochloride and substituting N-formyl-2,3-dihydro-1H-indene-1-carboxamide (prepared using the procedure as described in Example 76A, substituting from indan-1-carboxamide [Seidl Tetrahedron 1964, 20, 633] for 2-o-tolylacetamide) for N-formylphenylacetamide. The residue was purified by flash chromatography (40% ethyl acetate/hexanes) to provide the title compound. MS (ESI) m/e: 364 $(M+H)^+$; $^1$H NMR (DMSO-$d_6$) δ 2.05-2.45 (m, 2H), 2.8-3.05 (m, 2H), 4.29-4.35 (t, 1H), 6.95-7.05 (bs, 1H), 7.03-7.1 (t, 1H), 7.1-7.21 (t, 1H), 7.2-7.3 (d, 1H), 7.78-7.82 (t, 2H), 8.0-8.01 (bs, 0.5H), 8.18 (s, 1H), 8.22 (bs, 0.5H); Anal. calcd. for C, 59.43; H, 3.60; N, 11.55. Found C, 59.20; H, 3.34; N, 11.48

Example 83

Benzyl-[2-(2,3-dichloro-phenyl)-2H-[1,2,4]triazol-3-yl]-amine

Example 83A 1-(2,3-Dichloro-phenyl)-1H-[1,2,4]triazole

A suspension of 2,3 dicholorophenylhydrazine hydrochloride (5 g, 23 mmol) in 20 mL N,N-dimethyl formamide was heated at 180° C. for 12 hours. The reaction was cooled and the resulting solid was dissolved in ethyl acetate (50 mL). The organic layer was washed with water (3×30 mL), brine (1×20 mL), dried ($MgSO_4$), filtered and concentrated to give 5 g of a chalky solid, used without further purification. MS (ESI/$NH_3$) m/z 215 $(M+H)^+$ Example 83B 5-Bromo-1-(2,3-dichloro-phenyl)-1H-[1,2,4]triazole To Example 83A (2 g, 8 mmol) in 25 mL carbon tetrachloride was added N-bromosuccinimide (2.86 g, 16.2 mmol) and a catalytic amount of benzoyl peroxide. The solution was heated to reflux for 12 hours, then cooled and filtered through Celite, washing the solids with warm carbon tetrachloride (20 mL). The solvent was removed in vacuo and the residue purified by column chromatography (gradient elution, 20% to 35% ethyl acetate/hexanes) to give 1.2 g of the compound as an off-white solid. MS (ESI/$NH_3$) m/z 293 $(M)^+$ Example 83C Benzyl-[2-(2,3-dichloro-phenyl)-2H-[1,2,4]triazol-3-yl]-amine Example 83B (0.1 g, 0.34 mmol) was combined with 0.1 mL of benzylamine and heated to 100° C. for 24 hours, cooled and purified by column chromatography (gradient elution; 25% ethyl acetate/hexanes to 35%) to give 0.065 g of the title compound as a white solid. MS (ESI/$NH_3$) m/z 318 $(M)^+$ $^1$H NMR (δ, DMSO-$d_6$); 4.41-4.5 (d, 2H), 7.1-7.26 (m, 2H), 7.3-7.37 (m, 4H), 7.6 (s, 1H), 7.8-7.9 (m, 1H).

Example 84

[2-(2,3-Dichloro-phenyl)-2H-[1,2,4]triazol-3-yl]-(2-methyl-benzyl)-amine

The title compound was prepared using the procedure as described in Example 83C substituting 2-methylbenzylamine for benzylamine. MS (ESI/$NH_3$) m/z 366 $(M+H)^+$; $^1$H NMR (δ, DMSO-$d_6$); 2.3 (s, 3H), 4.41-4.5 (d, 2H), 7.1-7.32 (m, 5H), 7.62 (m, 2H), 7.8-7.9 (d, 1H), 8.0-8.09 (d, 1H).

Example 85

[2-(2,3-Dichloro-phenyl)-2H-[1,2,4]triazol-3-yl]-(2-trifluoromethyl-benzyl)-amine The title compound was prepared using the procedure as described in Example 83C substituting 2-trifluoromethylbenzylamine for benzylamine. MS (ESI/NH$_3$) m/z 385 (M+H)$^+$; $^1$H NMR (δ, DMSO-d$_6$); 4.61-4.65 (d, 2H), 7.2-7.28 (t, 1H), 7.41-7.5 (t, 1H), 7.52-7.78 (m, 6H), 7.8-7.88 (d, 1H)

Example 86

[2-(2,3-Dichloro-phenyl)-2H-[1,2,4]triazol-3-yl]-(3-methoxy-benzyl)-amine

The title compound was prepared using the procedure as described in Example 83C substituting 3-methoxybenzylamine for benzylamine. MS (ESI/NH$_3$) m/z 348 (M+H)$^+$; $^1$H NMR (δ, DMSO-d$_6$); 4.38-4.41 (d, 2H), 6.75-6.79 (d, 1H), 6.82-6.90 (m, 2H), 7.1-7.17 (t, 1H), 7.19-7.21 (t, 1H), 7.51-7.58 (d, 2H), 7.6 (s, 1H), 7.8-7.85 (m, 1H).

Example 87

[2-(2,3-Dichloro-phenyl)-2H-[1,2,4]triazol-3-yl]-(2,3-dimethoxy-benzyl)-amine

The title compound was prepared using the procedure as described in Example 83C substituting 2,3-dimethoxybenzylamine for benzylamine. MS (ESI/NH$_3$) m/z 379 (M); $^1$H NMR (δ, DMSO-d$_6$); 3.7 (s, 3H), 3.8 (s, 3H), 4.41-4.5 (d, 2H), 6.8-7.05 (m, 4H), 7.5-7.6 (m, 3H), 7.8-7.85 (m, 1H).

Example 88

[2-(2,3-Dichloro-phenyl)-2H-[1,2,4]triazol-3-yl]-(2-methylsulfanyl-benzyl)-amine The title compound was prepared using the procedure as described in Example 83C substituting 2-thiomethylbenzylamine for benzylamine MS (ESI/NH$_3$) m/z 364 (M+H)$^+$; $^1$H NMR (δ, DMSO-d$_6$); 2.5 (s, 3H), 4.41-4.5 (d, 2H), 7.1-7.19 (m, 2H), 7.2-7.3 (m, 4H), 7.5-7.6 (m, 3H), 7.82-7.85 (m, 1H).

Example 89

[2-(2,3-Dichloro-phenyl)-2H-[1,2,4]triazol-3-yl ]-(2-methanesulfonyl-benzyl)-amine Example 88 (0.015 g, 0.041 mmol) was dissolved in 2 mL acetone and treated with OXONE (0.1 g, 0.16 mmol) for 24 hours. The resulting slurry was taken up in 25 mL ethyl acetate and washed with water (3×10 mL), brine (1×10 mL), then dried (MgSO$_4$), filtered and concentrated to give 0.014 g of the title compound as a white solid. MS (ESI/NH$_3$) m/z 398 (M+H)$^+$; $^1$H NMR (δ, DMSO-d$_6$); 3.4, (s, 3H), 4.8-4.85 (d, 2H), 7.28-7.39 (t, 1H), 7.25-7.76 (m, 5H), 7.82-7.92 (m, 2H).

Example 90

[2-(2,3-Dichloro-phenyl)-2H-[1,2,4]triazol-3-yl]-(2-methoxy-benzyl)-amine

The title compound was prepared using the procedure as described in Example 83C substituting 2-methoxybenzylamine for benzylamine. MS (ESI/NH$_3$) m/z 348 (M+H)$^+$; $^1$H NMR (δ, DMSO-d$_6$); 3.78 (s, 3H), 4.38-4.4 (d, 2H), 6.8-6.95 (m, 3H), 7.15-7.22 (m, 2H), 7.5-7.59 (m, 3H), 7.81-7.85 (m, 1H).

Example 91

[2-(2,3-Dichloro-phenyl)-2H-[1,2,4]triazol-3-yl]-(2-ethoxy-benzyl)-amine

The title compound was prepared using the procedure as described in Example 83C substituting 2-ethoxybenzylamine for benzylamine. MS (ESI/NH$_3$) m/z 348 (M+H)$^+$; $^1$H NMR (δ, DMSO-d$_6$); 1.22-1.35 (t, 3H), 3.91-4.05 (q, 2H), 4.38-4.4 (d, 2H), 6.8-6.95 (m, 3H), 7.15-7.22 (m, 2H), 7.5-7.59 (m, 3H), 7.81-7.85 (m, 1H).

Example 92

[2-(2,3-Dichloro-phenyl)-2H-[1,2,4]triazol-3-yl]-pyridin-3-ylmethyl-amine

The title compound was prepared using the procedure as described in Example 83C substituting C-pyridin-3-yl-methylamine for benzylamine. MS (ESI/NH$_3$) m/z 319 (M+H)$^+$; $^1$H NMR (δ, DMSO-d$_6$); 4.5-4.6 (d, 2H), 7.3-7.4 (t, 1H), 7.5-7.65 (m, 3H), 7.8-7.9 (m, 2H), 8.25-8.3 (d, 1H), 8.7-8.8 (m, 2H).

Example 93

1-(2,3-dichlorophenyl)-N-[(2-pyrrolidin-1-ylpyridin-3-yl)methyl]-1H-[1,2,4]triazole-5-amine

Example 93A 2-pyrrolidin-1-yl-nicotinonitrile

To an oven-dried, N$_2$-purged, 50-mL flask containing a magnetic stir bar were added 2-fluoronicotinonitrile (1.22 g, 10.0 mmol), anhydrous tetrahydrofuran (5 mL), and triethylamine (3.04 g, 4.19 mL, 30.0 mmol). The flask was sealed with a septum and cooled to 0° C. in an ice bath. Neat pyrrolidine (1.04 g, 1.24 mmol, 15.0 mmol) was added via syringe. The mixture was stirred at 0° C. for 30 minutes and then allowed to warm to room temperature overnight. Water (10 mL) was added and the mixture was transferred to a separatory funnel. The mixture was extracted with dichloromethane (3×10 mL). The combined organic extracts were dried over magnesium sulfate, filtered, and concentrated by rotary evaporation to a brown oil. The product was recrystallized from ethyl acetate/hexanes to give 1.29 g (75%) of the title compound as a tan powder. MS (ESI+) m/z 174.0 (M+H)$^+$; $^1$H NMR (DMSO-d$_6$) δ 1.91-1.95 (m, 4H), 3.63-3.68 (m, 4H), 6.68 (dd, J=7.6, 4.6 Hz, 1H), 7.91 (dd, J=7.6, 1.9 Hz, 1H), 8.31 (dd, J=4.7, 2.0 Hz, 1H).

Example 93B

C-(2-pyrrolidin-1-yl-pyridin-3-yl)-methylamine

To a thick-walled pressure bottle was added Raney nickel (~5 g) and ammonia-saturated methanol (100 mL). Example 93A (866 mg, 5.00 mmol) was added, and the bottle was inserted into a Parr shaker. The bottle was charged with 60 psi of H$_2$ gas, and the grey mixture was shaken under static hydrogen pressure at room temperature for 2 hours. After venting, the solids were removed by vacuum filtration through a glass frit covered with a nylon filter. The solvent/volatiles were removed by rotary evaporation to give ~900 mg of a pale green oil to give the title compound which was used without further purification for the next step.

Example 93C 1-(2,3-dichlorophenyl)-N-[(2-pyrrolidin-1-ylpyridin-3-yl)methyl]-1H-[1,2,4]triazole-5-amine The title compound was prepared using the procedure as described in Example 83C substituting Example 93B for benzylamine. MS (ESI/NH$_3$) m/z 389 (M+H)$^+$; $^1$H NMR (δ, DMSO-d$_6$); 1.78-1.90 (m, 4H), 3.4-3.52 (m, 4H), 4.41-4.45 (d, 2H), 6.82-6.85 (m, 1H), 6.98-7.02 (t, 1H), 7.4-7.6 (m, 4H), 7.79-7.85 (m, 1H), 7.95-7.99 (d, 1H).

Example 94

[2-(2,3-Dichloro-phenyl)-2H-[1,2,4]triazol-3-yl]-[2-(pyridin-3-yloxy)-benzyl]-amine

Example 94A 2-(Pyridin-3-yloxy)-benzonitrile

To a solution of 3-hydoxypyridine sodium salt (purchased from Acros) (2.54 g, 26.71 mmol) in N,N-dimethyl formamide (50 mL) was added 2-fluoronicotinonitrile (3.32 g, 26.68 mmol) dropwise and the solution was heated at 100° C. for 2 hours. To the reaction mixture was added ethyl acetate (100 mL) and 1M NaHCO$_3$ (150 mL) and it was filtered to remove black tar. The filtrate was decolorized with activated charcoal and extracted with ethyl acetate (3×30 ml). The combined organic extracts were dried (Na$_2$SO$_4$), filtered and concentrated. The crude product was purified by flash column chromatography on silica gel using dichloromethane to give the title compound. MS (ESI$^+$) m/z 197 (M+H)$^+$.

Example 94B 2-(Pyridin-3-yloxy)-benzylamine

To a solution of Example 94A (4.28 g, 21.84 mmol) in 7N NH$_3$ in methanol (200 ml) was added Raney nickel (12 g) under argon atmosphere. The reaction mixture was kept on a shaker under 60 psi H$_2$ atmosphere. After 6 hours at room temperature, the reaction mixture was filtered through a micro pore filter and concentrated to give the title compound. MS (ESI$^+$) m/z 201 (M+H)$^+$.

Example 94C

[2-(2,3-Dichloro-phenyl)-2H-[1,2,4]triazol-3-yl]-[2-(pyridin-3-yloxy)-benzyl]-amine The title compound was prepared using the procedure as described in Example 83C substituting Example 94B for benzylamine. MS (ESI/NH$_3$) m/z 412 (M+H)$^+$; $^1$H NMR (δ, DMSO-d$_6$); 4.41-4.45 (d, 2H), 6.82-6.85 (d, 1H), 6.98-7.02 (t, 1H), 7.19-7.6 (m, 9H), 7.8-7.85 (d, 1H), 8.3-8.39 (m, 2H).

Example 95

[2-(2,3-Dichloro-phenyl)-2H-[1,2,4]triazol-3-yl]-[2-(pyridin-3-yloxy)-pyridin-3-ylmethyl]-amine The title compound was prepared using the procedure as described in Example 83C substituting Example 109B for benzylamine. MS (ESI/NH$_3$) m/z 413 (M+H)$^+$ $^1$H NMR (δ, DMSO-d$_6$); 4.51-4.59 (d, 2H), 7.05-7.2 (m, 2H), 7.4-7.6 (m, 4H), 7.7-7.81 (m, 2H), 7.95-8.0 (d, 1H), 8.4-8.48 (m, 2H)

Example 96

[2-(2,3-Dichloro-phenyl)-2H-[1,2,4]triazol-3-yl]-(2-thiophen-3-yl-pyridin-3-ylmethyl)-amine

Example 96A 2-thiophen-3-ylnicotinonitrile

To an oven-dried, N$_2$-purged, 50 mL, round-bottomed flask containing a magnetic stir bar were added potassium fluoride (767 mg, 13.2 mmol), bis(tri-t-butylphosphine)palladium (51.0 mg, 0.10 mmol), tris(dibenzylideneacetone)dipalladium (46 mg, 0.05 mmol), 2-chloro-3-cyanopyridine (559 mg, 4.00 mmol), and 3-thiopheneboronic acid (819 mg, 6.4 mmol). The flask was sealed with a septum and purged with dry N$_2$ atmosphere. Anhydrous dioxane (4 mL) was added via syringe. The reaction mixture was heated to ~90° C. in an oil bath for 18 hours. After cooling to room temperature, ethyl acetate (15 mL) was added and the mixture was filtered through a pad of silica. The filtrate was concentrated by rotary evaporation to give a brown oil. The product was purified by recrystallization from ethyl acetate/hexanes to give 417 mg (56%) of the title compound. MS (ESI–) m/z 186.9 (M+H)$^+$; $^1$H NMR (CDCl$_3$) δ 7.30 (7.8, 4.7 Hz, 1H), 7.44 (dd, J=5.3, 2.9 Hz, 1H), 7.88 (dd, J=5.1, 1.4 Hz, 1H), 8.03 (dd, J=8.0, 1.9 Hz, 1H), 8.29 (dd, J=3.0, 1.4 Hz, 1H), 8.82 (dd, J=4.7, 1.7 Hz, 1H).

Example 96B

C-(2-Thiophen-3-yl-pyridin-3-yl)-methylamine

The title compound was prepared using the procedure as described in Example 93B substituting Example 96A for Example 93A.

Example 96C 2-(2,3-Dichloro-phenyl)-2H-[1,2,4]triazol-3-yl -(2-thiophen-3-yl -pyridin-3-ylmethyl)-amine The title compound was prepared using the procedure as described in Example 83C substituting Example 96B for benzylamine. MS (ESIINH$_3$) m/z 402 (M+H)$^+$; $^1$H NMR (δ, DMSO-d$_6$); 4.51-4.59 (d, 2H), 7.15-7.2 (t, 1H), 7.3-7.36 (m, 1H), 7.42-7.62 (m, 4H), 7.75-7.81 (3H), 8.45-8.5 (m, 1H)

Example 97

(2-Azetidin-1-yl-pyridin-3-ylmethyl)-[2-(2,3-dichloro-phenyl)-2H-[1,2,4]triazol-3-yl]-amine

Example 97A

2-Azetidin-1-yl-nicotinonitrile

The title compound was prepared using the procedure as described in Example 93A, substituting azetidine hydrochloride for pyrrolidine. MS (ESI+) m/z 160.0 (M+H)$^+$; $^1$H NMR (DMSO-d$_6$) δ 2.28-2,38 (m, 2H), 4.19-4.25 (m, 4H), 6.73 (dd, J=7.6, 4.9 HZ, 1H), 7.92 (dd, J=7.7, 1.8 Hz, 1H), 8.30 (dd, J=4.9, 1.9 Hz, 1H).

Example 97B

C-(2-Azetidin-1-yl-pyridin-3-yl)-methylamine

The title compound was prepared using the procedure as described in Example 93B, substituting Example 97A for Example 93A.

Example 97C (2-Azetidin-1-yl-pyridin-3-ylmethyl)-[2-(2,3-dichloro-phenyl)-2H-[1,2,4]triazol-3-yl]-amine The title compound was prepared using the procedure as described in Example 83C substituting Example 97B for benzylamine. MS (ESI/NH$_3$) m/z 375 (M+H)$^+$; $^1$H NMR (δ, DMSO-d$_6$); 2.19-2.25 (m, 2H), 3.95-4.04 (m, 4H), 4.25-4.3 (d, 2H), 6.62-6.65 (m, 1H), 6.98-7.02 (t, 1H), 7.4-7.6 (m, 4H), 7.79-7.85 (m, 1H), 7.95-7.99 (d, 1H).

Example 98

1-(2,3-dichlorophenyl)-N-[(2-morpholin-4-ylpyridin-3-yl)methyl]-1H-[1,2,4]-triazol-5-amine

Example 98A

4-[3-(azidomethyl)pyridin-2-yl]morpholine

To a solution of (2-morpholino-3-pyridinyl)methanol (1 g, 5.01 mmol)(purchased from Maybridge) in dichloromethane (20 ml) was added thionyl chloride (3 ml) dropwise at 0° C. and allowed to warm to room temperature. After stirring at room temperature for 6 hours, the solvents were removed under reduced pressure and the residue was dissolved and concentrated repeatedly in dichloromethane to remove excess of thionyl chloride. The obtained crude chloride intermediate, (2-morpholino-3-pyridinyl)methylchloride, was immediately dissolved in acetone (25 ml) and sodium azide (1.63 g, 25.05 mmol) was added at room temperature. The reaction was refluxed overnight, the solvents were removed under reduced pressure, dissolved in dichloromethane (25 ml) and washed with 1M NaHCO$_3$ (25 ml). The aqueous layer was extracted with dichloromethane (2×20 ml). The combined organic extracts were dried (Na$_2$SO$_4$), filtered and concentrated to yield 0.62 g (57%) of product as a thick yellowish liquid. MS (ESI$^+$) m/z 220 (M+H)$^+$;

Example 98B (2-morpholin-4-ylpyridin-3-yl)methylamine

To a solution of the product from Example 98A (0.62 g) in methanol (10 ml) was added Pd/C (0.06 g) under N$_2$ atmosphere. The reaction mixture was stirred at room temperature under H$_2$ atmosphere. After 6 hours, the reaction mixture was filtered through celite and concentrated to yield 0.42 g (78%) of product. MS (ESI$^+$) m/z 194 (M+H)$^+$;

Example 98C 1-(2,3-dichlorophenyl)-N-[(2-morpholin-4-ylpyridin-3-yl)methyl]-1H-[1,2,4]-triazol-5-amine The title compound was prepared using the procedure as described in Example 83C substituting Example 98B for benzylamine. MS (ESI/NH$_3$) m/z 403 (M+H)$^+$; $^1$H NMR (δ, DMSO-d$_6$); 2.95-2.99 (m, 4H), 3.65-3.72 (m, 4H), 4.39-4.43 (d, 2H), 6.98-7.01 (m, 1H), 7.05-7.12 (t, 1H), 7.44-7.65 (m, 4H), 7.79-7.85 (m, 1H), 8.15-8.2 (d, 2H).

Example 99

[2-(2,3-Dichloro-phenyl)-2H-[1,2,4]triazol-3-yl]-(2-methyl-pyridin-3-ylmethyl)-amine The title compound was prepared using the procedure as described in Example 83C substituting C-(2-Methyl-pyridin-3-yl)-methylamine (purchased from General Intermediates of Canada, Inc) for benzylamine. MS (ESI/NH$_3$) m/z 333 (M+H)$^+$; $^1$H NMR (δ, DMSO-d$_6$); 3.5 (s, 3H), 4.39-4.42 (d, 2H), 7.01-7.2 (m, 2H), 7.45-7.6 (m, 3H), 7.79-7.82 (d, 1H), 8.29-8.33 (d, 1H).

Example 100

[4-(2,3-Dichloro-phenyl)-4H-[1 2,4]triazol-3-yl]-(2-methyl-benzyl)-amine

To a solution of 2-methylbenzylamine (0.121 g, 1 mmol) in tetrahydrofuran (10 ml) was added 2,3-dichlorophenyl-isothiocyanate (0.204 g, 1 mmol) drop wise at room temperature and stirred for one hour. To the reaction mixture was added triethylamine (0.42 ml), mercuric chloride (0.326 g, 1.2 mmol), and 3 ml of 1M hydrazine solution in tetrahydrofuran. After stirring at room temperature for 12 hours, the reaction mixture was filtered. To the filtrate was added triethylorthoformate (2.5 ml) and formic acid (0.1 ml). The reaction mixture was heated to reflux for 2 hours, cooled, and triturated in hexanes. The viscous precipitate was purified by preparative HPLC on a waters Symmetry C8 column (40 mm×100 mm, 7 μm particle size) using a gradient of 10% to 100% acetonitrile: ammonium acetate (10 mM) over 15 min at a flow rate of 70 L/min to yield 80 mg of the title compound. MS (ESI$^+$) m/z 333 (M+H)$^+$; $^1$H NMR (300 MHz, DMSO-d$_6$) δ ppm 2.28 (s, 3H) 4.35 (d, J=5.76 Hz, 2H) 6.49 (t, J=5.76 Hz, 1H) 7.05-7.18 (m, 3H) 7.26 (t, J=3.90 Hz, 1H) 7.55 (t, 2H) 7.83 (dd, J=7.46, 2.37 Hz, 1H) 8.14 (s, 1H); Anal. calcd for C$_{13}$H$_{14}$Cl$_2$N$_4$: C, 57.67; H, 4.23; N, 16.81. Found: C, 57.11; H, 4.24; N, 16.37.

Example 101

[4-(2,3-Dichloro-phenyl)-4H-[1,2,4]triazol-3-yl]-pyridin-3-ylmethyl-amine

The title compound was prepared using the procedure as described in Example 100 substituting 3-(aminomethyl)pyridine for 2-methylbenzylamine. MS (ESI$^+$) m/z 320 (M+H)$^+$; $^1$H NMR (300 MHz, DMSO-d$_6$) δ ppm 4.40 (d, J=5.76 Hz, 2H) 6.69 (d, J=11.87 Hz, 1H) 7.30-7.36 (m, 1H) 7.51-7.63 (m, 2H) 7.73 (dt, J=7.80, 1.86 Hz, 1H) 7.85 (dd, J=7.63, 2.20 Hz, 1H) 8.16 (s, 1H) 8.43 (dd, J=4.75, 1.70 Hz, 1H) 8.54 (d, J=1.70 Hz, 1 H).

Example 102

[4-(2,3-Dichloro-phenyl)-4H-[1,2,4]triazol-3-yl]-(2-methyl-pyridin-3-ylmethyl)-amine The title compound was prepared using the procedure as described in Example 100 substituting C-(2-methyl-pyridin-3-yl)-methylamine for 2-methylbenzylamine. MS (ESI$^+$) m/z 334 (M+H)$^+$; $^1$H NMR (300 MHz, DMSO-d$_6$) δ 2.47 (s, 3H)

4.37 (d, J=5.42 Hz, 2H) 6.61 (t, J=5.76 Hz, 1H) 7.16 (dd, J=7.63, 4.92 Hz, 1H) 7.51-7.64 (m, 3H) 7.85 (dd, J=7.63, 1.86 Hz, 1H) 8.16 (s, 1H) 8.30 (dd, J=4.75, 1.70 Hz, 1H).

Example 103

[4-(2,3-Dichloro-phenyl)-5-methyl-4H-[1,2,4]triazol-3-yl]-(2-methyl-benzyl)-amine The title compound was prepared using the procedure as described in Example 100 substituting triethylorthoacetate for triethylorthoformate. MS (ESI$^+$) m/z 347 (M+H)$^+$; $^1$H NMR (300 MHz, DMSO-d$_6$) δ ppm 1.96 (s, 3H) 2.26 (s, 3H) 4.31 (d, J=5.76 Hz, 2H) 6.27 (t, J=5.76 Hz, 1H) 7.07-7.16 (m, 3H) 7.20-7.30 (m, 1H) 7.51-7.61 (m, 2H) 7.85 (dd, J=6.10, 3.73 Hz, 1H).

Example 104

[4-(2,3-Dichloro-phenyl)-5-ethyl-4H-[1,2,4]triazol-3-yl]-(2-methyl-benzyl)-amine The title compound was prepared using the procedure as described in Example 100 substituting triethylorthpropionate for triethylorthoformate. MS (ESI$^+$) m/z 361 (M+H)$^+$; $^1$H NMR (300 MHz, DMSO-d$_6$) δ ppm 1.03 (t, J=7.63 Hz, 3H) 2.21-2.35 (m, 5H) 4.22-4.39 (m, 2H) 6.26 (t, J=5.76 Hz, 1H) 7.07-7.16 (m, 3H) 7.20-7.30 (m, 1H) 7.50-7.64 (m, 2 H) 7.85 (dd, J=7.12, 2,37 Hz, 1H).

Example 105

[4-(2,3-Dichloro-phenyl)-4H-[1,2,4]triazol-3-yl]-[2-(pyridin-2-yloxy)-berzyl]-amine The title compound was prepared using the procedure as described in Example 100 substituting 2-(Pyridin-2-yloxy) benzylamine hydrochloride (purchased from Array Biopharma) for 2-methylbenzylamine. MS (ESI$^+$) m/z 412 (M+H)$^+$; $^1$H NMR (300 MHz, DMSO-d$_6$) δ ppm 4.30 (d, J=5.76 Hz, 2H) 6.44 (t, J=5.93 Hz, 1H) 6.98-7.07 (m, 2H) 7.11 (dd, J=6.78, 5.43 Hz, 1H) 7.19 (td, J=7.38, 1.19 Hz, 1H) 7.28 (td, J=7.63, 2.03 Hz, 1 H) 7.42 (dd, J=7.63, 1.53 Hz, 1H) 7.49-7.58 (m, 2H) 7.79-7.90 (m, 2H) 8.08 (dd, J=5.09, 1.36 Hz, 1H) 8.14 (s, 1H).

Example 106

[4-(2,3-Dichloro-phenyl)-4H-[1,2,4]triazol-3-yl]-(2-pyrrolidin-1-yl-pyridin-3-ylmethyl)-amine The title compound was prepared using the procedure as described in Example 100 substituting Example 93B for 2-methylbenzylamine. MS (ESI$^+$) m/z 389 (M+H)$^+$; $^1$H NMR (300 MHz, DMSO-d$_6$) δ ppm 1.76-1.89 (m, 4H) 3.40-3.51 (m, 4H) 4.38 (d, J=5.09 Hz, 2H) 6.48 (t, 1H) 6.65 (dd, J=7.46, 4.75 Hz, 1H) 7.47 (dd, J=7.29, 1.86 Hz, 1H) 7.50-7.60 (m, 2H) 7.83 (dd, J=7.46, 2,37 Hz, 1H) 7.97 (dd, J=4.75, 2.03 Hz, 1H) 8.15 (s, 1H).

Example 107

[4-(2,3-Dichloro-phenyl)-4H-[1,2,4]triazol-3-yl]-[2-(pyridin-3-yloxy)-benzyl]-amine The title compound was prepared using the procedure as described in Example 100 substituting Example 94B for 2-methylbenzylamine. MS (ESI$^+$) m/z 412 (M+H)$^+$; $^1$H NMR (300 MHz, DMSO-d$_6$) δ ppm 4.41 (d, J=6.10 Hz, 2H) 6.56 (t, J=6.10 Hz, 1H) 6.92 (dd, J=8.14, 1.02 Hz, 1H) 7.18 (td, J=7.46, 1.36 Hz, 1H) 7.24-7.32 (m, 1H) 7.32-7.37 (m, 1 H) 7.37-7.44 (m, 1H) 7.46 (dd, J=7.80, 1.70 Hz, 1H) 7.50-7.57 (m, 2H) 7.79-7.88 (m, 1H) 8.15 (s, 1H) 8.29-8.38 (m, 2H).

Example 108

[4-(2,3-Dichloro-phenyl)-4H-[1,2,4]triazol-3-yl]-(2-thiophen-3-yl-pyridin-3-ylmethyl)-amine The title compound was prepared using the procedure as described in Example 100 substituting Example 96B for 2-methylbenzylamine. MS (ESI$^+$) m/z 402 (M+H)$^+$; $^1$H NMR (400 MHz, DMSO-d$_6$) δ ppm 4.52 (d, J=5.76 Hz, 2H) 6.71 (t, J=5.76 Hz, 1H) 7.32 (dd, J=7.80, 4.75 Hz, 1H) 7.48-7.55 (m, 1H) 7.56-7.61 (m, 2H) 7.63 (dd, J=4.92, 2.88 Hz, 1 H) 7.80-7.87 (m, 3H) 8.15-8.18 (m, 1H) 8.50 (dd, J=4.58, 1.53 Hz, 1H).

Example 109

[4-(2,3-Dichloro-phenyl)-4H-[1,2,4]triazol-3-yl]-[2-(pyridin-3-yloxy)-pyridin-3-ylmetyl]-amine

Example 109A 2-(Pyridin-3-yloxy)-nicotinonitrile

To a solution of pyridin-3-ol (1.3 g, 10 mmol) in N,N-dimethyl formamide (25 ml) was added 60 % NaH in mineral oil (0.3 g, 15 mmol) and 2-chloronicotinonitrile (1.38 g, 10 mmol) and heated at 120° C. for overnight. The reaction mixture was quenched with 1M NaHCO$_3$ and extracted with ethyl acetate (3×30 ml). The combined organic extracts were washed with saturated NaCl (50 ml), dried (Na$_2$SO$_4$), filtered and concentrated. The crude product was purified by flash column chromatography using dichloromethane to yield 1.1 g (50%) of product. MS (ESI$^+$) m/z 198 (M+H)$^+$.

Example 109B

C-[2-(Pyridin-3-yloxy)-pyridin-3-yl]-methylamine

To a solution of Example 109A (1.0 g, 5.1 mmole) in 7N NH$_3$ in methanol (1000 ml) was added Raney nickel (10 g) under argon atmosphere. The reaction mixture was kept on shaker under 60 psi H$_2$ atmosphere. After 6 hours at room temperature, the reaction mixture was filtered through a micro pore filter and concentrated to yield 0.9 g (88%) of product. MS (ESI$^+$) m/z 202 (M+H)$^+$.

Example 109C

[4-(2,3-Dichloro-phenyl)-4H-[1,2,4]triazol-3-yl]-[2-(pyridin-3-yloxy)-pyridin-3-ylmethyl]-amine The title compound was prepared using the procedure as described in Example 100 substituting Example 109B for 2-methylbenzylamine. MS (ESI$^+$) m/z 413 (M+H)$^+$; $^1$H NMR (400 MHz, DMSO-d$_6$) δ ppm 4.52 (d, J=5.76 Hz, 2H) 6.71 (t, J=5.76 Hz, 1H) 7.14 (dd, J=7.46, 4.75 Hz, 1H) 7.47 (dd, J=8.14, 4.75 Hz, 1H) 7.56 (t, J=7.97 Hz, 1H) 7.60-7.67 (m, 2H) 7.80 (dd, J=7.29, 1.86 Hz, 1H) 7.86 (dd, J=7.80, 1.70 Hz, 1H) 7.99 (dd, J=4.92, 1.86 Hz, 1H) 8.19 (s, 1H) 8.41-8.47 (m, 2H).

Example 110

[4-(2,3-Dichloro-phenyl)-4H-[1 2,4]triazol-3-yl]-[2-(1-methyl-pyrrolidin-3-yloxy)-pyridin-3-ylmethyl]-amine

Example 110A 2-(1-Methyl-pyrrolidin-3-yloxy)-nicotinonitrile

The title compound was prepared using the procedure as described in Example 109A substituting 1-Methyl-pyrrolidin-3-ol for pyridin-3-ol. MS (ESI$^+$) m/z 204 (M+H)$^+$.

Example 110B

C-[2-(1-Methyl-pyrrolidin-3-yloxy)-pyridin-3-yl]-methylamine

The title compound was prepared using the procedure as described in Example 109B substituting Example 110A for Example 109A. MS (ESI$^+$) m/z 208 (M+H)$^+$.

Example 110C

[4-(2,3-Dichloro-phenyl)-4H-[1,2,4]triazol-3-yl]-[2-(1-methyl-pyrrolidin-3-yloxy)-pyridin-3-ylmethyl]-amine The title compound was prepared using the procedure as described in Example 100 substituting Example 110B for 2-methylbenzylamine. MS (ESI$^+$) m/z 419 (M+H)$^+$; $^1$H NMR (300 MHz, DMSO-$d_6$) δ ppm 1.72-1.86 (m, 1H) 2.25 (s, 3H) 2.27-2.40 (m, 2H) 2.54-2.70 (m, 2H) 2.80 (dd, J=10.51, 6.10 Hz, 1H) 4.30 (d, J=5.76 Hz, 2H) 5.36 (t, 1H) 6.45 (t, J=5.93 Hz, 1H) 6.92 (dd, J=7.29, 4.92 Hz, 1H) 7.56 (t, J=7.97 Hz, 2H) 7.61-7.67 (m, 1H) 7.86 (dd, J=7.80, 1.70 Hz, 1H) 8.00 (dd, J=4.92, 1.86 Hz, 1H) 8.17 (s, 1H).

Example 111

[4-(2,3-Dichloro-phenyl)-5-methyl-4H-[1,2,4]triazol-3-yl]-(2-thiophen-3-yl-pyridin-3-ylmethyl)-amine The title compound was prepared using the procedure as described in Example 100 substituting Example 96B for 2-methylbenzylamine and triethylorthoacetate was for triethylorthoformate. MS (ESI$^+$) m/z 416 (M+H)$^+$; $^1$H NMR (400 MHz, DMSO-$d_6$) δ ppm 1.97 (s, 3H) 4.48 (d, J=5.76 Hz, 2H) 6.50 (t, J=5.76 Hz, 1H) 7.30 (dd, J=7.80, 4.75 Hz, 1 H) 7.50 (dd, J=5.09, 1.36 Hz, 1H) 7.57 (s, 3H) 7.77-7.90 (m, 3H) 8.45-8.52 (m, J=4.75, 1.70 Hz, 1H).

Example 112 tert-butyl 4-[3-({[4-(2,3-dichlorophenyl)-4H-1,2,4-triazol-3-yl]amino}methyl)pyridin-2-yl]-1,4-diazepane-1-carboxylate

Example 112A 4-(2-Cyano-phenyl)-[1,4]diazepane-1-carboxylic acid tert-butyl ester 2-Chloro-nicotinonitrile(1.0 g, 7.215 mmol) was added to a mixture of [1,4]Diazepane-1-carboxylic acid tert-butyl ester and potassium hydogencarbonate (0.87 g, 8.66 mmol) in N,N-dimethylformamide (20 mL). The mixture was heated at 90° C. overnight. The reaction mixture was poured onto ice and extracted with dichloromethane. The organic layer was washed with water and brine then dried over magnesium sulfate and filtered. The solvent was removed and the residue was purified by flash column chromatography on silica using ethyl acetate/heptane (50:50) mixture as the mobile phase to give 4-(2-Cyano-phenyl)-[1,4]diazepane-1-carboxylic acid tert-butyl ester. $^1$H-NMR (400 MHz, DMSO-$d_6$) δ 1.25 (d, 27 Hz, 9H), 1.81 (m, 1H), 1.87 (m, 1H), 3.31 (m, 2H), 3.55(m, 1H), 3.60 (m,1H), 3.84 (m, 2H), 3.94 (m, 2H), 6.75 (m,2H), 8.34 (m,1H).

Example 112B 4-(3-Aminomethyl-pyridin-2-yl)-[1,4]diazepane-1-carboxylic acid tert-butyl ester To a nitrogen-purged, thick-walled pressure vessel was added wet Raney nickel (~2 g). A solution of ammonia-saturated methanol (7.0N, 70 mL) was added, followed by Example 112A (7.215 mmol). The vessel was inserted into a Parr shaker and was charged with 60 psi of $H_2$ gas. The mixture was shaken at room temperature under static $H_2$ pressure for 16 hours. The $H_2$ gas was vented and the vessel was purged with nitrogen. The solids were removed by vacuum filtration through Celite®. The solvent/volatiles were removed by rotary evaporator to give the title compound which was used without further purification.

Example 112C 4-(3-{[4-(2,3-Dichloro-phenyl)-4H-[1,2,4]triazol-3-ylamino]-methyl}-pyridin-2-yl)[1,4]diazepane-1-carboxylic acid tert-butyl ester The title compound was prepared using the procedure as described in Example 100, substituting Example 112B for 2-methylbenzylamine. MS (ESI$^+$) m/z 518.6 (M+H)$^+$; $^1$H NMR (DMSO-$d_6$) δ 8,107 (s. 1H); 8,075 (m,1H); 7,811(m, 1H); 7,607(m,2H); 7,545(m,1H); 6.888(m,1H); 6.375(m, 1H); 4,360 (m,2H); 3,509(m,2H); 3,410(m,2H); 3,378(m, 2H); 3,288(m,2H); 1,838(m,2H); 1,383(s,9H).

Example 113

2-[4-(3-{[4-(2,3-Dichloro-phenyl)-4H-[1,2,4]triazol-3-ylamino]-methyl}-pyridin-2-yl)-[1,4]diazepan-1-yl]-acetamide

Example 113A

N-{[2-(1,4-diazepan-1-yl)pyridin-3-yl]methyl}-4-(2,3-dichlorophenyl)-4H-1,2,4-triazol-3-amine Trifluoroacetic acid (15 mL) was added to a solution of Example 112C (2.0 g, 3.86 mmol) in dichloromethane (75 mL) at 0° C. 5 minuted later, the ice bath was removed and the reaction mixture was stirred at room temperature for 16 hours. The reaction mixture was diluted with dichloromethane. The organic was washed with saturated sodium bicarbonate and the pH was adjusted to 9. The layers were separated and the aqueous layer was extracted with dichloromathane. The combined organic layer was washed with brine, dried over magnium sulfate, filtered and concentrated to yield the title compound that was used without further purification.

Example 113B

2-[4-(3-{[4-(2,3-Dichloro-phenyl)-4H-[1,2,4]triazol-3-ylamino]-methyl}-pyridin-2-yl)-[1,4]diazepan-1-yl]-acetamide To a solution of Example 113A (250 mg, 0.597 mmol) in dimethylformamide (7 ml) was added potassium carbonate (165 mg, 1.194 mmol) and bromoacetamide (124 mg, 0.896 mmol). The reaction mixture was stirred at room temperature for 16 hours then poured onto ice water. The aqueous mixture was extracted with dichloromethane. The organic layer was washed with brine, dried over magnesium sulfate, filtered and concentrated. The residue was purified by flash column chromatography using dichloromethane/methanol (80:20) to give the title compound (109 mg). MS (ESI$^+$) m/z 475.6 (M+H)$^+$; R$_f$=1.41. $^1$H NMR (DMSO-d$_6$) δ 8,170 (s, 1H); 8,054 (d,1H); 7,832 (d,1H); 7,579(m,3H); 7,251 (s,1H); 7,112 (s,1H); 6,832 (dd,1H); 6,545 (t,1H); 4,338 (d, 2H); 3,423 (m,4H); 3,011 (s,2H); 2,772 (m,2H); 2,710 (m,2H); 1,856(m,2H).

Example 114

4-(2,3-dichlorophenyl)-N-{[2-(4-isopropyl-1,4-diazepan-1-yl)pyridin-3-yl]methyl}-4H-1,2,4-triazol-3-amine To a solution of Example 113A in 1,2-dichloroethane (10 ml) was added acetone (3 mL) and sodium triacetoxyborohydride (253 mg, 1.194 mmol). The reaction mixture was stirred at room temperature overnight. Saturated sodium bicarbonate was added and the layers were separated. The aqueous layer was extracted with dichloromethane. The combined organic layer was washed with brine, dried over magnesium sulfate, filtered and concentrated. The residue was purified by flash column chromatography using dichloromethane/methanol (80:20) to give the title compound. MS (ESI$^+$) m/z 460.6 (M+H)$^+$; R$_f$=1.47. $^1$H NMR (DMSO-d$_6$) δ 8,171 (s, 1H); 8,049 (d, 1H); 7,831(d, 1H); 7,586(m, 3H); 6,837 (dd, 1H); 6,521 (t, 1H); 4,353 (d, 2H); 3,377 (m, 4H); 3,289 (m, 1H); 2,862 (m, 2H); 2,642 (m, 2H); 1,773 (m, 2H); 0,949 (m, 6H).

f) Biological Activity

In Vitro Data

Tissue Culture: Cells of the THP-1 monocytic cell line (American Type Culture Collection, Rockville, Md.) were maintained in the log phase of growth in RPMI medium containing high glucose and 10% fetal calf serum (BRL, Grand Island, N.Y.) according to established procedures (Humphrey and Dubyak, *J. Immunol.* Vol. 275 pages 26792-26798, 1996). Fresh vials of frozen THP-1 cells were initiated for growth every eight weeks. To differentiate THP-1 cells into a macrophage phenotype, a final concentration of 25 ng/ml of LPS and 10 ng/ml of IFNγ were added to the cells (Humphrey and Dubyak 1996) either for 3 hours for IL-1β release assays or overnight (16 hours) for pore formation studies. 1321N1 cells stably expressing the recombinant human P2X$_7$ receptor were grown and used according to previously published protocols (Bianchi, et al, *Eur. J. Pharmacol.* Vol. 376, pages 127-138, 1999; Lynch et al., *Mol. Pharmacol.* Vol. 56, pages 1171-1181, 1999). For both the pore formation and IL-1β release assays, cell density and viability were routinely assessed prior to each experiment by trypan dye exclusion and cells found to be >90% viable following differentiation.

IL-1β Release: THP-1 cells were plated in 24-well plates at a density of 1×10$^6$ cells /well/ml. On the day of the experiment, cells were differentiated with 25 ng/ml LPS and 10 ng/ml final concentration of γIFN for 3 hours at 37° C. Solutions of antagonist compounds were prepared by serial dilutions of a 10 mM DMSO solution of the antagonist into the PBS solution. In the presence of the differentiation media, the cells were incubated with the antagonists of the present invention for 30 minutes at 37° C. followed by a challenge with 1 mM BZATP for an additional 30 minutes at 37° C. Supernatants of the samples were collected after a 5 minute centrifugation in microfuge tubes to pellet the cells and debris and to test for mature IL-1β released into the supernatant using either R & D Systems Human IL-1β ELISA assay or Endogen Human IL-1β ELISA, following the manufacturer's instructions. The maximum IL-1β release at each concentration of test compound was normalized to that induced by BzATP alone to determine the activity of the test compound. Antagonist potency was expressed as the concentration producing a 50% reduction in release of IL-1β or IC$_{50}$. Representative compounds of the present invention when tested with the above assay demonstrated antagonist activity at the P2X$_7$ receptor with IC$_{50}$ equal or less than 1 μM.

In Vivo Data

Determination of Antinociceptive Effect

Animal handling and experimental protocols were approved by the Institutional Animal Care and Use Committee (IACUC) at Abbott Laboratories. For all surgical procedures, animals were maintained under halothane anesthesia (4% to induce, 2% to maintain), and the incision sites were sterilized using a 10% povidone-iodine solution prior to and after surgeries.

CFA model: The capacity of the antagonists to reduce inflammatory hyperalgesia was evaluated using the complete Freund's adjuvant (CFA) model. In these experiments, animals were subjected to intraplantar injection of CFA 48 hours before administration of the P2X$_7$ antagonists. Inhibition of thermal hyperalgesia was determined 30 minutes after antagonist administration by observation of paw withdrawal latency and comparison to response of the contralateral paw. Representative compounds were active in reducing tactile allodynia when administered subcutaneously using this model.

Chung model: Efficacy in the reduction of neuropathic pain was evaluated using the L5/L6 spinal nerve tight ligation (Chung) model in rats. In these experiments, spinal nerve ligation was performed 7-14 days prior to assay. Tactile allodynia was induced by application of a von Frey hair 30 minutes after intraperitoneal administration of the antagonist. Reduction in tactile allodynia was measured by determination of the paw withdrawal threshold and comparison to the contralateral paw. Representative compounds were active in reducing tactile allodynia when tested using this model. (Jarvis et al., *Proc. Natl. Acad. USA* Vol. 99. pages 17179-17184, 2002).

Zymosan Method: Mice were dosed with experimental compounds orally or subcutaneously 30 minutes prior to injection of zymosan. Mice were then injected intraperitonealy with 2 mg/animal of zymosan suspended in saline. Four hours later the animals were euthanized by CO$_2$ inhalation and the peritoneal cavities lavaged with 2×1.5 mL of ice cold phosphate buffered saline containing 10 units of heparin/ml. For IL-1β determination the samples were spun at 10,000×g in a refrigerated microfuge (4° C.), supernatants removed and frozen until ELISAs (Enzyme Linked Immuno-Assay) were performed. ELISAs were performed according to manufacture's instructions. IL-1β was determined relative to vehicle control (Perretti M. et al., Agents *Actions* Vol 35(1-2) pages 71-78 (1992); Torok K, et al., *Inflamm Res*. Vol 44(6) pages 248-252 (1995)). Representative compounds of this invention were active as P2X7 antagonists in inhibiting IL-1β release in this assay when administered subcutaneously.

We claim:

1. A compound having formula (I) or (II)

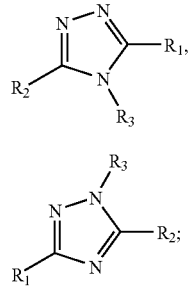

or a pharmaceutically acceptable salt, prodrug, salt of a prodrug or a combination thereof, wherein $R_1$ is hydrogen, alkyl, haloalkyl or —CN;
$R_2$ is —N(H)—(CR$_u$R$_v$)—R$_{2a}$, —N(H)—R$_{2b}$ or R$_{2b}$; and
$R_3$ is

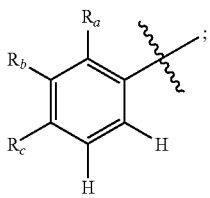

wherein
$R_{2a}$ is a group of formula (a) or (b);

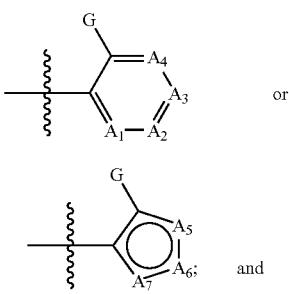

$R_{2b}$ is a group of formula (c), (d) or (e)

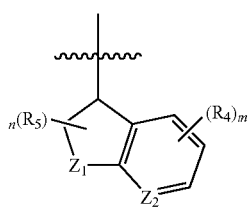

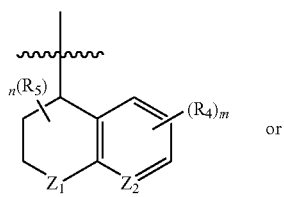

or
$R_2$ is

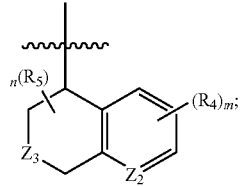

and $R_3$ is $R_{2b}$;
wherein
$R_{2b}$ is a group of formula (c), (d) or (e)

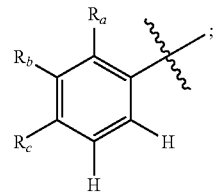

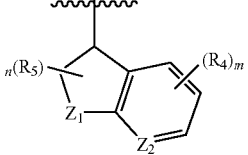

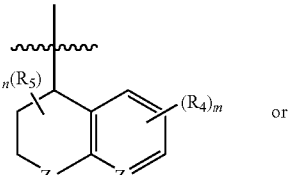

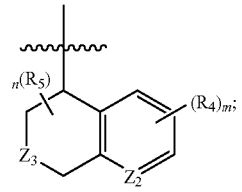

$Z_1$ at each occurrence is independently C, C(H), C(H)$_2$, O, S, S(O), S(O)$_2$, N(H), N(alkyl) or N(acyl);
$Z_2$ at each occurrence is independently C, C(H), or N;
$Z_3$ at each occurrence is independently O, S, S(O), S(O)$_2$, N(H), N(alkyl) or N(acyl);
$R_4$ at each occurrence is independently halo, alkyl, —CN, —OR$_A$, —SR$_A$, —N(R$_A$)(R$_B$) or haloalkyl;
$R_5$ at each occurrence is independently alkyl, halo or haloalkyl;

m at each occurrence is independently 0, 1, 2 or 3;

n at each occurrence is independently 0, 1, 2 or 3;

$R_a$ and $R_b$ at each occurrence are each independently halo, —CN, haloalkyl, haloalkoxy or alkyl;

$R_c$ at each occurrence is independently hydrogen, halo, haloalkyl, alkoxy, haloalkoxy or alkyl;

each of $R_u$ and $R_v$ at each occurrence is independently hydrogen, alkyl or haloalkyl;

$A_1$, $A_2$, $A_3$ and $A_4$ are —C($R_w$); or one or two of $A_1$, $A_2$, $A_3$ and $A_4$ are N, and the others are —C($R_w$); or one of $A_1$, $A_2$, $A_3$ and $A_4$ is $N^+$—$O^-$ and the others are —C($R_w$); wherein $R_w$ at each occurrence is independently hydrogen, halo, alkyl, alkenyl, —$OR_A$, —$SR_A$, —$N(R_A)(R_B)$ or haloalkyl;

$A_5$ is N, $A_6$ is O or S and $A_7$ is C(H) or C(alkyl), or $A_5$ is N, $A_6$ is C(H) or C(alkyl), and $A_7$ is O or S, or one of $A_5$, $A_6$ and $A_7$ is S and the others are independently C(H) or C(alkyl);

G is -$W_2$ or -$L_2$-$W_2$; or

G is hydrogen, alkyl, —Oalkyl, —$NH_2$, —N(H)(alkyl), —N(alkyl)$_2$, —S(O)alkyl, —S(O)$_2$alkyl, —S(O)$_2NH_2$, —S(O)$_2$N(H)(alkyl), —S(O)$_2$N(alkyl)$_2$, —C(O)$NH_2$, —C(O)N(H)(alkyl), —C(O)N(alkyl)$_2$, -$W_2$ or -$L_2$-$W_2$, when one of $A_1$, $A_2$, $A_3$ and $A_4$ is N;

$L_2$ is N(H), N(alkyl), O, S, S(O), S(O)$_2$, S(O)$_2$N(H), SO$_2$N(alkyl), N(H)S(O)$_2$, N(alkyl)S(O)$_2$, CON(H), CON(alkyl), N(H)CO, N(alkyl)CO); and $W_2$ at each occurrence is independently aryl, heteroaryl or heterocycle; and each $W_2$ is independently unsubstituted or substituted with 1, 2 or 3 substituents selected from the group consisting of =O, halo, —CN, —$NO_2$, alkyl, alkenyl, —$OR_A$, —$SR_A$, —S(O)$_2R_A$, —S(O)$_2$N($R_A$)($R_B$), —N($R_A$)($R_B$), —C(O)$R_A$, —C(O)N($R_A$)($R_B$), —C(O)$OR_A$, haloalkyl, -alkyl-$OR_A$, -alkyl-$SR_A$, -alkyl-S(O)$_2R_A$, -alkyl-S(O)$_2$N($R_A$)($R_B$), -alkyl-N($R_A$)($R_B$), -alkyl-C(O)$R_A$, -alkyl-C(O)N($R_A$)($R_B$), and -alkyl-C(O)$OR_A$;

$R_A$ at each occurrence is independently hydrogen, alkyl, alkenyl or haloalkyl; and $R_B$ at each occurrence is independently hydrogen, alkyl, or haloalkyl.

2. The compound of claim 1 having formula (I)

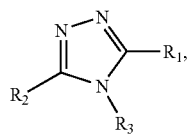
(I)

wherein $R_1$ is hydrogen, alkyl, haloalkyl or —CN;

$R_3$ is

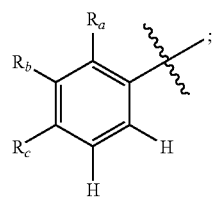

and $R_2$ is —N(H)—(C$R_uR_v$)—$R_{2a}$.

3. The compound of claim 2 wherein $R_{2a}$ is

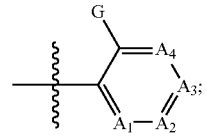

and G is -$W_2$, wherein $W_2$ is independently aryl, heteroaryl or heterocycle, and is independently unsubstituted or substituted with 1, 2 or 3 substituents selected from the group consisting of =O, halo, —CN, —$NO_2$, alkyl, alkenyl, —$OR_A$, —$SR_A$, —S(O)$_2R_A$, —S(O)$_2$N($R_A$)($R_B$), —N($R_A$)($R_B$), —C(O)$R_A$, —C(O)N($R_A$)($R_B$), —C(O)$OR_A$, haloalkyl, -alkyl-$OR_A$, -alkyl-$SR_A$, -alkyl-S(O)$_2R_A$, -alkyl-S(O)$_2$N($R_A$)($R_B$), -alkyl-N($R_A$)($R_B$), -alkyl-C(O)$R_A$, -alkyl-C(O)N($R_A$)($R_B$), and -alkyl-C(O)$OR_A$.

4. The compound of claim 3 that is selected from the group consisting of

[4-(2,3-Dichloro-phenyl)-4H-[1,2,4]triazol-3-yl]-(2-pyrrolidin-1-yl-pyridin-3-ylmethyl)-amine, tert-butyl 4-[3-(\{[4-(2,3-dichlorophenyl)-4H-1,2,4-triazol-3-yl]amino\}methyl)pyridin-2-yl]-1,4-diazepane-1-carboxylate;

2-[4-(3-\{[4-(2,3-Dichloro-phenyl)-4H-[1,2,4]triazol-3-ylamino]-methyl\}-pyridin-2-yl)-[1,4]diazepan-1-yl]-acetamide;

4-(2,3-dichlorophenyl)-N-\{[2-(4-isopropyl-1,4-diazepan-1-yl)pyridin-3-yl]methyl\}-4H-1,2,4-triazol-3-amine;

[4-(2,3-Dichloro-phenyl)-4H-[1,2,4]triazol-3-yl]-(2-thiophen-3-yl-pyridin-3-ylmethyl)-amine, and

[4-(2,3-Dichloro-phenyl)-5-methyl-4H-[1,2,4]triazol-3-yl]-(2-thiophen-3-yl-pyridin-3-ylmethyl)-amine.

5. The compound of claim 2 wherein $R_{2a}$ is

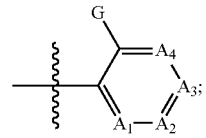

and G is G is hydrogen, alkyl, —Oalkyl, —$NH_2$, —N(H)(alkyl), —N(alkyl)$_2$, —S(O)alkyl, —S(O)$_2$alkyl, —S(O)$_2NH_2$, —S(O)$_2$N(H)(alkyl), —S(O)$_2$N(alkyl)$_2$, —C(O)$NH_2$, —C(O)N(H)(alkyl), —C(O)N(alkyl)$_2$, -$W_2$ or -$L_2$-$W_2$, when one of $A_1$, $A_2$, $A_3$ and $A_4$ is N.

6. The compound of claim 5 that is selected from the group consisting of

[4-(2,3-Dichloro-phenyl)-4H-[1,2,4]triazol-3-yl]-pyridin-3-ylmethyl-amine, and

[4-(2,3-Dichloro-phenyl)-4H-[1,2,4]triazol-3-yl]-(2-methyl-pyridin-3-ylmethyl)-amine.

7. The compound of claim 2 wherein $R_{2a}$ is

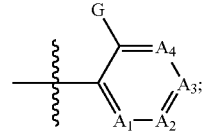

and G is -$L_2$-$W_2$.

8. The compound of claim 7 wherein $L_2$ is O and $W_2$ is selected from unsubstituted or substituted aryl, heteroaryl or heterocycle.

9. The compound of claim 8 that is selected from the group consisting of
[4-(2,3-Dichloro-phenyl)-4H-[1,2,4]triazol-3-yl]-[2-(5-fluoro-pyridin-3-yloxy)-pyridin-3-ylmethyl]-amine,
[4-(2,3-Dichloro-phenyl)-4H-[1,2,4]triazol-3-yl]-[2-(pyridin-2-yloxy)-benzyl]-amine,
[4-(2,3-Dichloro-phenyl)-4H-[1,2,4]triazol-3-yl]-[2-(pyridin-3-yloxy)-benzyl]-amine,
[4-(2,3-Dichloro-phenyl)-4H-[1,2,4]triazol-3-yl]-[2-(pyridin-3-yloxy)-pyridin-3-ylmethyl]-amine, and
[4-(2,3-Dichloro-phenyl)-4H-[1,2,4]triazol-3-yl]-[2-(1-methyl-pyrrolidin-3-yloxy)-pyridin-3-ylmethyl]-amine.

10. The compound of claim 2 wherein $R_{2a}$ is

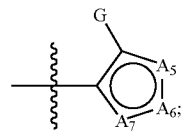

and G is -$W_2$ or -$L_2$-$W_2$; or
G is hydrogen, alkyl, —Oalkyl, —$NH_2$, —N(H)(alkyl), —N(alkyl)$_2$, —S(O)alkyl, —S(O)$_2$alkyl, —S(O)$_2$NH$_2$, —S(O)$_2$N(H)(alkyl), —S(O)$_2$N(alkyl)$_2$, —C(O)NH$_2$, —C(O)N(H)(alkyl), —C(O)N(alkyl)$_2$, -$W_2$ or -$L_2$-$W_2$, when one of $A_1$, $A_2$, $A_3$ and $A_4$ is N.

11. The compound of claim 1 having formula (I)

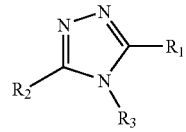

(I)

wherein $R_1$ is hydrogen, alkyl, haloalkyl or —CN;
$R_3$ is

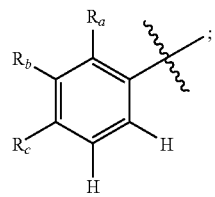

and
$R_2$ is —N(H)—$R_{2b}$.

12. The compound of claim 1 wherein $R_{2b}$ is

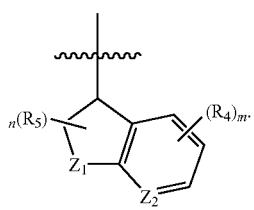

13. The compound of claim 11 wherein $R_{2b}$ is

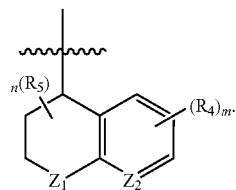

14. The compound of claim 11 wherein $R_{2b}$ is

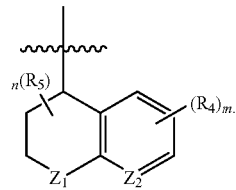

15. The compound of claim 1 having formula (I)

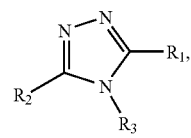

(I)

wherein $R_1$ is hydrogen, alkyl, haloalkyl or —CN;
$R_3$ is

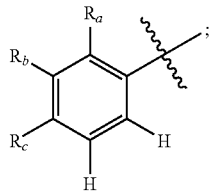

and
$R_2$ is $R_{2b}$.

16. The compound of claim 15 wherein $R_{2b}$ is

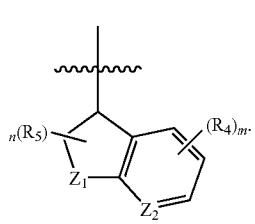

17. The compound of claim 15 wherein R$_{2b}$ is

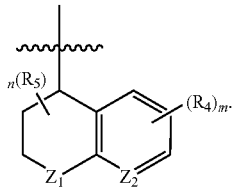

18. The compound of claim 15 wherein R$_{2b}$ is

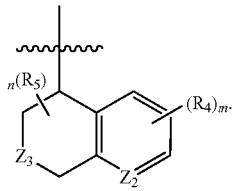

19. The compound of claim 1 having formula (I)

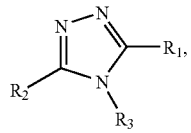
(I)

wherein R$_1$ is hydrogen, alkyl, haloalkyl or —CN;
R$_2$ is

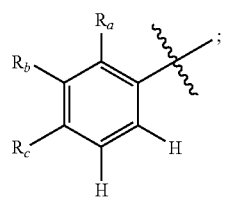

and
R$_3$ is R$_{2b}$.

20. The compound of claim 19 wherein
R$_3$ is R$_{2b}$, and
R$_{2b}$ is a group of formula (c)

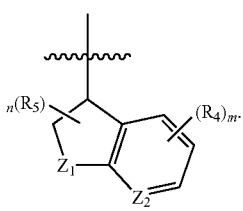
(c)

21. The compound of claim 18 that is selected from the group consisting of
3-(2,3-dichlorophenyl)-4-(2,3-dihydro-1H-inden-1-yl)-4H-1,2,4-triazol,
3-(2,3-dichlorophenyl)-4-[2,3-dihydro-1-benzofuran-3-yl]-4H-1,2,4-triazole,
3-(2,3-dichlorophenyl)-4-[(1R)-2,3-dihydro-1H-inden-1-yl]-4H-1,2,4-triazole,
3-(2,3-dichlorophenyl)-4-[(1S)-2,3-dihydro-1H-inden-1-yl]-4H-1,2,4-triazole,
3-(2,3-dichlorophenyl)-4-(3-methyl-2,3-dihydro-1H-inden-1-yl)-4H-1,2,4-triazole,
3-[2-chloro-3-(trifluoromethyl)phenyl]-4-[(1R)-2,3-dihydro-1H-inden-1-yl]-4H-1,2,4-triazole,-(2,3-dichlorophenyl)-4-(4-fluoro-2,3-dihydro-1H-inden-1-yl)-4H-1,2,4-triazole, and
3-(2,3-dichlorophenyl)-4-[5-(trifluoromethyl)-2,3-dihydro-1H-inden-1-yl]-4H-1,2,4- triazole.

22. The compound of claim 19 wherein
R$_{2b}$ is a group of formula (d)

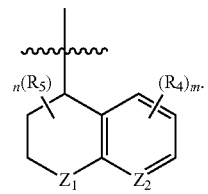
(d)

23. The compound of claim 22 that is selected from the group consisting of
3-(2,3-dichlorophenyl)-4-(1,2,3,4-tetrahydronaphthalen-1-yl)-4H-1,2,4-triazole,
3-(2,3-dichlorophenyl)-4-(4,4-dimethyl-1,2,3,4-tetrahydronaphthalen-1-yl)-4H-1,2,4-triazole, and
3-(2,3-dichlorophenyl)-4-(3,4-dihydro-2H-chromen-4-yl)-4H-1,2,4-triazole.

24. The compound of claim 19 wherein
R$_{2b}$ is a group of formula (e)

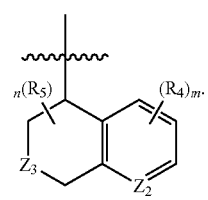
(e)

25. The compound of claim 1 having formula (II)

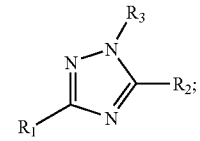
(II)

wherein
R$_1$ is hydrogen, alkyl, haloalkyl or —CN;
R$_2$ is —N(H)—(CR$_u$R$_v$)—R$_{2a}$; and
R$_3$ is

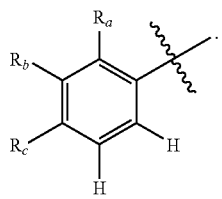

26. The compound of claim 25 wherein $R_{2a}$ is

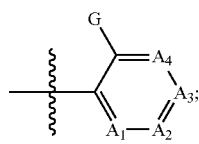

and G is -$W_2$, wherein $W_2$ is independently aryl, heteroaryl or heterocycle, and is independently unsubstituted or substituted with 1, 2 or 3 substituents selected from the group consisting of =O, halo, —CN, —NO$_2$, alkyl, alkenyl, —OR$_A$, —SR$_A$, —S(O)$_2$R$_A$, —S(O)$_2$N(R$_A$)(R$_B$), —N(R$_A$)(R$_B$), —C(O)R$_A$, —C(O)N(R$_A$)(R$_B$), —C(O)OR$_A$, haloalkyl, -alkyl-OR$_A$, -alkyl-SR$_A$, -alkyl-S(O)$_2$R$_A$, -alkyl-S(O)$_2$N(R$_A$)(R$_B$), -alkyl-N(R$_A$)(R$_B$), -alkyl-C(O)R$_A$, -alkyl-C(O)N(R$_A$)(R$_B$), and -alkyl-C(O)OR$_A$.

27. The compound of claim 26 selected from the group consisting of:
   1-(2,3-dichlorophenyl)-N-[(2-pyrrolidin-1-ylpyridin-3-yl)methyl]-1H-[1,2,4]triazole-5-amine,
   1-(2,3-dichlorophenyl)-N-[(2-morpholin-4-ylpyridin-3-yl)methyl]-1H-[1,2,4]-triazol-5-amine,
   [2-(2,3-Dichloro-phenyl)-2H-[1,2,4]triazol-3-yl]-(2-thiophen-3-yl-pyridin-3-ylmethyl)-amine, and
   (2-Azetidin-1-yl-pyridin-3-ylmethyl)-[2-(2,3-dichloro-phenyl)-2H-[1,2,4]triazol-3-yl]-amine.

28. The compound of claim 25 wherein $R_{2a}$ is

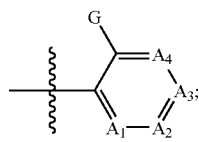

and G is hydrogen, alkyl, —Oalkyl, —NH$_2$, —N(H)(alkyl), —N(alkyl)$_2$, —S(O)alkyl, —S(O)$_2$alkyl, —S(O)$_2$NH$_2$, —S(O)$_2$N(H)(alkyl), —S(O)$_2$N(alkyl)$_2$, —C(O)NH$_2$, —C(O)N(H)(alkyl), or —C(O)N(alkyl)$_2$.

29. The compound of claim 28 selected from the group consisting of:
   [2-(2,3-Dichloro-phenyl)-2H-[1,2,4]triazol-3-yl]-pyridin-3-ylmethyl-amine, and
   [2-(2,3-Dichloro-phenyl)-2H-[1,2,4]triazol-3-yl]-(2-methyl-pyridin-3-ylmethyl)-amine.

30. The compound of claim 25 wherein $R_{2a}$ is

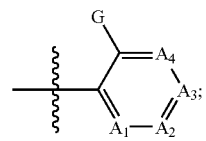

and G is -$L_2$-$W_2$.

31. The compound of claim 30 wherein $L_2$ is O and $W_2$ is aryl or heteroaryl.

32. The compound of claim 31 selected from the group consisting of:
   [2-(2,3-Dichloro-phenyl)-2H-[1,2,4]triazol-3-yl]-[2-(pyridin-3-yloxy)-benzyl]-amine, and
   [2-(2,3-Dichloro-phenyl)-2H-[1,2,4]triazol-3-yl]-[2-(pyridin-3-yloxy)-pyridin-3-ylmethyl]-amine.

33. The compound of claim 25 wherein $R_{2a}$ is

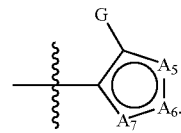

34. The compound of claim 1 having formula (II)

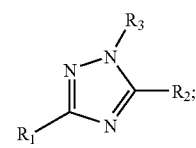

(II)

wherein
   $R_1$ is hydrogen, alkyl, haloalkyl or —CN;
   $R_2$ is —N(H)—$R_{2b}$; and
   $R_3$ is

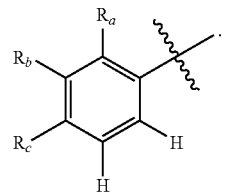

35. The compound of claim 34 wherein
   $R_{2b}$ is a group of formula (c)

(c)

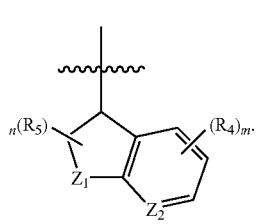

36. The compound of claim 34 wherein
$R_{2b}$ is a group of formula (d)

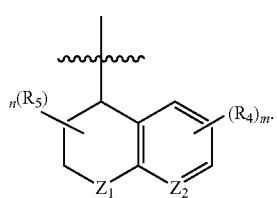
(d)

37. The compound of claim 34 wherein
$R_{2b}$ is a group of formula (e)

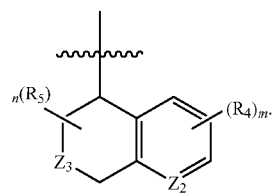
(e)

38. The compound of claim 1 having formula (II)

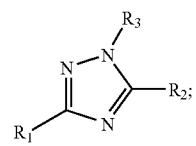
(II)

wherein
$R_1$ is hydrogen, alkyl, haloalkyl or —CN;
$R_2$ is —$R_{2b}$; and
$R_3$ is

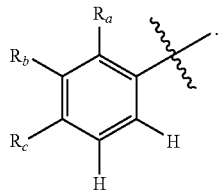

39. The compound of claim 38 wherein
$R_{2b}$ is a group of formula (c)

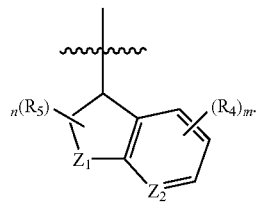
(c)

40. The compound of claim 39 that is
1-[2-chloro-3-(trifluoromethyl)phenyl]-5-(2,3-dihydro-1H-inden-1-yl)-1H-1,2,4-triazole.

41. The compound of claim 38 wherein
$R_{2b}$ is a group of formula (d)

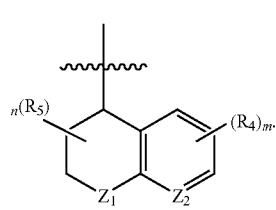
(d)

42. The compound of claim 38 wherein
$R_{2b}$ is a group of formula (e)

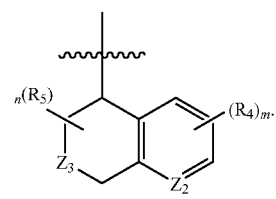
(e)

43. The compound of claim 1 having formula (II)

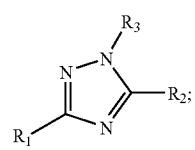
(II)

wherein
$R_1$ is hydrogen, alkyl, haloalkyl or —CN;
$R_2$ is

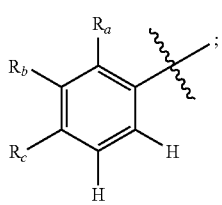

and
$R_3$ is $R_{2b}$.

44. The compound of claim 43 wherein
$R_{2b}$ is a group of formula (c)

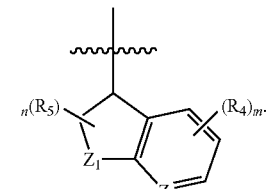
(c)

45. The compound of claim 44 that is 5-[2-chloro-3-(trifluoromethyl)phenyl]-1-[2,3-dihydro-1H-inden-1-yl]-1H-1,2,4-triazole.

46. The compound of claim 43 wherein $R_{2b}$ is a group of formula (d)

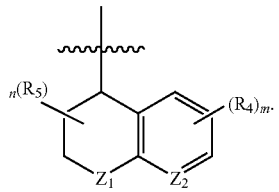

(d)

47. The compound of claim 43 wherein $R_{2b}$ is a group of formula (e)

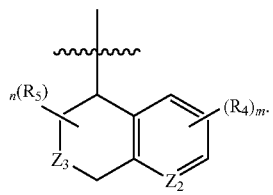

(e)

48. A pharmaceutical composition comprising a therapeutically effective amount of a compound of formula (I) or formula (II) as described in claim 1, or a therapeutically acceptable salt, solvate, prodrug, salt of a prodrug, or combination thereof, and a pharmaceutically acceptable carrier.

* * * * *

UNITED STATES PATENT AND TRADEMARK OFFICE
CERTIFICATE OF CORRECTION

PATENT NO. : 7,709,469 B2
APPLICATION NO. : 11/593377
DATED : May 4, 2010
INVENTOR(S) : Carroll et al.

Page 1 of 1

It is certified that error appears in the above-identified patent and that said Letters Patent is hereby corrected as shown below:

Column 65, line 12, claim 1: "$A_4$is $N^+$" to read as --$A_4$ is $N^+$--

Column 65, line 16, claim 1: "$A_7$is" to read as --$A_7$ is--

Column 65, line 28, claim 1: "N(alkyl)CO)" to read as --N(alkyl)CO--

Column 66, line 21, claim 4: "consisting of" to read as --consisting of:--

Column 66, line 23, claim 4: "amine," to read as --amine;--

Column 66, line 24, claim 4: "tert-butyl  4" to read as --tert-butyl 4--

Column 66, line 33, claim 4: "amine, and" to read as --amine; and--

Column 66, line 46, claim 5: "G is G is" to read as --G is--

Column 66, line 52, claim 6: "consisting of" to read as --consisting of:--

Column 67, line 5, claim 9: "consisting of" to read as --consisting of:--

Column 70, line 2, claim 21: "consisting of" to read as --consisting of:--

Column 70, line 4, claim 21: "triazol" to read as --triazole--

Column 70, line 14, claim 21: "triazole,-(2,3" to read as --triazole, 3-(2,3--

Column 70, line 33, claim 23: "consisting of" to read as --consisting of:--

Signed and Sealed this
Nineteenth Day of April, 2011

David J. Kappos
*Director of the United States Patent and Trademark Office*